(12) United States Patent
Thorson

(10) Patent No.: US 7,348,309 B2
(45) Date of Patent: Mar. 25, 2008

(54) GLYCORANDOMIZATION AND PRODUCTION OF NOVEL VANCOMYCIN ANALOGS

(75) Inventor: Jon Thorson, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 505 days.

(21) Appl. No.: 10/670,073

(22) Filed: Sep. 24, 2003

(65) Prior Publication Data

US 2004/0259228 A1 Dec. 23, 2004

Related U.S. Application Data

(63) Continuation-in-part of application No. 10/109,672, filed on Apr. 1, 2002, now Pat. No. 6,884,604.

(60) Provisional application No. 60/413,520, filed on Sep. 25, 2002, provisional application No. 60/413,393, filed on Sep. 25, 2002, provisional application No. 60/413,376, filed on Sep. 25, 2002, provisional application No. 60/279,682, filed on Mar. 30, 2001.

(51) Int. Cl.
*A61K 38/16* (2006.01)

(52) U.S. Cl. ......................................... 514/8
(58) Field of Classification Search ...................... None
See application file for complete search history.

(56) References Cited

U.S. PATENT DOCUMENTS 7,259,141 B2 * 8/2007 Thorson ........................ 514/8

OTHER PUBLICATIONS

March, Advanced Organic Chemistry (1985) 3rd Edition, pp. 740-744.*

Weymouth-Wilson, A.C., Nat. Prod. Rep., 1997, 99-110, 14.
Thorson, J.S., et al., Curr. Org. Chem., 2001, 139-167, 5.
Mendez, C. & Salas, J.A., Trends Biotechnol, 2001, 449-456, 19.
Nicolaou, K.C., Boddy, C.N., Brase, S. & Winssinger, N., Angew. Chem. Inc. Ed., 1999, 2096-2152, 38.
Hubbard, B.K. & Walsh, C.T., Angew. Chem. Int. Ed., 2003, 730-765, 42.
Solenberg, P.J., et al., Chem. Biol., 1997, 195-202, 4.
Losey, H.C., et al., Biochemistry, 2001, 4745-4755, 40.
Losey, H.C., et al., Chem. Biol., 2002, 1305-1314, 9.
Thorson, J.S., Barton, W.A., Hoffmeister, D., Albermann, C. & Nikolov, D.B., ChemBioChem., in press.
Hang, H.C. & Bertozzi, C.R., Acc. Chem. Res., 2001, 727-735, 34.
Kolb, H.C., Finn, M.G. & Sharpless, K.B., Angew Chem. Int. Ed., 2001, 2004-2021, 40.
Nicolaou, K.C., et al., Chem. Eur. J., 2001, 3798-3823, 7.
Hlasta, D.J. & Ackerman, J.H., J. Org. Chem., 1994, 6184-6189, 59.
Wang, Q., et al., J. Am. Chem. Soc., 2003, 3192-3193, 125.
Ge, M., et al., Science, 1999, 507-511, 284.

* cited by examiner

*Primary Examiner*—Cecilia J. Tsang
*Assistant Examiner*—Thomas S. Heard
(74) *Attorney, Agent, or Firm*—Quarles & Brady LLP

(57) ABSTRACT

The present invention provides combinatorial methods for rapidly generating a diverse library of glycorandomized structures, comprising incubating one or more aglycons and a pool of NDP-sugars in the presence of a glycosyltransferase. The glycosyltransferase may be one that is associated with or involved in production of natural secondary metabolites, or one which is putatively associated with or involved in production of natural secondary metabolites. The glycosyltransferase may show significant flexibility with respect to its NDP-sugar donors and/or its aglycons. NDP-sugar donors may be commercially available, or may be produced by utilizing mutant or wild type nucleotidyltransferases significant flexibility with respect to their substrates.

2 Claims, 17 Drawing Sheets

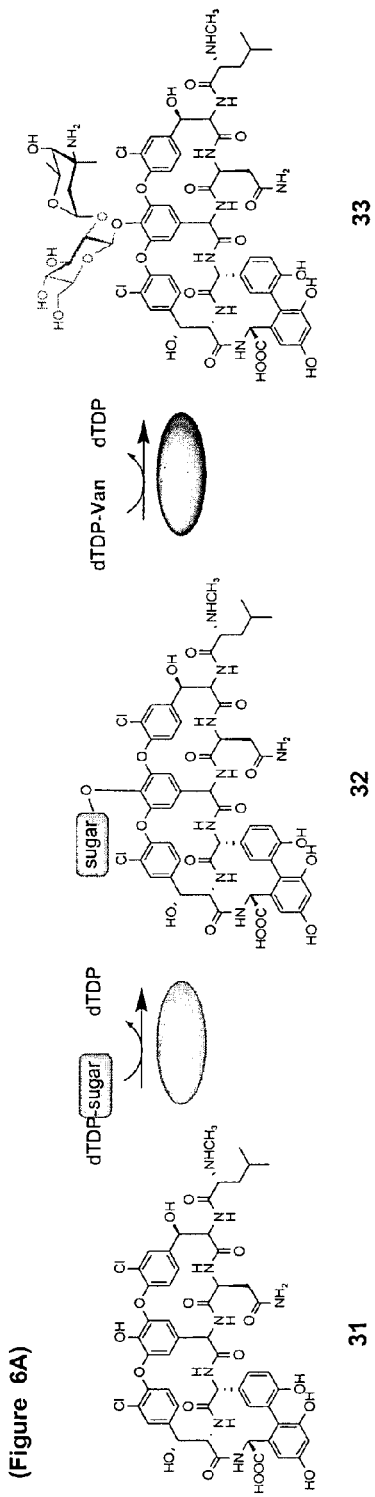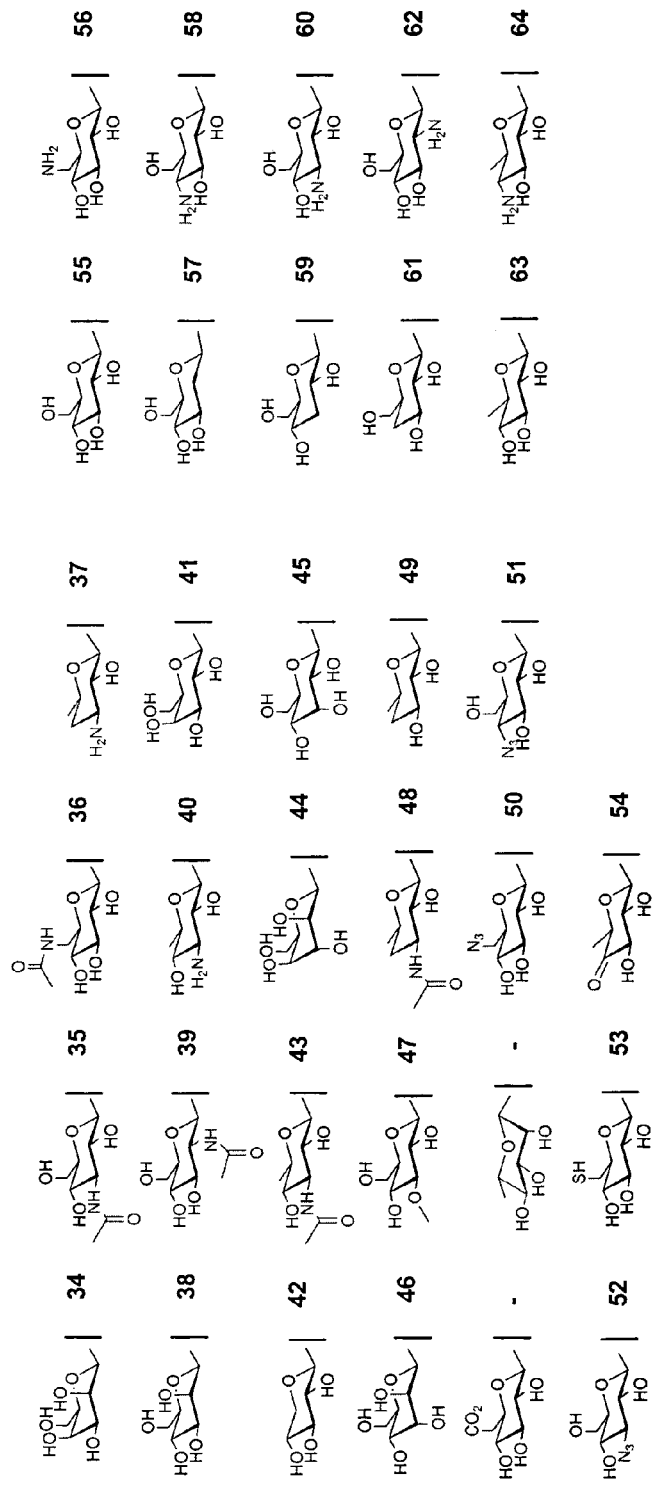
(Figure 6A)
(Figure 6B)

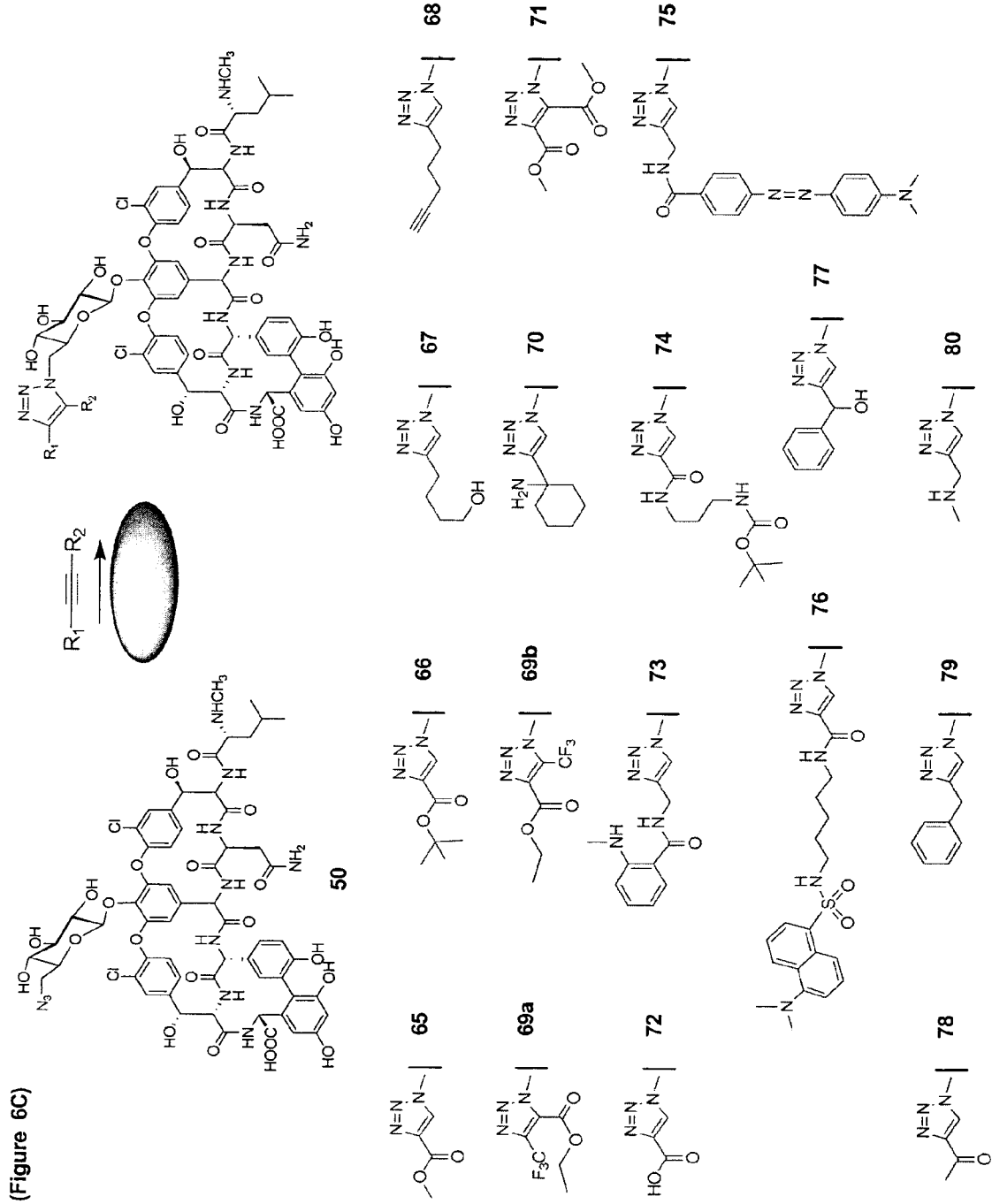
(Figure 6C)

(Figure 6D)
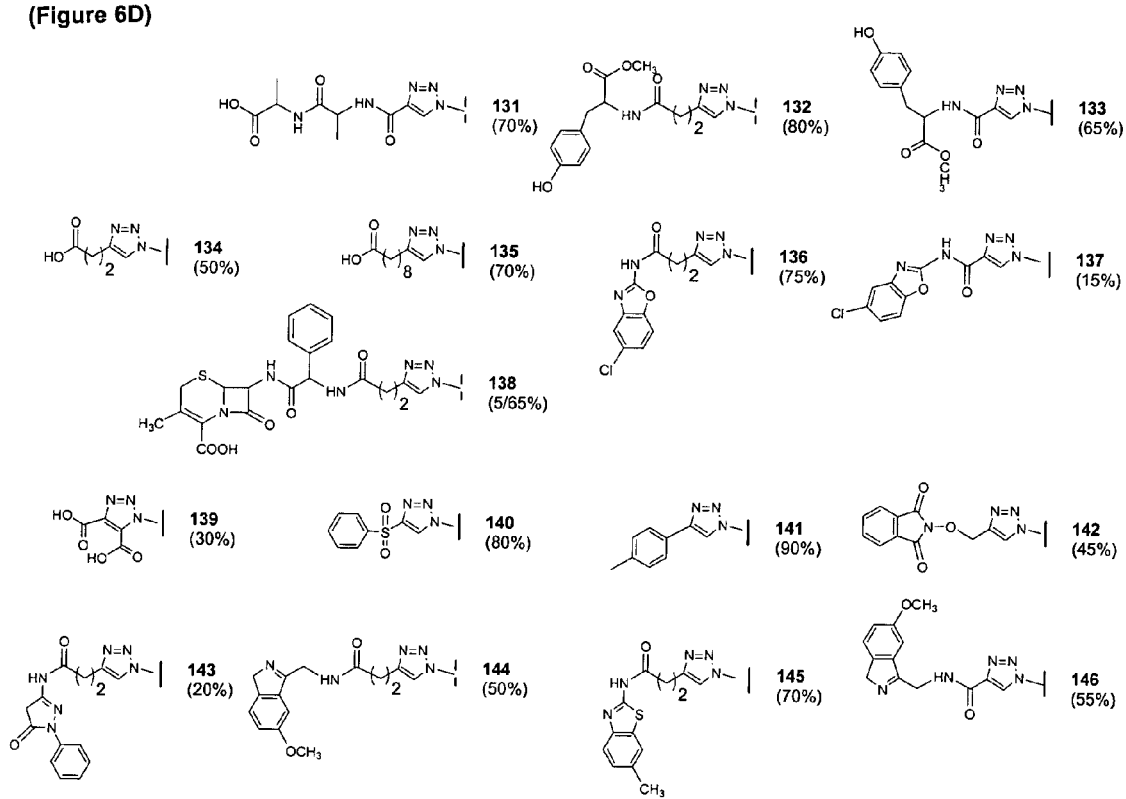

A) UDP-2-azido-, 6-azido- and 6-amino-glucose:
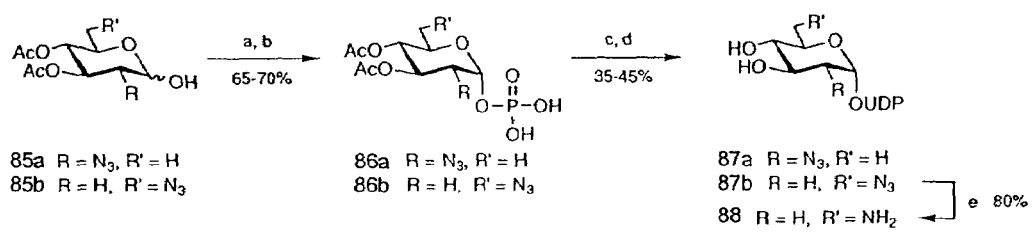
B) UDP-6-chloro-, 2-fluoro-, and 2-amino-glucose:
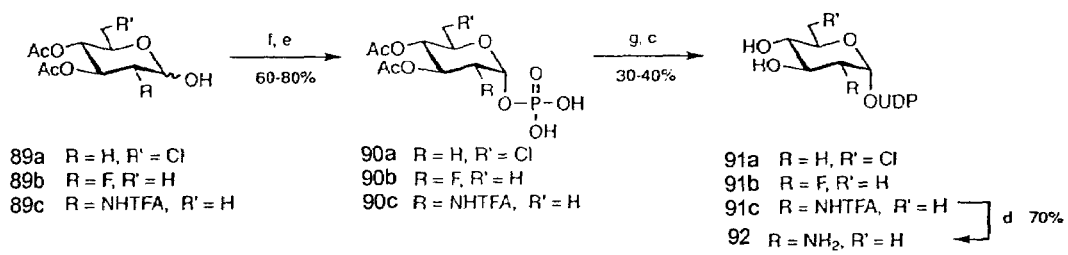
Figure 9

GLYCORANDOMIZATION AND PRODUCTION OF NOVEL VANCOMYCIN ANALOGS

RELATED APPLICATIONS

The present application claims the benefit of U.S. Provisional 60/413,520, 60/413,393 and 60/413,376, filed on Sep. 25, 2002 and is a continuation-in-part of U.S. application Ser. No. 10/109,672, filed Apr. 1, 2002, now U.S. Pat. No. 6,884,604, which claims the benefit of U.S. Provisional Application No. 60/279,682, filed Mar. 30, 2001, all of which are incorporated herein in their entirety for all purposes.

STATEMENT RELATED TO FEDERAL SPONSORED RESEARCH

The present application was supported in part by grants from the National Cancer Institute (NCI Core grant 08748), National Institute of Health (GM58196, CA84374 and A152218). The federal government may have certain rights in this invention.

FIELD OF INVENTION

The present invention is directed to glycosyltransferases and methods for their use. The present invention is also directed to methods of synthesizing novel glycosylated compounds.

BACKGROUND OF THE INVENTION

A recent estimate suggests roughly 70% of current lead compounds in modern drug discovery derive directly from the natural products, many of which are glycosylated bacterial metabolites. Potier, P. Actual. Chim. 11: 9 (1999). Thus, bacterial glycosyltransferases and their corresponding sugar substrates contribute significantly to the diversity of pharmaceutically important metabolites. A glycosylated metabolite is one that is comprised of both a central core structure (often called the "aglycon") and various sugar (or "glycosyl") attachments.

Carbohydrates are able to exhibit target specificity and often the affinity of carbohydrate ligands for their target are defined by the structure and length of the sugar chain carried by the aglycon. Traditionally, carbohydrate ligands of bioactive agents have been implicated in the control of drug pharmacokinetics such as absorption, distribution, metabolism and/or excretion. However, recent growing evidence has led to a change in this dogmatic view.

Pyran (or furan) ring rigidity in conjunction with glycosidic bond flexibility lends itself to preorganization while deoxygenated and/or functionalized sugars also provide unusual hydrophobic and hydrophilic domains. Furthermore, there exist many examples in which removal of these critical ligands leaves barren aglycons with little or no biological activity. Thus, carbohydrates provide great functional diversity to secondary metabolite activity. Thorson, J. S. et al. "Nature's Carbohydrate Chemists: The Enzymatic Glycosylation of Bioactive Bacterial Metabolites," Curr. Org. Chem. 5: 139-167 (2001); Weymouth-Wilson, A. C. "The Role of Carbohydrates in Biologically Active Natural Products," Nat. Prod. Rep. 14: 99-110 (1997).

Carbohydrate ligands often determine the specificity and affinity with which bioactive metabolites bind to DNA. One of the best characterized glycoconjugates is calicheamicin $?_1^1$ (FIG. 1, 1), a member of the enediyne family of antitumor antibiotics isolated from *Micromonospora echinospora*. Thorson, J. S. et al "Enediyne Biosynthesis and Self Resistance: A Progress Report," Bioorgan. Chem. 27: 172-188 (1999) and references therein; Thorson, J. S. et al. "Understanding and Exploiting Nature's Chemical Arsenal: The Past, Present and Future of Calicheamicin Research," Curr. Pharm. Des. 6: 1841-1879 (2000) and references therein. The aryltetrasaccharide of calicheamicin defines both the DNA binding specificity and the high affinity (estimated to be $10^6$-$10^8$) of calicheamicin.

In the related enediyne neocarzinostatin (FIG. 1, 2), the carbohydrate ligand is 2,6-dideoxy-2-methylamino-a-D-galacto-hexopy-ranose (2-N-methyl-a-D-fucosamine) and, in contrast to most minor groove-binding aminoglycosyl ligands, the neocarzinostatin pyranose acts as an anchor, through numerous intermolecular contacts, and defines how deep neocarzinostatin can penetrate the major groove. This locks the molecule into position and thus, ultimately defines the specific sites of DNA-cleavage as well as enhances (possibly as an internal base) the efficiency of cleavage. Stassinopoulos, A. et al. "Solution Structure of a Two-Base DNA Bulge Complexed with an Enediyne Cleaving Analog," Science 272: 1943-1946 (1996); Myers, A. G. et al. "A Comparison of DNA Cleavage by Neocarzinostatin Chromophore and Its Aglycon: Evaluating the Role of the Carbohydrate Residue," J. Am. Chem. Soc. 119: 2965-2972 (1997).

Like the sugar ligands of calicheamicin $?_1^1$ and neocarzinostatin, the carbohydrate ligands of anthracyclines (e.g. daunorubicin, 5, among the most potent and widely used anticancer agents) are known to contribute directly to DNA binding, via intermolecular contacts, and to retard the activity of polymerases in some cases. Also, a direct correlation between increased glycosylation and lower toxicity has been demonstrated. Kirschning, A. et al. "Chemical and Biochemical Aspects of Dexoysugars and Deoxysugar Oligosaccharides," Top. Curr. Chem. 188: 1-84 (1997). Similar roles for the carbohydrates in DNA minor groove binding of the pluramycin antitumor antibiotics (e.g. altromycin B, a DNA alkylator, FIG. 1, 3), the antimicrobial aureolic acids (e.g. chromomycin $A_3$, an inhibitor of replication/translation, FIG. 1, 8), and various other angucyclines, have been observed. Hansen, M. et al. "Threads the DNA Helix Interacting with Both the Major and Minor Grooves to Position Itself for Site-Directed Alkylation of Guanine N7," J. Am. Chem. Soc. 117: 2421-2429 (1995); Pavlopoulos, S. et al. "Structural Characterization of the 1:1 Adduct Formed between the Antitumor Antibiotic Hedamycin and the Oligonucleotide Duplex d(CACGTG)2 by 2D NMR Spectroscopy." Biochem. 35: 9314-9324 (1996); Pavlopoulos, S. et al. "Characterization of the Sequential Non-covalent and Covalent Interactions of the Antitumor Antibiotic Hedamycin with Double Stranded DNA by NMR Spectroscopy," J. Mol. Recognition 12: 346-354 (1999); Johnson, D. A. et al. "Mechanisms and Pathways from Recent Deoxysugar Biosynthesis Research," Curr. Opin. Chem. Biol. 2: 642-649 (1998); Keniry, M. A. et al "The Three-Dimensional Structure of the 4:1 Mithramycin:d(ACCCGGGT)2 Complex: Evidence for an Interaction between the E Saccharides," Biopolymers 54: 104-114 (2000).

Saccharides of secondary metabolites are also responsible for interaction with RNA. Examples include the orthosomycins such as the antibiotic evernimicin (FIG. 1, 11), which specifically binds to the 50S ribosomal subunits of *E. coli* and *S. aureus* and ultimately inhibits protein synthesis. McNicholas, P. M. et al "Evernimicin Binds Exclusively to the 50S Ribosomal Subunit and Inhibits Translation in Cell-Free Systems Derived from both Gram-Positive and Gram-Negative Bacteria," Antimicrob. Agents & Chemotherapy 44: 1121-1126 (2000).

Other examples include the macrolides (described further herein), such as erythromycin D (FIG. 2b, 18), which generally inhibit protein synthesis by inhibiting the 50S ribosome via carbohydrate ligand-mediated binding with the 23S ribosomal subunit and various proteins. Fish, S. A. et al. "Structure-Activity Studies of Tylosin-related Macrolides," J. Antibiot. 49: 1044-1048 (1996). Extensive work has established the critical importance of the macrolide carbohydrate ligands in bioactivity. Kurihara, K. et al. "Analogues of Sixteen-Membered Macrolide Antibiotics. I. Synthesis of 4-O-Alkyl-L-cladinose Analogues via Glycosylation," J. Antibiot. 49: 582-592 (1996). Likewise, the classical aminoglycosides, (e.g. streptomycin, FIG. 1, 6) interact with the small (30S) subunit of eubacteria-type ribosomes which generally leads to translational misreading.

Carbohydrate ligands also play a role in metabolites which interact with cell walls/membranes. For example, the non-ribosomal peptide antibiotic vancomycin (FIG. 1, 7) kills cells by binding to the N-acyl-D-Ala-D-Ala termini of uncrosslinked lipid-PP-disaccharide-pentape-peptides. Goldman, R. C. et al., Curr. Med. Chem. 7: 801 (2000). While it is known that the carbohydrate portion of vancomycin is not directly involved in this binding event, deglycosylation or N-alkylation of the terminal vancosamine sugar of vancomycin shows remarkably different antibacterial profiles, while analogs with synthetically modified carbohydrates were found to operate via a mechanism distinct from that of vancomycin. Solenberg, P. J. et al. "Production of Hybrid Glycopeptide Antibiotics in vitro and in *Streptomyces toyocaensis*," Chem. Biol. 4: 195-202 (1997); Ge, M. et al. "Reconstruction of Vancomycin by Chemical Glycosylation of the Pseudoaglycon," J. Am. Chem. Soc. 120: 11014-11015 (1998); Thompson, C. et al "Synthesis of Vancomycin from the Aglycon," J. Am. Chem. Soc. 121: 1237 (1999); Ge, M. et al. "Vancomycin Derivatives that Inhibit Peptidoglycan Biosynthesis without Binding D-Ala-D-Ala," Science 284: 507-511(1999).

As another example, the polyenes, such as amphotericin B (FIG. 1, 9), bind selectively to ergosterol in the cell membrane of susceptible fungi, inducing changes in permeability that ultimately lead to cell death. Georgopapadakou, N. H., "Antifungals: Mechanism of Action and Resistance, Established and Novel Drugs," Curr. Opin. Microbiol. 1: 547-557 (1998); Abusalah, K. M., Brit. J. Biomed. Sci. 53: 122 (1996). In the amphotericin B-cholesterol aggregate cylindrical complex in the plasma membrane, critical hydrogen-bonding contacts between the polyene sugar and sterol contribute specificity for ergosterol over cholesterol.

Carbohydrate ligands often influence or determine interactions between bioactive metabolites and proteins. In this regard, the indolocarbazoles are an interesting class of metabolite. Prudhomme, M., Curr. Pharm. Des. 3: 265 (1997); Qu, X. G. et al. "A DNA Binding Indolocarbazole Disaccharide Derivative Remains Highly Cytotoxic without Inhibiting Topoisomerase I," Anti-Cancer Drug Des. 14: 433-442 (1999); Bailly, C. et al. "Enhanced Binding to DNA and Topoisomerase I Inhibition by an Analog of the Antitumor Antibiotic Rebeccamycin Containing an Amino Sugar Residue," Mol. Pharmacol. 55: 377-385 (1999); Bailly, C. et al. "Recognition of Specific Sequences in DNA by a Topoisomerase I Inhibitor Derived from the Antitumor Drug Rebeccamycin," Mol. Pharmacol. 53: 77-87 (1998); Goossens, J. F. et al. "Cellular Uptake and Interaction with Purified Membranes of Rebeccamycin Derivatives," Eur. J. Pharmacol. 389: 141-146 (2000). The indolocarbazoles, can be subdivided into two subgroups depending on the nature of the linkage between the carbohydrate residue and the heterocyclic chromophore. Compounds with the sugar attached to the two indole nitrogens (e.g. staurosporine, FIG. 1, 12) have little or no interaction with nucleic acids but strongly inhibit different protein kinases. In contrast, the second subgroup consists of indolocarbazole derivatives in which the carbohydrate moiety is attached to only one indole nitrogen, (e.g. rebeccamycin, 10) which does not inhibit PKC but instead its activity is attributed to the ability to induce topoisomerase-I-dependent DNA-strand breaks. These incredibly different activities attest to the critical role of the saccharide ligand.

As another example, novobiocin (FIG. 1, 4, discussed further herein) is a naturally-occurring coumarin which targets DNA gyrase, the bacterial type II topoisomerase which can introduce negative supercoils into DNA using the free energy of ATP hydrolysis. Structural analyses reveal a significant overlap of the novobiocin sugar constituent and the binding site of the ATP adenine ring. Kampranis, S. C. et al. "Probing the Binding of Coumarins and Cyclothialidines to DNA Gyrase," Biochem. 28: 1967-1976 (1999).

Macrolide antibiotics and coumarin antibiotics are clinically important examples of biologically active glycosylated secondary metabolites. The macrolides are a critical group of compounds due to their potent activity against Gram-positive bacteria. These compounds are generally classified by ring size of the aglycon lactone which contains either 12, 14, or 16 residues. Of these, the 14-membered ring and 16-membered ring families have been extensively studied from which erythromycin $A_1$, oleandromycin, spiramycin, josamycin and midecamycin are used clinically. In general, these metabolites inhibit protein synthesis by inhibiting the 50S ribosome via specific binding with the 23S ribosomal subunit and various proteins. Fish, S. A. et al. (1996).

The 16-member macrolides are generally found to bind 23S rRNA and inhibit peptidyltransferase activity while the 14-member macrolides generally inhibit the translocation of peptidyl-tRNA. Extensive work has established the critical importance of the carbohydrate ligands in bioactivity. Weymouth-Wilson, A. C. (1997); Kurihara, K. et al. (1996); Bertho, G. et al. "Conformational Analysis of Ketolide, Conformations of RU 004 in Solution and Bound to Bacterial Ribosomes," J. Med. Chem. 41: 3373-3386 (1998); Bertho, G. et al. "Solution Conformation of Methylated Macrolide Antibiotics Roxithromycin and Erythromycin Using NMR and Molecular Modeling. Ribosome-bound Conformation Determined by TRNOE and Formation of Cytochrome P450-metbolite Complex," Internatl. J. Biol. Macromol. 22: 103-127 (1998); Bertho, G. et al. "Transferred Nuclear Overhauser Effect Study of Macrolide-Ribosome Interactions: Correlation between Antibiotic Activities and Bound Conformations," Biorg. & Med. Chem. 6: 209-221 (1998); Gharbi-Benarous, J. et al. J. Chem. Soc. Per. Trans. II 529 (1999); Verdier, L. et al. Biorgan. & Med. Chem. 8: 1225 (2000).

Katz and coworkers have demonstrated the biosynthesis of the megalomicins (e.g. FIG. 2, 19) proceeds from erythronolide B (16) in a stepwise manner (FIG. 2b) and interestingly, the conversion of erythromycin D (18) to megalomycin A (19), via oxidation and the addition of a single sugar 2,3,4,6-tetradeoxy-3-dimethylamino-β-D-threo-hexopyranose (megosamine), changes the molecule's activity from an antibiotic (erythromycin D) to an antiparasitic/antiviral agent (megalomycin A). Volchegursky, Y. et al. "Biosynthesis of the Anti-Parasitic Agent Megalomicin: Transformation of Erythromycin to Megalomicin in *Saccharopolyspora erythraea*," Mol. Microbiol. 37: 752-762 (2000).

Novobiocin (FIG. 1, 4) is a naturally-occurring coumarin from *Streptomyces spheroides* which targets DNA gyrase. DNA gyrase from *E. coli* is an $A_2B_2$ complex in which each polypeptide displays distinct functional domains and the coumarins specifically inhibit the ATPase reaction of GyrB in a competitive manner. The complexes of the 24 kDa GyrB fragment with novobiocin and a related coumarin, chlorbiocin, show the binding sites for ATP and coumarins partially overlap. Tsai, F. T. F et al. Proteins 28: 41 (1997); Lewis, R. J. et al. EMBO J. 15: 1412 (1996). In particular, these high resolution structures reveal a significant overlap of the drug sugar constituent (3-O-aminocarbonyl)-6-deoxy-5-C-methyl-4-O-methyl-β-D-lyxo-hexopyranose, also known as β-D-noviose, in novobiocin) and the binding site of the ATP adenine ring with specific sugar-protein hydrogen-bonding interactions between the sugar C-2 and Asn 46, the sugar C-3 amide carbonyl with Thr 165 and amine with Asp 73/Val 43 main chain atoms. Site directed mutagenesis of these GyrB amino acids supports the structural assignments. Kampranis, S. C. et al. Biochem. 28: 1967 (1999). Interestingly, while these interactions are critical, the replacement of D-noviose with L-rhamnose has recently provided analogs with similar activity and potency. Ferroud, D. et al. Biorgan. & Med. Chem. Lett. 9: 2881 (1999). Furthermore, replacement of the C-3 acylamino substituent with reversed isosteres also provided highly potent analogs. Laurin, P. et al. Biorgan. & Med. Chem. Lett. 9: 2079 (1999). Recent studies also demonstrate a unique interaction of novobiocin with heat shock protein 90 (Hsp90), which shares homology with the a typical ATP-binding domaining of *E. coli* GyrB and stabilizes several oncogenic protein kinases. Marcu, M. G. J. Nat. Cancer Inst. 92: 242 (2000).

The gene cluster from *S. spheroides* which encodes for novobiocin biosynthesis and self resistance was recently cloned and a single glycosyltransferase gene (novM, accession AAF67506) was identified. Steffensky, M. et al. Antimicrob. Agents Chemotherap. 44: 1214 (2000). Given novobiocin contains a single saccharide, it is presumed novM encodes for the transfer of D-noviose from the activated dTDP-D-noviose to the aglycon novobiocic acid (FIG. 4, 20). The coumarins, while much more potent inhibitors of DNA gyrase in vitro than the clinically utilized quinolones, have failed clinically due to poor cell penetration, low solubility and toxicity in eukaryotes (perhaps due to this Hsp90 interaction). Thus, as an example of an area where engineering of secondary metabolites will be useful, glycosylated metabolites based on the coumarin aglycon but having altered carbohydrate moities may produce clinically useful compounds.

Both glycosyltransferases and nucleotidyltransferases play critical roles in the formation of glycosylated secondary metabolites. The first step in metabolite glycosylation is the reversible conversion of an a-D-hexose-1-phosphate to the corresponding nucleotide diphospho (NDP) hexose. Enzymes that catalyze this type of reaction (known as a-D-hexose-1-phosphate nucleotidyltransferases) are prevalent in nature and, regardless of their origins, are generally allosterically controlled with catalysis proceeding via an ordered bi-bi mechanism. Liu, H. -w. et al. "Pathways and Mechanisms in the Biogenesis of Novel Deoxysugars by Bacteria," Annu. Rev. Microbiol. 48: 223-256 (1994).

The culminating attachment of a carbohydrate to a secondary metabolite aglycon (or growing saccharide chain) is catalyzed by the family of enzymes known as glycosyltransferases. These enzymes transfer a sugar, from its activated form (a nucleotide diphospho-sugar or NDP-sugar), to an acceptor nucleophile to form a glycosidic bond and NDP. These enzymes can catalyze transfer with retention (with respect to the NDP-sugar) or inversion of anomeric stereochemistry. Drawing from the glycosidase analogy, the current belief is "retaining" glycosyltransferases proceed via a double displacement mechanism, which utilizes an enzyme-glycoside covalent intermediate, while the "inverting" transferases proceed via a single displacement mechanism. Sinnott, M. L. "Mechanisms of Glycosyl Hydrolysis and Transfer," Chem. Rev. 90: 1171-1202-1265 (1990). Based upon the known glycosylated metabolites, the majority of glycosyltransferases in secondary metabolism are "inverting" enzymes and the acceptor nucleophile is most often an aglycon or carbohydrate-derived heteroatom (O, N or S).

There are currently more than 70 putative secondary metabolite glycosyltransferase genes in the public database and these can be divided into three major families based upon sequence alignments. Thorson J. S. et al. (2001). Class I is the largest family and contains glycosyltransferases from both aromatic and macrolide metabolite pathways, Class II is predominately comprised of transferases associated with non-ribosomal peptides and glycolipids, while the majority of Class III enzymes are involved in metabolite inactivation. The number of known and putative secondary metabolite glycosyltransferase genes in the public database is growing rapidly, as this is an active area of research.

A number of genetic in vivo experiments have demonstrated that the glycosyltransferases of secondary metabolism (which include those for anthracyclines, angucyclines, nonribosomal peptides, macrolides and enediynes) are promiscuous with respect to the NDP-sugar donor. Thorson J. S. et al. (2001); Hutchinson, C. R. "Combinatorial Biosynthesis for New Drug Discovery," Curr. Opin. Microbiol. 1: 319-329 (1998). While these in vivo experiments have provided novel metabolites, the newly formed metabolites, in most cases, were inactivated via host-catalyzed modification to prevent killing the host producing organism. Thus, in biosynthetically altering glycosylation, an in vitro scheme is desirable to eliminate this interference by host inactivation mechanisms.

The glycosyltransferases of secondary metabolism rely almost exclusively upon pyrimidine (uridine or thymidine) diphosphosugars, yet, in vitro studies in this area are severely lacking due to the inability to access the appropriate NDP-sugar substrates. Easy access to UDP- or dTDP-sugars would revolutionize the biochemical characterization and exploitation of these critical glycosyltransferases.

Surprisingly, a three dimensional structure for any enzyme from this important class of enzymes is lacking and of the many nucleotidyltransferases studied, the dTDP-a-D-glucose forming thymidylyltransferases have received the least attention. The best characterized thymidylyltransferase (rm1A-encoded $E_p$) is from *Salmonella*, which catalyzes the reaction shown in FIG. 2*a*. Lindquist, L. et al. "Purification, Characterization and HPLC Assay of *Salmonella* Glucose-1-phosphate Thymidylyltransferase from the Cloned rfbA Gene," Eur. J. Biochem. 211: 763-770 (1993). Preliminary $E_p$ substrate specificity studies, limited to only a few commercially available hexopyranosyl phosphates and NTPs, revealed $E_p$ could utilize both dTTP and UTP as well as a-D-glucosamine-1-phosphate as a substitute for natural substrate (a-D-glucose-1-phosphate). Kinetic analysis revealed a ping-pong mechanism with K.sub.m values for the forward direction for dTTP and a-D-glucose-1-phosphate of 0.02 mM and 0.11 mM, respectively. In the reverse reaction the $K_m$ values for dTDP-a-D-glucose and diphosphate were 0.083 mM and 0.15 mM, respectively. Lindquist, L. et al. (1993).

The above examples illustrate that carbohydrate ligands often define the biological activity of a particular secondary metabolite and suggest alteration of saccharide ligands should lead to new compounds which may display novel biological activity. However, the complex structure of most glycosylated natural products preclude the ability to synthetically exchange their sugar ligands.

Further, while in vivo experiments have provided novel metabolites, the newly formed metabolites, in most cases, were inactivated via host-catalyzed modification to prevent killing the host producing organism. As the organisms producing the novel metabolites are killed, it is not feasible to produce sufficient amounts of novel metabolites for analysis or therapeutic use in in vivo systems. Additionally, producing novel metabolites in vivo requires the use of recombinant DNA technology to alter gene expression. Such methods are too time consuming for rapid production of numerous novel metabolites for testing as drug candidates. Further still, the production of these new agents was also severely limited by the host's biosynthetic machinery so that the number and diversity of compounds that may be produced by such methods is likewise severely limited.

Thus, for biosynthetically altering glycosylation, an in vitro scheme is needed to eliminate the problems associated with in vivo manipulation. Further, a scheme that allows such manipulation despite the complexities of biologically active secondary metabolites is needed.

SUMMARY OF THE INVENTION

The present invention provides combinatorial methods for rapidly generating a diverse library of glycorandomized structures, comprising incubating one or more aglycons and a pool of NDP-sugars in the presence of a glycosyltransferase. The glycosyltransferase may be one that is associated with or involved in production of natural secondary metabolites, or one which is putatively associated with or involved in production of natural secondary metabolites. The glycosyltransferase may show significant flexibility with respect to its NDP-sugar donors and/or its aglycons. NDP-sugar donors may be commercially available, or may be produced by utilizing mutant or wild type nucleotidyltransferases significant flexibility with respect to their substrates.

The present invention provides a novel method of chemo-enzymatic synthesis of glycosylated entities. The present invention provides a simple and efficient method to bypass the severe barriers to synthesis posed by both the complexities of biologically active secondary metabolites and the difficulties and limitations of in vivo manipulation, for the first time providing the ability to construct large libraries of diverse macrolides with varied carbohydrate attachments as therapeutic candidates and for use in, e.g., biomedical processes, production of downstream compounds, and biomedical and chemical research.

The present invention enables the rapid synthesis of compounds (typically based upon natural products) too complex for chemical synthesis but not accessible by biosynthesis.

The present invention enables the rapid generation of libraries of novel chemical entities not available through synthesis or biosynthesis. Since these compounds are generally based on biologically active natural products and the carbohydrate ligands being randomized are generally critical to this activity, the potential for compounds with novel activities is great.

The present invention provides methods of glycorandomization and methods for producing novel compounds through the use of glycorandomization.

The present invention provides methods for producing novel glycosylated entities. The present invention provides chemo-enzymatic methods for altering any given glycosylated entity or entity capable of being glycosylated to produce novel entities. In a preferred embodiment of the present invention, novel entities with enhanced or unique biological activities are produced. Entities which may be altered include, but are not limited to, natural and synthetic aglycons, natural product metabolites, enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones coumarins, polyketides, pluramycins, aminoglycosides, oligosaccharides, peptides, proteins, numerous other classes of bioactive compounds, and hybrids consisting of one or more these components.

In one embodiment, a method of the present invention comprises incubating a pool of entities capable of being glycosylated with a glycosyltransferase (which may also be referred to herein as glycosyltransferases) and a pool of nucleotidyl sugars to produce a glycosylated entity.

In certain embodiments, the pool of sugars consists of a single sugar. In other embodiments, the pool of sugars comprises different sugars. In one such embodiment, the pool of sugars comprises a population of sugars that is highly diverse. In certain embodiments, the pool of sugars comprises known nucleotidyl sugars and/or novel nucleotidyl sugars.

In certain embodiments, the pool of NDP-sugar donors comprises naturally occurring sugars. In certain embodiments, the pool of NDP-sugar donors comprises novel or "unnatural" sugars. In certain embodiments the pool of NDP-sugar donors comprises or is selected from a library or libraries of NDP-sugars catalyzed by utilizing the promiscuity of wild type and/or engineered *Salmonella enterica* LT2 a-D-glucopyranosyl phosphate thymidylyltransferase (Ep).

In certain embodiments, at least one of the at least one nucleotide sugar is selected from the group consisting of Uridine 5'-(a-D-allopyranosyl diphosphate); Uridine 5'-(a-D-altropyra-nosyl diphosphate); Thymidine 5'-(a-D-gulopyranosyl diphosphate); Uridine 5'-(a-D-gulopyranosyl diphosphate); Thymidine 5'-(a-D-idopyranosyl diphosphate); Uridine 5'-(a-D-idopyranos-yl diphosphate); Thymidine 5'-(a-D-talopyranosyl diphosphate); Uridine 5'-(a-D-talopyranosyl diphosphate); Thymidine 5'-(6-amino-6-deoxy-a-D-glucopyranosyl diphosphate); Uridine 5'-(6-amino-6-deoxy-a-D-glucopyranosyl diphosphate); Thymidine 5'-(4-amino-4-deoxy-a-D-glucopyranosyl diphosphate); Uridine 5'-(4-amino-4-deoxy-a-D-glucopyranosyl diphosphate); Thymidine 5'-(3-amino-3-deoxy-a-D-glucopyranosyl diphosphate); Uridine 5'-(3-amino-3-deoxy-a-D-glucopyranosyl dipbosphate); Thymidine 5'-(2-amino-2-deoxy-a-D-glucopyranosyl diphosphate); Uridine 5'-(2-amino-2-deoxy-a-D-glucopyranosyl diphosphate); Thymidine 5'-(6-acetamido-6-deoxy-a-D-glucopyranosyl diphosphate); Uridine 5'-(6-acetamido-6-deoxy-a-D-glucopyranosyl diphosphate); Thymidine 5'-(4-acetamido-4-deoxy-a-D-glucopyranosyl diphosphate); Uridine 5'-(4-acetamido-4-deoxy-a-D-glucopyranosyl diphosphate); Thymidine 5'-(3-acetamido-3-deoxy-a-D-glucopyranosyl diphosphate); Uridine 5'-(3-acetamido-3-deoxy-a-D-glucopyranosyl diphosphate); Thymidine 5'-(2-acetamido-2-deoxy-a-D-glucopyranosyl diphosphate); Uridine 5'-(2-acetamido-2-deoxy-a-D-glucopyranosyl diphosphate); Thymidine 5'-(4-amino-4,6-dideoxy-a-D-glucopyranosyl diphosphate); Uridine 5'-(4-amino-4,6-dideoxy-a-D-glucopyranosyl diphosphate); Thymidine 5'-(a-D-glucopyran-6-uronic acid diphosphate); Uridine 5'-(a-D-glucopyran-6-uronic acid diphosphate); Thymidine 5'-(a-D-arabinopyranosyl diphosphate); Uridine 5'-(a-D-arabinopyranosyl diphosphate); and -continued

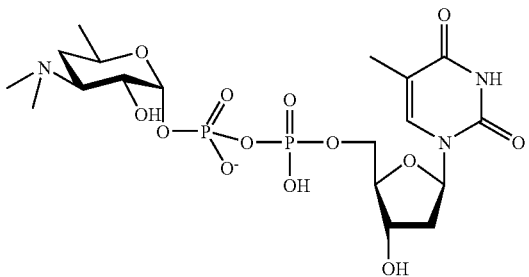

$C_{18}H_{30}N_3O_{13}P_2^-$
Exact Mass: 558.13
Determined: 558.17

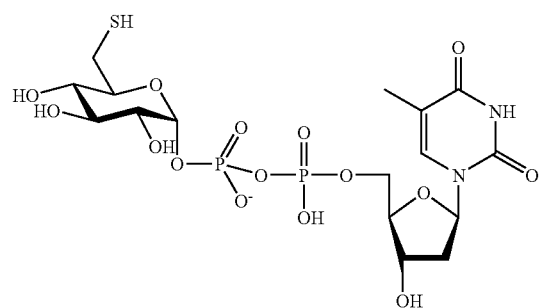

$C_{16}H_{25}N_2O_{15}P_2S^-$
Exact Mass: 579.05
Determined: 579.06

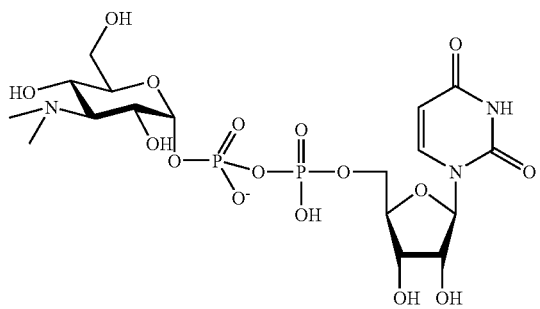

$C_{17}H_{28}N_3O_{16}P_2^-$
Exact Mass: 592.09
Determined: 592.09

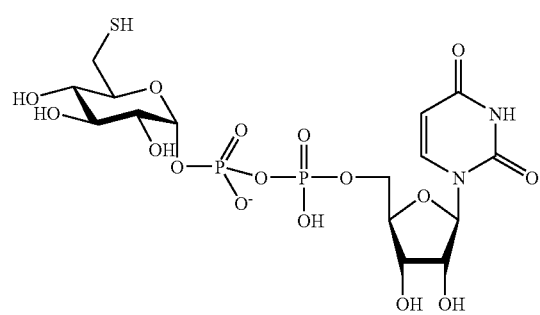

$C_{15}H_{23}N_2O_{16}P_2S^-$

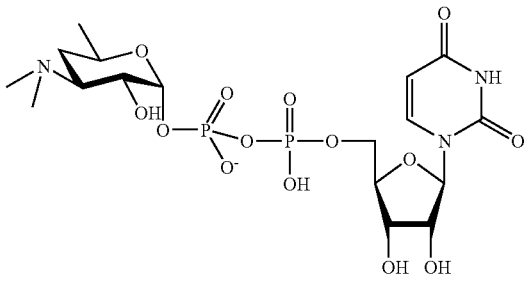

$C_{17}H_{28}N_3O_{14}P_2^-$
Exact Mass: 560.10
Determined: 560.15

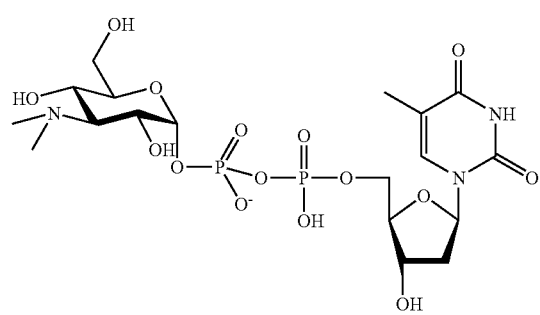

$C_{18}H_{30}N_3O_{15}P_2^-$
Exact Mass: 590.12
Determined: 590.15

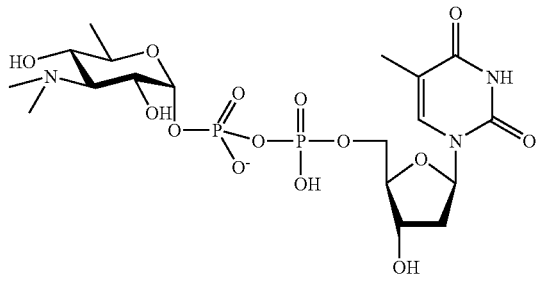

$C_{18}H_{30}N_3O_{14}P_2^-$
Exact Mass: 574.12
Determined: 574.12

-continued

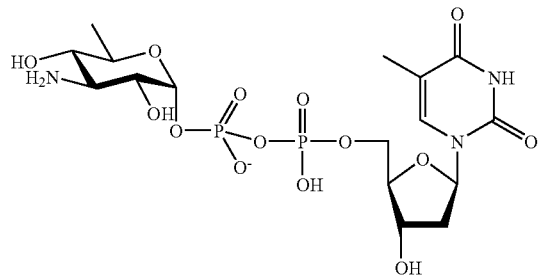

C₁₆H₃₆N₃O₁₄P₂⁻
Exact Mass: 546.09
Determined: 546.05

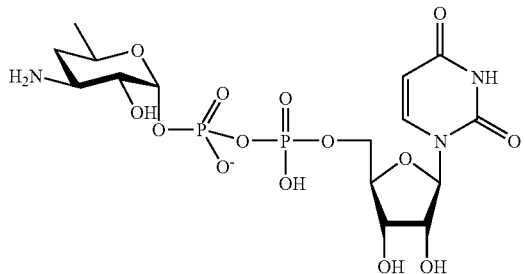

C₁₅H₂₄N₃O₁₄P₂⁻
Exact Mass: 532.07
Determined: 532.10

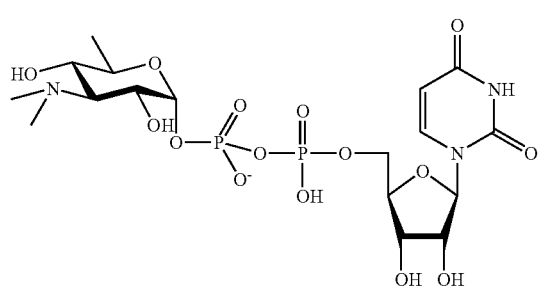

C₁₇H₂₈N₃O₁₅P₂⁻
Exact Mass: 576.10
Determined: 576.03

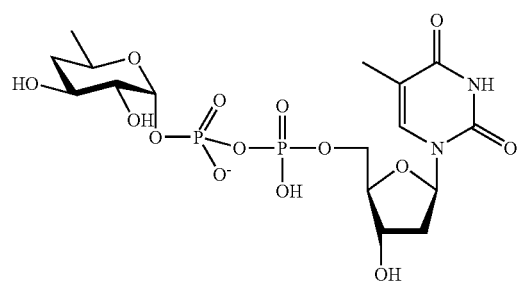

C₁₆H₂₅N₂O₁₄P₂⁻
Exact Mass: 531.08
Determined: 531.07

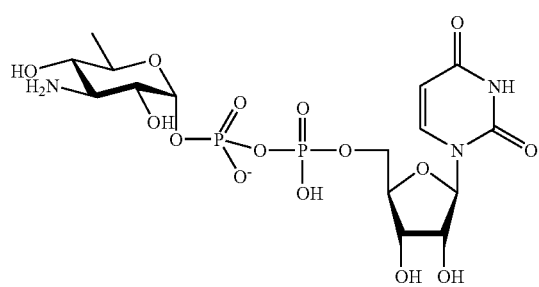

C₁₅H₂₄N₃O₁₅P₂⁻
Exact Mass: 548.07
Determined: 548.13

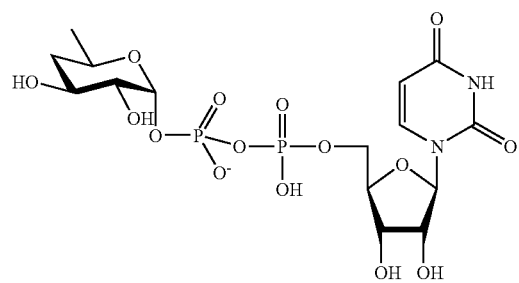

C₁₅H₂₃N₂O₁₅P₂⁻
Exact Mass: 533.06
Determined: 533.09

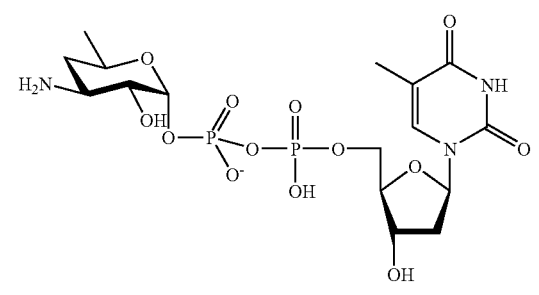

C₁₆H₂₆N₃O₁₃P₂⁻
Exact Mass: 530.09
Determined: 530.04

In certain other embodiments, at least one of the at least one nucleotide sugar is selected from the group consisting of Thymidine 5'-(a-D-glucopyranosyl diphosphate); Uridine 5'-(a-D-glucopyranosyl diphosphate); Thymidine 5'-(2-deoxy-a-D-glucopyranosyl diphosphate); Uridine 5'-(2-deoxy-a-D-glucopyranosyl diphosphate); Thymidine 5'-(3-deoxy-a-D-glucopyranosyl diphosphate); Uridine 5'-(3-deoxy-a-D-glucopyranosyl diphosphate); Thymidine 5'-(4-deoxy-a-D-glucopyranosyl diphosphate); Uridine 5'-(4-deoxy-a-D-glucopyranosyl diphosphate); Thymidine 5'-(6-deoxy-a-D-glucopyranosyl diphosphate); Uridine 5'-(6-deoxy-a-D-glucopyranosyl diphosphate); Thymidine 5'-(a-D-mannopyranosyl diphosphate); Uridine 5'-(a-D-mannopyranosyl diphosphate); Thymidine 5'-(a-D- galactopyranosyl diphosphate); Uridine 5'-(a-D-galactopyranosyl diphosphate); Thymidine 5'-(a-D-allopyranosyl diphosphate); and Thymidine 5'-(a-D-altropyranosyl diphosphate).

The present invention provides a method for producing novel glycosylated compounds comprising: combining at least one moiety capable of being glycosylated and at least one first nucleotide sugar in the presence of at least one first glycosyltransferase, wherein the method is carried out in vitro and at least one novel glycosylated compound is produced.

The present invention provides a method comprising combining (a) at least one moiety capable of being glycosylated and (b) at least one first nucleotide sugar produced by combining nucleotide triphosphate (NTP) and at least one sugar phosphate in the presence of at least one mutated nucleotidyltransferase; in the presence of at least one first glycosyltransferase, wherein at least one glycosylated compound is produced.

In certain embodiments, at least one of the at least one mutated nucleotidyltransferase is $E_p$ mutated at one or more amino acids selected from the group consisting of V173, G147, W224, N112, G175, D111, E162, T201, I200, E199, R195, L89, L89T, L109, Y146 and Y177. In certain embodiments, at least one of the at least one mutated nucleotidyl-transferase is $E_p$ mutated at one or more amino acids in its active site, its divalent cation binding site, and/or its auxiliary site.

Methods according to the present invention are preferably carried out in vitro.

In certain preferred embodiments, at least on of the at least one novel glycosylated compounds produced has enhanced and/or unique biological activity as compared to at least one of the at least one moieties capable of being glycosylated. In certain other preferred embodiments, more than one type of glycosylated compound is produced in a single reaction vessel and at least one of the at least one glycosylated compounds produced is a novel glycosylated compound.

In certain other preferred embodiments, highly diverse population of glycosylated compounds is produced and at least one of the at least one glycosylated compounds produced is a novel glycosylated compound.

In certain embodiments, at least one of the at least one moiety capable of being glycosylated is selected from the group consisting of natural and synthetic metabolites, pyran rings, furan rings, enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones coumarins, polyketides, pluramycins, aminoglycosides, oligosaccharides, peptides, proteins, and hybrids thereof.

In certain other embodiments, at least one of the at least one moiety capable of being glycosylated is selected from the group consisting of aglycons of bioactive anthracyclines, angucyclines, nonribosomal peptides, macrolides, enediynes, indolocarbazoles, pluramycins, aurelolic acids, orthosomycins, aminoglycosides, coumarins, bleomycins, amicetins, polyenes, benzoisochromanequinones, angucyclines, and hybrids thereof.

In certain other embodiments, at least one of the at least one moiety capable of being glycosylated is selected from the group consisting of enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones coumarins, polyketides, pluramycins, aminoglycosides, oligosaccharides, peptides, proteins, and hybrids consisting of one or more these components.

In certain embodiments, at least one of the at least one first glycosyltransferase is selected from the group consisting of CalB, CalE, CalN, CalU, Gra orf14, Gra orf5, LanGT1, LanGT2, LanGT3, LanGT4, MtmGI, MtmGII, MtmGIII, MtmGTIV, NovM, Rh1B, Rif orf 7, SnogD, SnogE, SnogZ, UrdGT1a, UrdGT1b, UrdGT1c, UrdGT2, AknK, AknS, DesVII, DnrS, OleG1, OleG2, TylCV, TylMII, TylN, DauH, DnrH, EryBV, EryCIII, Ngt, BgtA, BgtB, BgtC, GftA, GftB, GftC, GftD, GftE, Gp1-1, Gp1-2, RtfA, AveBI, BlmE, BlmF, MgtA, NysD1, OleD, OleI, SpcF, SpcG, StrH, Ugt51B1, Ugt51C1, UGT52, UgtA, UgtB, UgtC, UgtD and homologs thereof; is selected from the group consisting of those glycosyltransferases known to be involved in the synthesis of bioactive metabolites; or is is produced by expressing the product of a putative glycosyltransferase gene.

In certain embodiments, more than one moiety capable of being glycosylated is incubated with the at least one novel nucleotide sugar in the presence at least one type of glycosyltransferase.

In certain embodiments, at least one moiety capable of being glycosylated is incubated with more than one novel nucleotide sugar in the presence more than one type of glycosyltransferase.

In certain embodiments, at least one moiety capable of being glycosylated is incubated with the at least one novel nucleotide sugar in the presence more than one type of glycosyltransferase.

The present invention also provides a method comprising incubating at least one glycosylated compound produced by the method of claim C that is capable of being glycosylated with and at least one second nucleotide sugar in the presence of at least one second glycosyltransferase to produce at least one twice-glycosylated compound having at least a first and a second glycosyl attachment, wherein the first and second may be of the same type or of different types and the second glycosyl attachment may be attached to the original moiety capable of being glycosylated or to the first glycosyl attachment.

The present invention provides a method comprising subjecting at least one glycosylated compound produced according to the methods of the present invention to repeated cycles of incubation with at least one nucleotide sugar in the presence of at least one glycosyltransferase until a population multiply-glycosylated compounds of the desired type and size is achieved.

The present invention also provides novel compounds produced by the methods of the present invention. Non-limiting examples of the such novel compounds that are provided by the present invention include two novel novobiocin (designated Nov-1 and Nov-2) derivatives and six novel erythromycin (designated Ery-1-Ery-6) analogs.

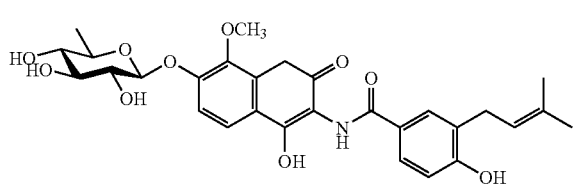

Nov-1

Nov-2

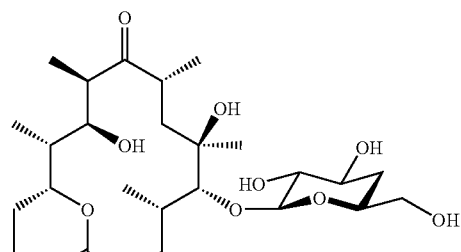

Ery-1

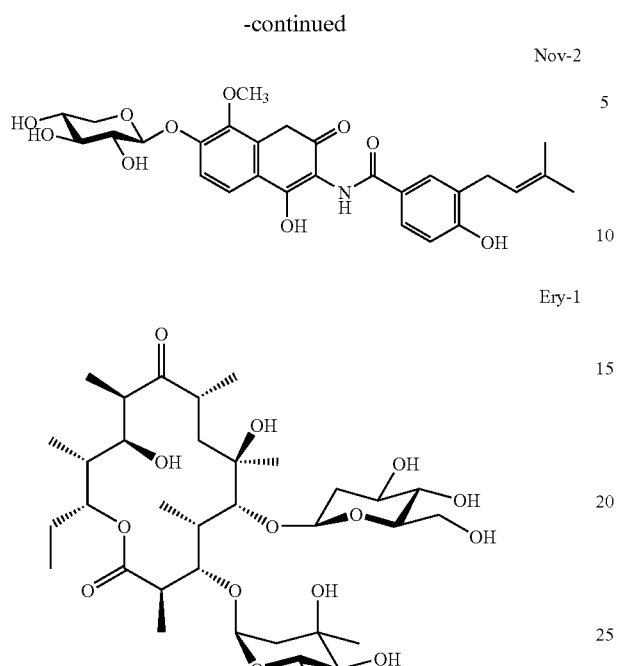

Ery-2

Ery-3

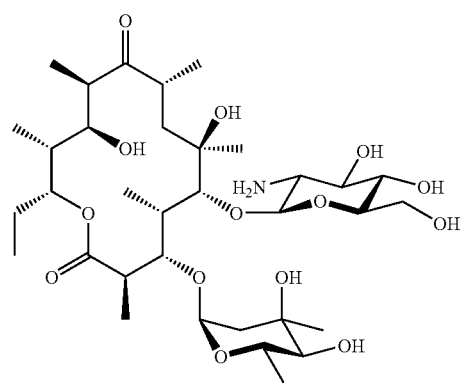

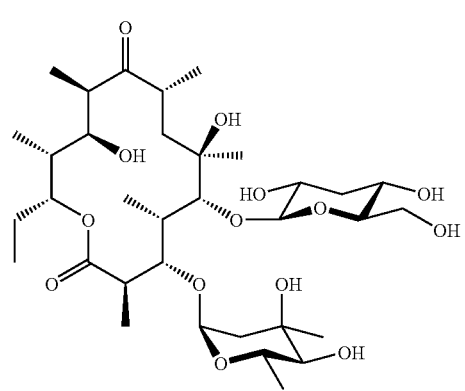

Ery-4

Ery-5

Ery-6

An embodiment of the present invention also provides a novel method of synthesizing new glycosylated compounds. The method comprising incubating at least one moiety capable of being glycosylated and at least one thymidine or uridine nucleotide diphosphosugar in the presence of at least one first glycosyltransferase. In a preferred embodiment, the nucleodiphosphosugar includes a sugar structure that is selected from the group consisting of:

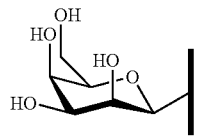

34

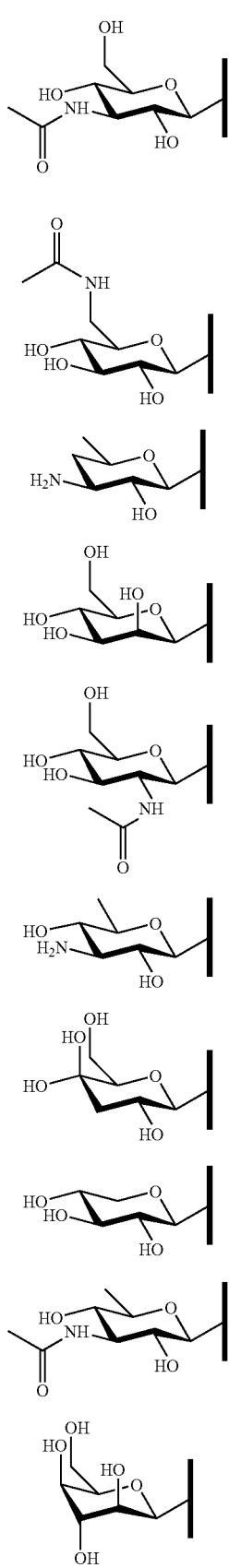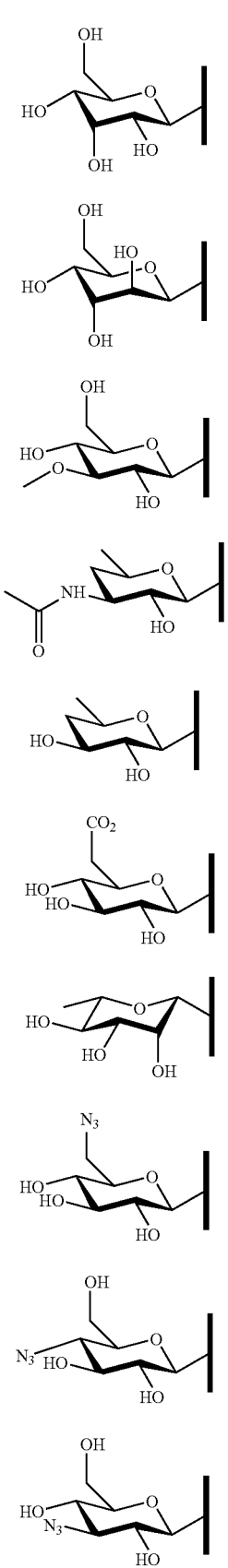

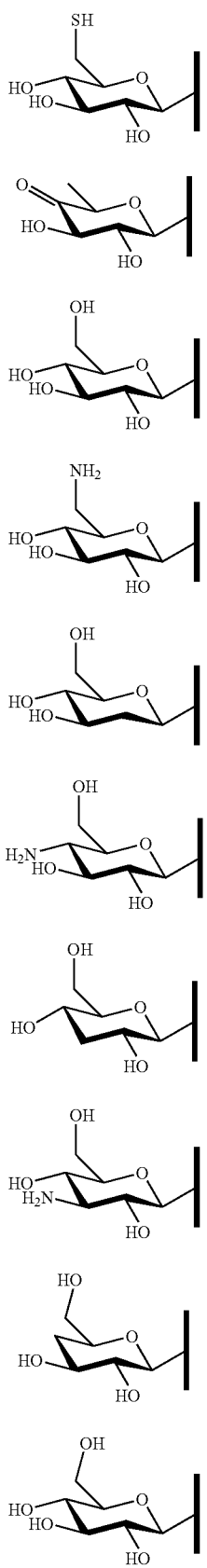
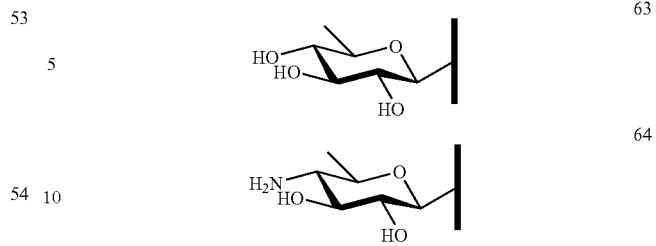

In another preferred embodiment, the incubation is carried out in vitro. Further, the method teaches that more than one nucleotide diphosphosugar may be incubated with at least one moiety capable of being glycosylated in the presence of at least one first glycosyltransferase. The moiety capable of being glycosylated may include natural and synthetic metabolites, pyran rings, furan rings, enediynes, anthracyclines, angucyclines, aureolic acids, orthosomycins, macrolides, aminoglycosides, non-ribosomal peptides, polyenes, steroids, lipids, indolocarbazoles, bleomycins, amicetins, benzoisochromanequinones coumarins, polyketides, pluramycins, aminoglycosides, oligosaccharides, peptides, proteins, hybrids consisting of one or more these components, analogs or bioactive aglycons thereof. Further, the moiety capable of being glycosylated may include vancomycin, teicoplannin, analogs, hybrids, or active aglycons thereof.

In certain embodiments of the present invention, a first glycosyltransferase may include CalB, CalE, CalN, CalU, Gra orf14, Gra orf5, LanGT1, LanGT2, LanGT3, LanGT4, MtmGI, MtmGII, MtmGTIII, MtmGTIV, NovM, RhlB, Rif orf 7, SnogD, SnogE, SnogZ, UrdGT1a, UrdGT1b, UrdGT1c, UrdGT2, AknK, AknS, DesVII, DnrS, OleG1, OleG2, TylCV, TylMII, TylN, DauH, DnrH, EryBV, EryCIII, Ngt, BgtA, BgtB, BgtC, GftA, GftB, GftC, GftD, GftE, Gp1-1, Gp1-2, RtfA, AveBI, BlmE, BlmF, MgtA, NysD1, OleD, OleI, SpcF, SpcG, StrH, Ugt51B1, Ugt51C1, UGT52, UgtA, UgtB, UgtC, UgtD or homologs thereof. In a preferred embodiment, the first glycosyltransferase is GftE.

Yet another embociment of the present invention includes incubating at least one glycosylated compound that is capable of being glycosylated with and at least one second nucleotide diphosphosugar in the presence of at least one second glycosyltransferase to produce at least one twice-glycosylated compound having at least a first and a second glycosyl attachment. In a preferred embodiment the second glycosyltransferase is GftD. In certain embodiments, the first and second glycosyl attachments may be the same, or different. Further the first and the second glycosyl attachments may be both either attached to the moiety capable of being glycosylated or the second glycosyl attachment may be attached to the first glycosyl attachment. In certain other embodiments, the first and second glycosyl transferases may be the same or different.

In yet another preferred embodiment of the present invention, novel synthesis of at least one glycosylated compound includes repeating cycles of incubation with at least one nucleotide diphosphosugar in the presence of at least one glycosyltransferase until a population multiply-glycosylated compounds of the desired type and number of compounds is achieved.

Another method for producing novel glycosylated compound is described in the present invention. The method includes incubating at least one moiety capable of being glycosylated and at least one thymidine or uridine nucleotide diphosphosugar in the presence of at least one first glycosyltransferase, wherein the nucleotide disphosphosugar includes a sugar structure selected from the following group:
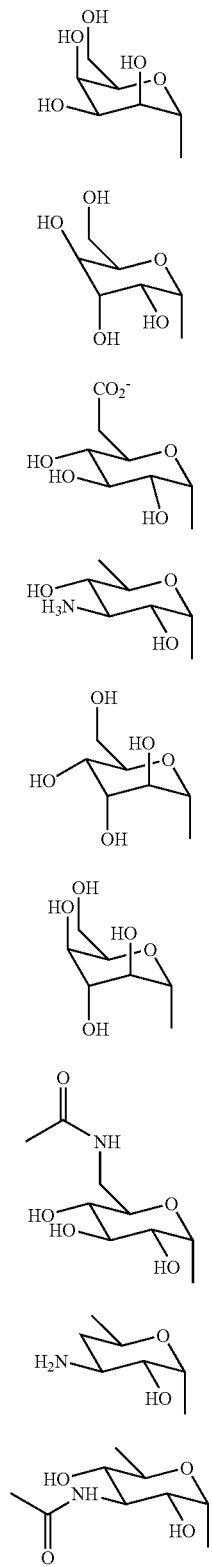
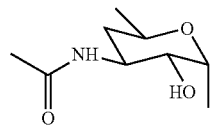
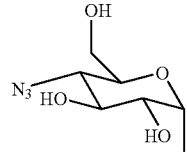
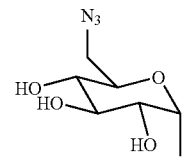
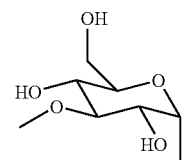
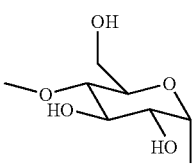
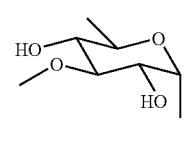
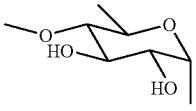
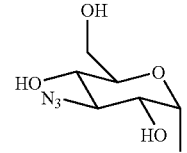
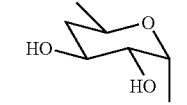
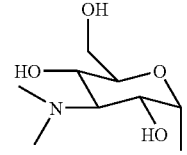
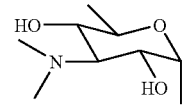

-continued

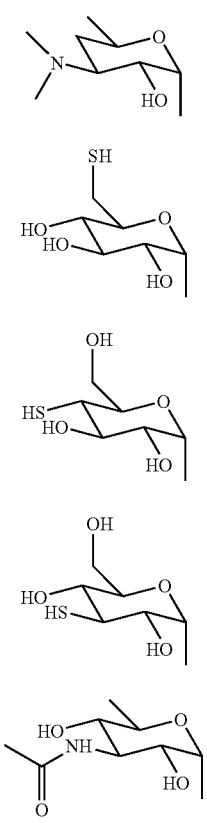

121

122

123

124

125

Further, in certain embodiments, the first glycosyltransferase may be produced by expressing the product of a putative or known glycosyltransferase gene.

Yet another preferred embodiment of the present invention includes a method for synthesizing at least one chemoselectively ligated compound. The method includes incubating at least one chemoselectively ligatable moiety and at least one glycosylated compound. The chemoselectively ligatable moiety includes at least one of the following structures:

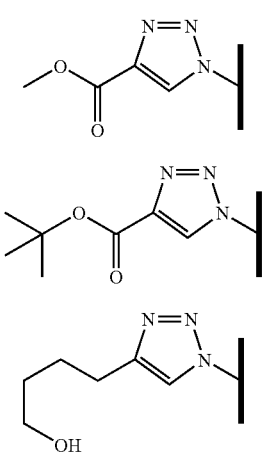

65

66

67

-continued

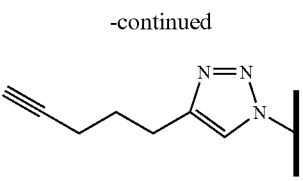

68

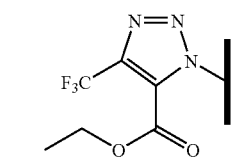

69a

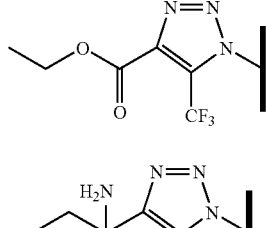

69b

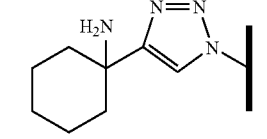

70

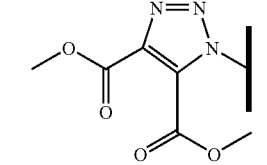

71

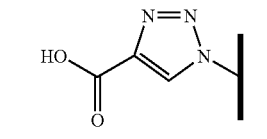

72

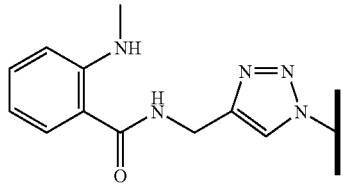

73

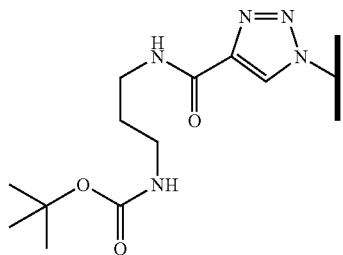

74

-continued
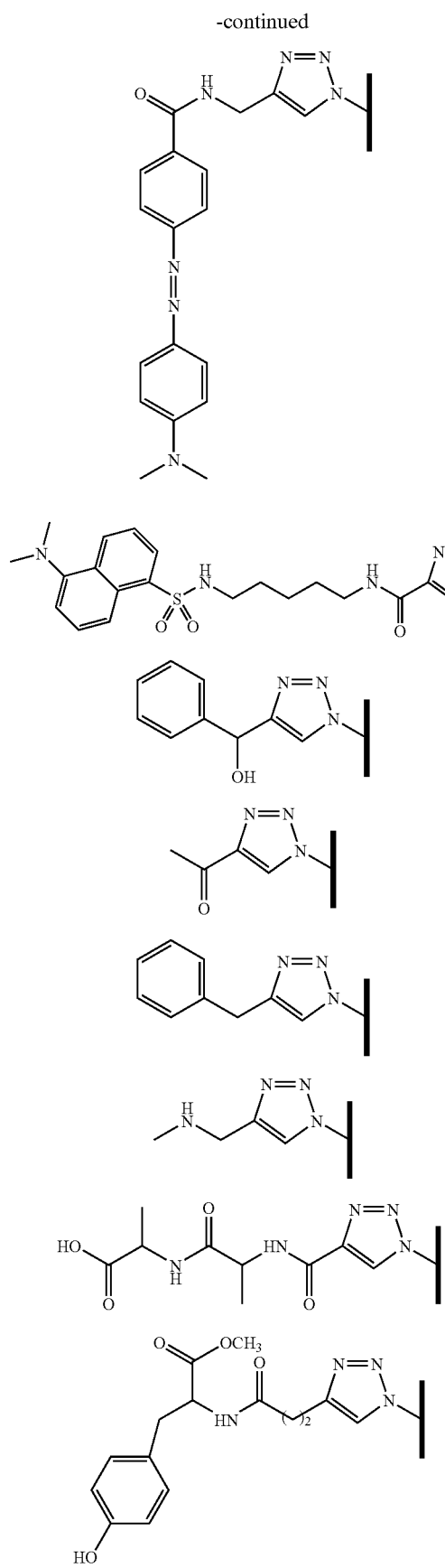
-continued
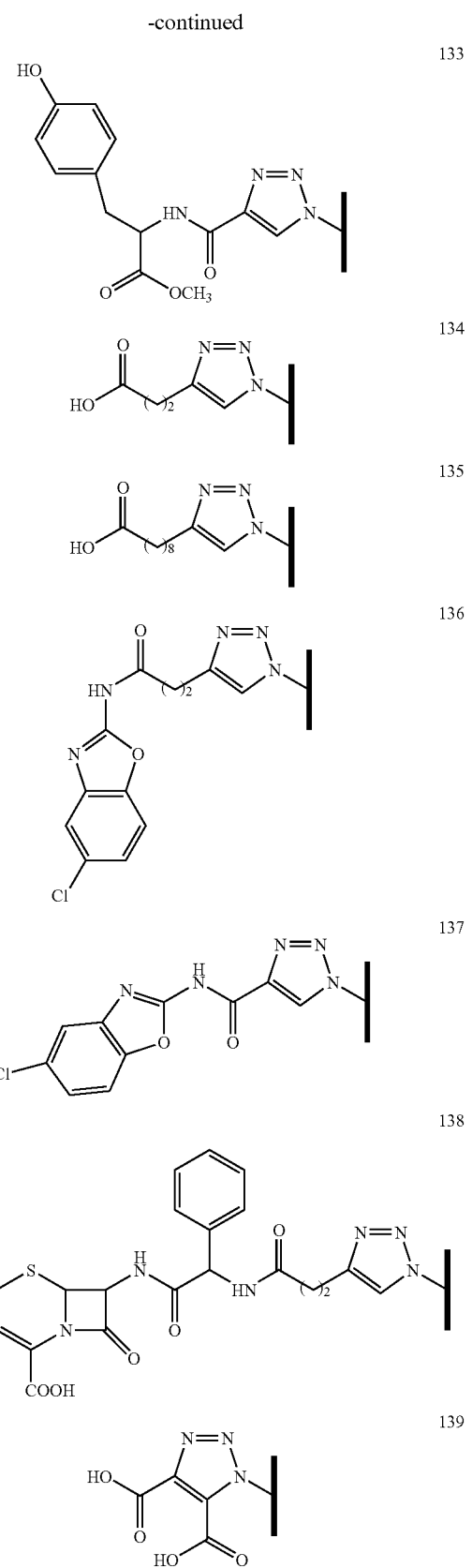

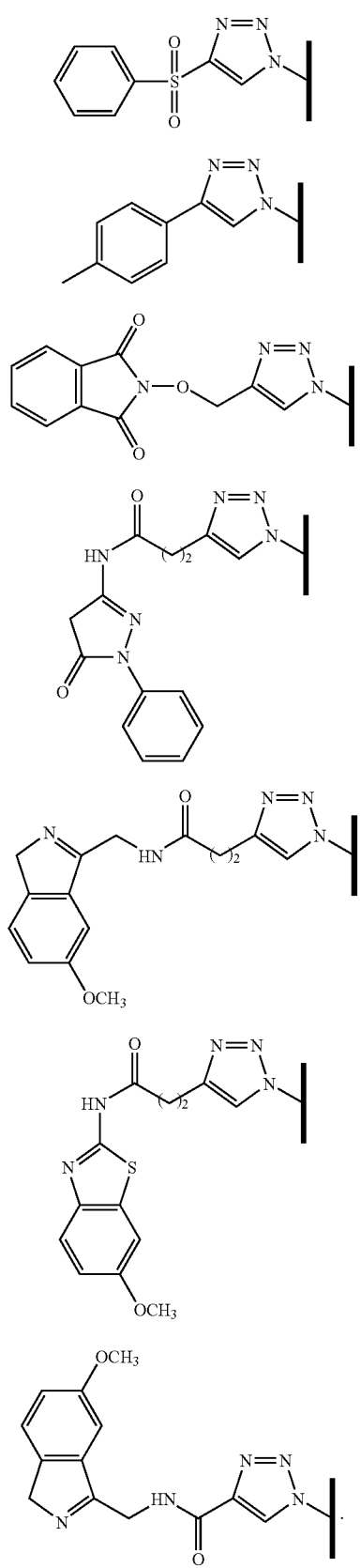

In certain embodiment, the glycosylated compound is initially produced by incubating at least one moiety capable of being glycosylated and at least one thymidine or uridine nucleotide diphosphosugar in the presence of at least one first glycosyltransferase. The nucleotide disphosphosugar includes a sugar structure selected from the group consisting of:

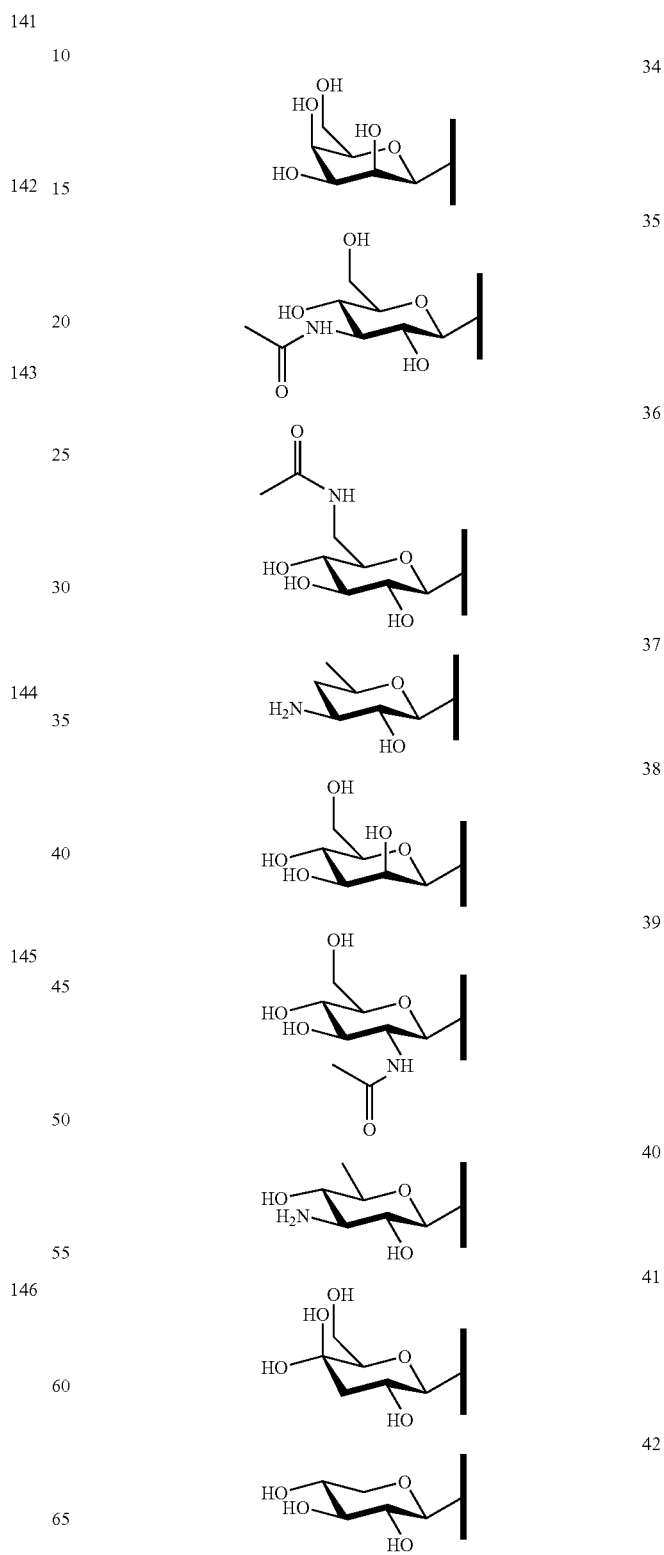

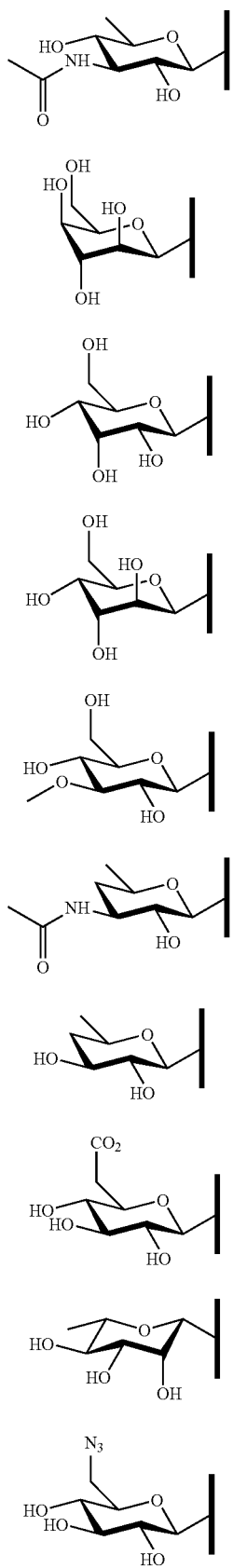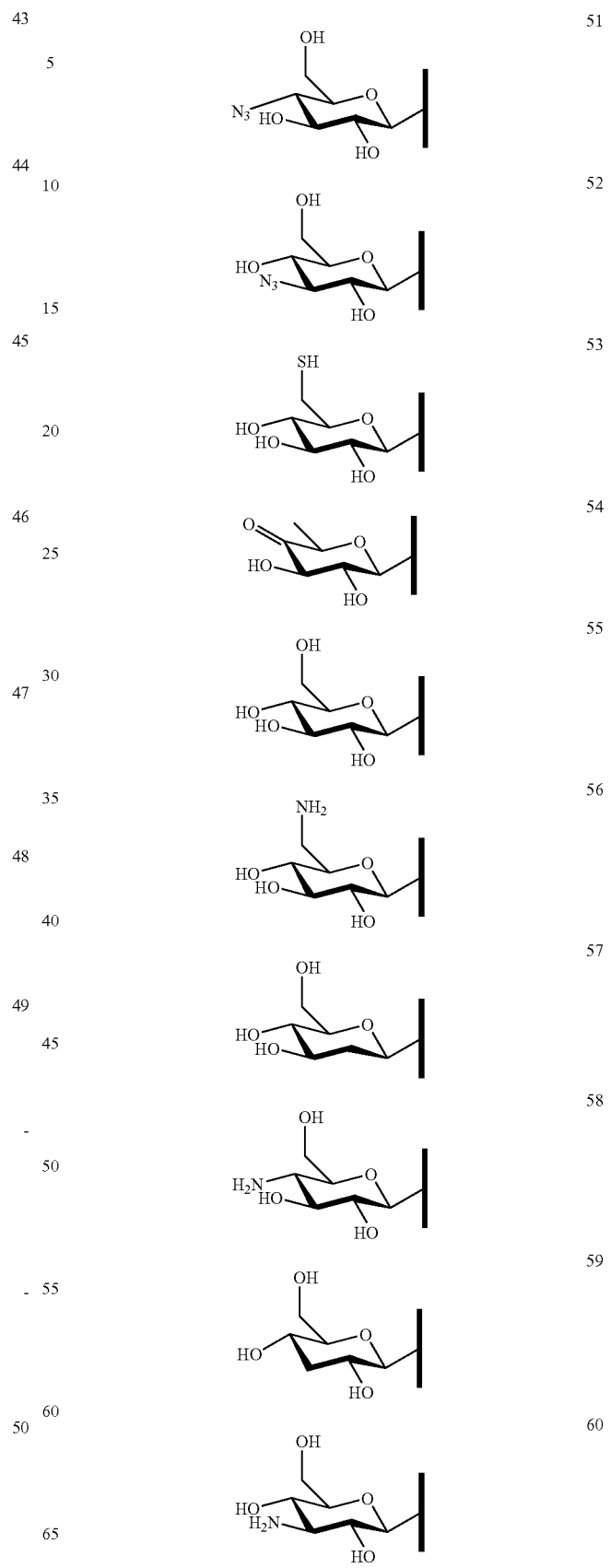

-continued
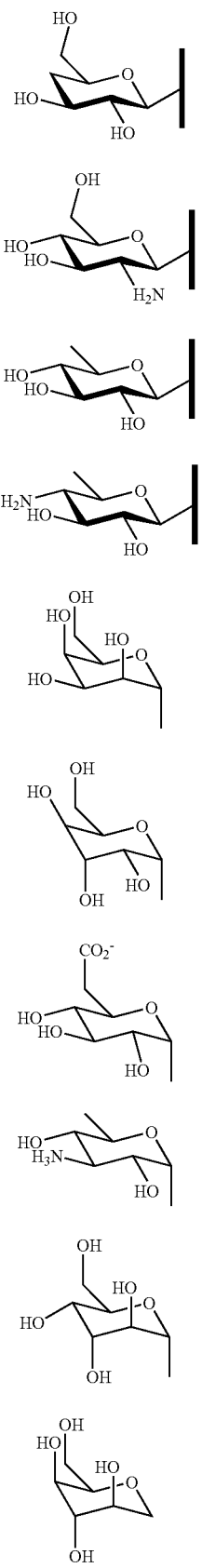
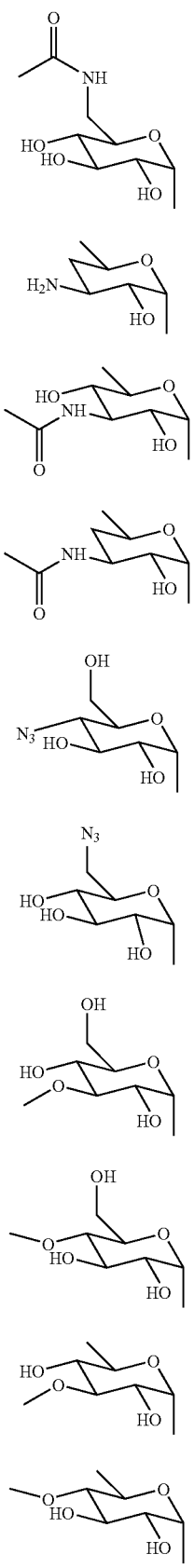

117 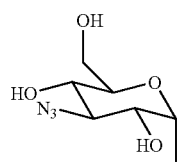
118 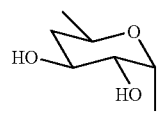
119 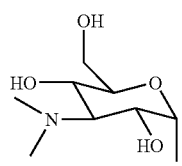
120
121 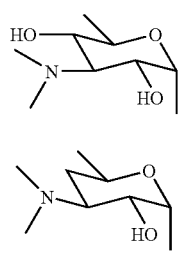
122 
123
124
125
Preferred embodiments also include novel compounds that are produced by the methods described herein.
Non-limiting examples of such novel compounds include the following compounds:
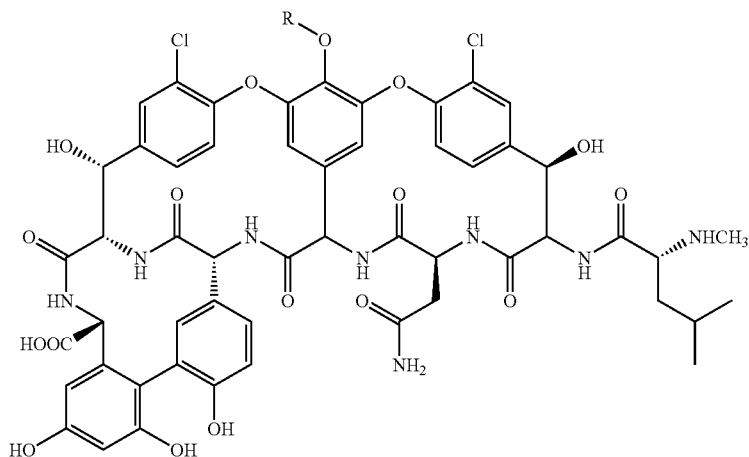

-continued wherein R is 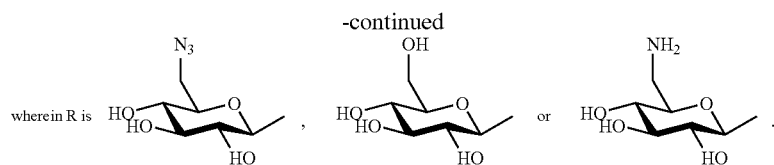

Other non-limiting examples include the following compounds:

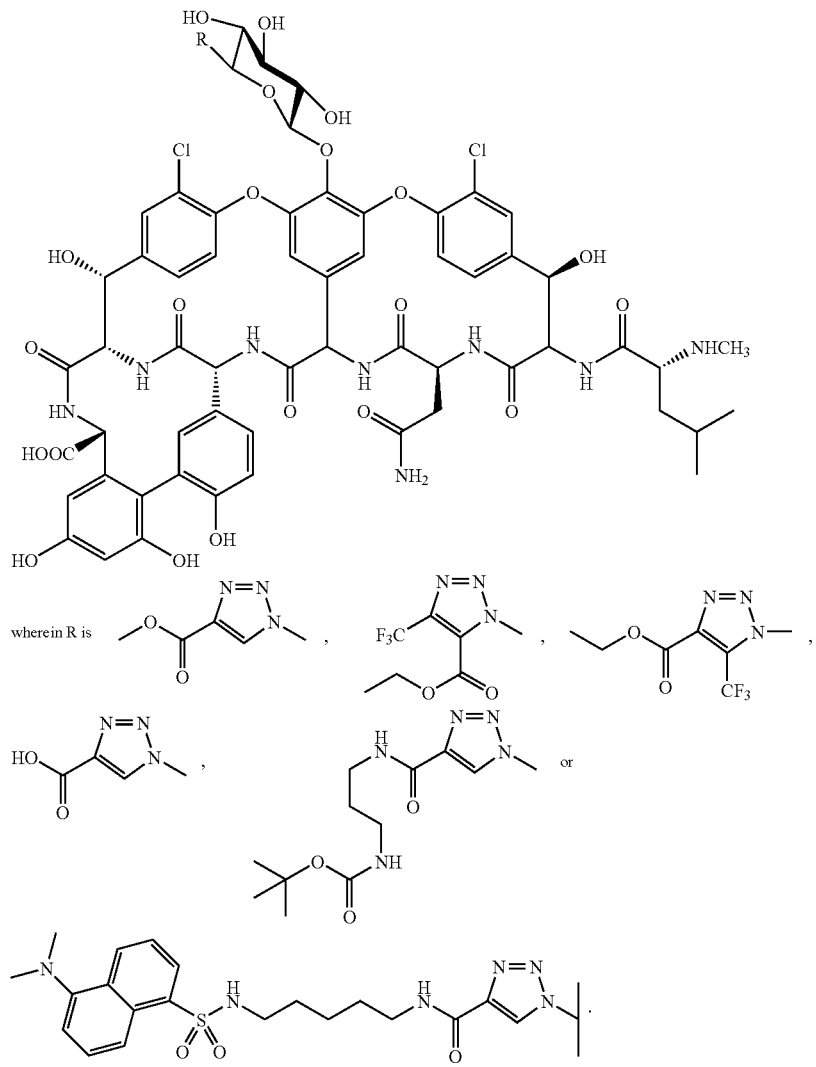

In another embodiment, the present invention provides methods of inhibiting bacterial growth. Such methods include steps of contacting bacteria inhibited by a composition disclosed herein with an effective amount of the composition such that the bacteria's growth is inhibited. Yet another embodiment of the present invention includes methods of reducing or preventing a bacterial infection in a patient. The method includes the step of administering a pharmaceutically effective amount of a composition disclosed herein.

Other objects, features and advantages of the present invention will become apparent after review of the specification, claims and drawings.

BRIEF DESCRIPTION OF THE DRAWINGS

FIG. 3 also provides chemical structures illustrating a portion of the biosynthesis of these NCEs.

FIG. 3 also provides chemical structures illustrating a portion of the biosynthesis of these NCEs.

FIG. 6(A) provides the final stages of vancomycin biosynthesis catalyzed by glucosyltransferase GtfE and vancosaminyltransferase GtfD. (B) provides variants from stage I IVG of the vancomycin aglycon where numbered compounds represent products and (-) indicates no conversion. Compounds 55-64 highlighted in the box represent previously reported products. The changes from the GtfE wild-type substrate (glucose) are highlighted. (C) Provides products from the stage II chemoselective Huisgen 1,3-dipolar cycloaddition of azide 50 and acetylenes to give the corresponding 1,2,3-triazoles 65-80. (D) Provides additional products from stage II chemoselective Huisgen 1,3-dipolar cycloaddition of azide 50 and acetylenes to give the corresponding 1,2,3-triazoles 131-146, with reaction yeilds.

FIG. 9: provides synthesis of UDP-glucose derivatives (A) Synthesis of UDP-2-azido-, 6-azido- and 6-amino-glucose (B) Synthesis of UDP-6-chloro-, 2-fluoro-, and 2-amino-glucose. Reagents and conditions: (a) 1. $iPr_2NP(OCH_2CH_2CN)_2$, tetrazole, $CH_2Cl_2$, –40-0° C.; 2. mCPBA, $CH_2Cl_2$, –40-0° C.; (b) TMG, TMSCl, $CH_3CN$, rt, 1 h; (c) UMP-morpholidate, tetrazole, pyridine, rt, 48 h; (d) $Et_3N$/MeOH/$H_2O$ (1:2:2), 24 h; (e) $H_2$, Pd—C, MeOH, 4 h; (f) 1. $iPr_2NP(OBn)_2$, tetrazole, $CH_2Cl_2$, –40-0° C.; 2. mCPBA, $CH_2Cl_2$, –40-0° C.; (g) NaOMe, MeOH, 1 h.

DETAILED DESCRIPTION OF THE INVENTION

The present invention provides a simple and efficient method to bypass the severe barriers to synthesis posed by both the complexities of biologically active secondary metabolites and the difficulties and limitations of in vivo manipulation, for the first time providing the ability to construct large and diverse libraries macrolides with varied carbohydrate attachments.

The present invention utilizes the promiscuity of nucleotidyltransferases and glycosyltransferases for their respective substrates and donor molecules to provide a method for producing libraries of glycosylated entities, which then may be screened by methods known in the art for compounds useful in, e.g., clinical therapy, biomedical research, and chemical synthesis of downstream products.

A number of genetic in vivo experiments have demonstrated that the glycosyltransferases of secondary metabolism (which include those for anthracyclines, angucyclines, nonribosomal peptides, macrolides and enediynes) are promiscuous with respect to the NDP-sugar donor.

However, prior in vitro studies in this area were severely limited due to the inability to access the appropriate NDP-sugar substrates.

Figure 2:
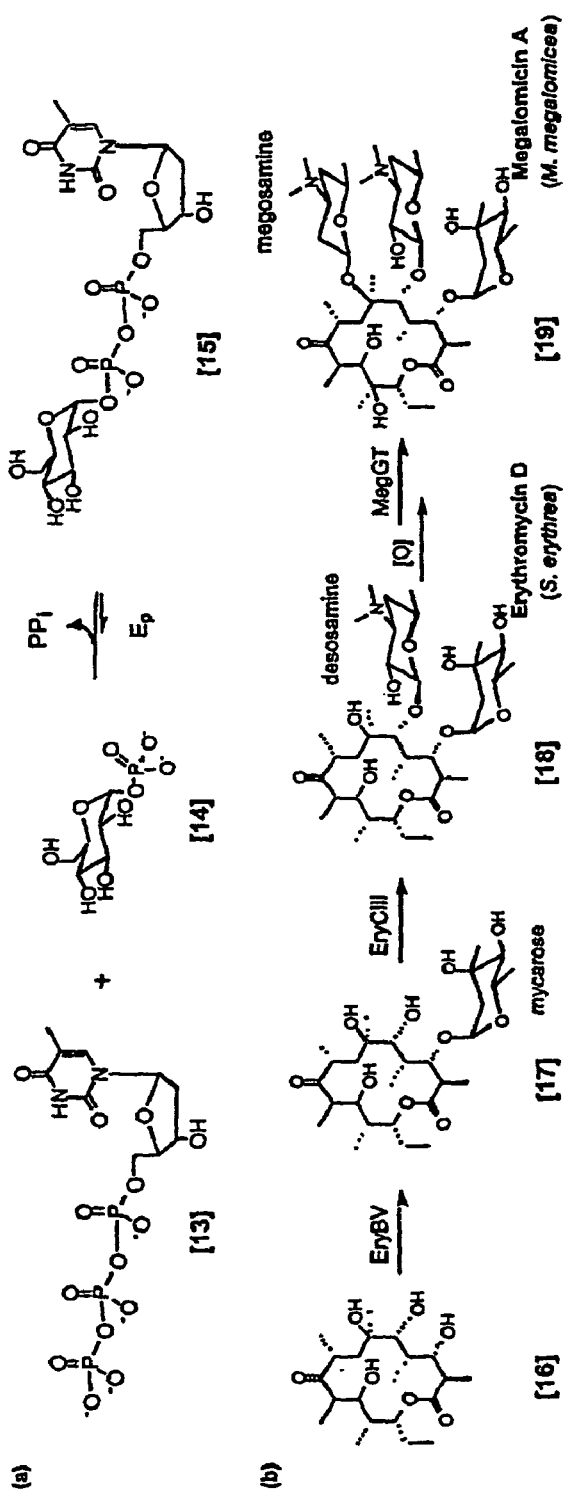
FIG. 2(a) provides chemical structures illustrating a portion of the biosynthesis of megosamine.
FIG. 2(b) provides chemical structures illustrating a portion of the biosynthesais of erythromycin D and Megalomicin A.

The present inventors recently vastly increased the pool of UDP- and dTDP-sugar substrates available by systematically re-examining the substrate specificity of purified $E_p$, which revealed this enzyme can accommodate a wide array of hexopyranosyl phosphates as a replacement for FIG. 2, 14 in this reaction. See, e.g., Jiang J, et al., "Expanding the Pyrimidine Diphosphosugar Repertoire: The Chemoenzymatic Synthesis of Amino- and Acetamidoglucopyranosyl Derivatives" Angew Chem Int Ed Engl 40(8):1502-1505 (2001); Jiang J, et al., "A General Enzymatic Method for the Synthesis of Natural and 'Unnatural' UDP- and TDP-Nucleotide Sugars," Journal of the American Chemical Society 122(28): 6803-6804 (2000).

In comparison to the tedious chemical synthesis of nucleotide sugars, this one-step $E_p$-catalyzed enzymatic conversion is a rapid and effective method to construct libraries of both the desired UDP- and dTDP-nucleotide diphosphosugars for in vitro glycorandomization. As a result, an enormous number of UDP- and dTDP-sugar substrates can be produced, including sugars that were difficult or impossible to produce in vitro prior to the teachings of the present inventors and sugars that have never been produced before. Such nucleotide sugars can be used in the methods of the present invention to produce an enormous number of glycosylated compounds, including glycosylated compounds that were difficult or impossible to produce in vitro prior to the teachings of the present inventors and glycosylated compounds that have never been produced before.

"Novel" nucleotide sugars, as used herein, refer to nucleotide sugars which have not been made in vitro prior to the teachings of the present inventors in the references cited herein, or to nucleotide sugars which have never been produced synthetically prior to the teachings of the present inventors in the references cited herein, or to nucleotide sugars that are completely novel and have never been produced via natural or chemical synthesis. Likewise, "novel" glycosylated compounds, as used herein, refer to glycosylated compounds which have not been made in vitro prior to the teachings of the present inventors in the references cited herein, or to glycosylated compounds which have never been produced synthetically prior to the teachings of the present inventors in the references cited herein, or to glycosylated compounds that are completely novel and have never been produced via natural or chemical synthesis.

Exemplary nucleotide sugars which may be used in methods according to the present invention include, but are not limited to: Thymidine 5'-(a-D-glucopyranosyl diphosphate); Uridine 5'-(a-D-glucopyranosyl diphosphate); Thymidine 5'-(2-deoxy-a-D-glucopyranosyl diphosphate); Uridine 5'-(2-deoxy-a-D-glucopyranosyl diphosphate); Thymidine 5'-(3-deoxy-a-D-glucopyranosyl diphosphate); Uridine 5'-(3-deoxy-a-D-glucopyranosyl diphosphate); Thymidine 5'-(4-deoxy-a-D-glucopyranosyl diphosphate); Uridine 5'-(4-deoxy-a-D-glucopyranosyl diphosphate); Thymidine 5'-(6-deoxy-a-D-glucopyranosyl diphospbate); Uridine 5'-(6-deoxy-a-D-glucopyranosyl diphosphate); Thymidine 5'-(a-D-mannopyranosyl diphosphate); Uridine 5'-(a-D-mannopyranosyl diphosphate); Thymidine 5'-(a-D-galactopyranosyl diphosphate); Uridine 5'-(a-D-galactopyranosyl diphosphate); Thymidine 5'-(a-D-allopyranosyl diphosphate); Thymidine 5'-(a-D-altropyranosyl diphosphate); Uridine 5'-(a-D-allopyranosyl diphosphate); Uridine 5'-(a-D-altropyra-nosyl diphosphate); Thymidine 5'-(a-D-gulopyranosyl diphosphate); Uridine 5'-(a-D-gulopyranosyl diphosphate); Thymidine 5'-(a-D-idopyranosyl diphosphate); Uridine 5'-(a-D-idopyranos-yl diphosphate); Thymidine 5'-(a-D-talopyranosyl diphosphate); Uridine 5'-(a-D-talopyranosyl diphosphate); Thymidine 5'-(6-amino-6-deoxy-a-D-glucopyranosyl diphosphate); Uridine 5'-(6-amino-6-deoxy-a-D-glucopyranosyl diphosphate); Thymidine 5'-(4-amino-4-deoxy-a-D-glucopyranosyl diphosphate); Uridine 5'-(4-amino-4-deoxy-a-D-glucopyra-nosyl diphosphate); Thymidine 5'-(3-amino-3-deoxy-a-D-glucopyranosyl diphosphate); Uridine 5'-(3-amino-3-deoxy-a-D-glucopyranosyl diphosphate); Thymidine 5'-(2-amino-2-deoxy-a-D-glucopyranosyl diphosphate); Uridine 5'-(2-amino-2-deoxy-a-D-glucopyranosyl diphosphate); Thymidine 5'-(6-acetamido-6-deoxy-a-D-glucopyranosyl diphosphate); Uridine 5'-(6-acetamido-6-deoxy-a-D-glucopyranosyl diphosphate); Thymidine 5'-(4-acetamido-4-deoxy-a-D-glucopyranosyl diphosphate); Uridine 5'-(4-acetamido-4-deoxy-a-D-glucopyranosyl diphosphate); Thymidine 5'-(3-acetamido-3-deoxy-a-D-glucopyranosyl diphosphate); Uridine 5'-(3-acetamido-3-deoxy-a-D-glucopyranosyl diphosphate); Thymidine 5'-(2acetamido-2-deoxy-a-D-glucopyranosyl diphosphate); Uridine 5'-(2-acetamido-2-deoxy-a-D-glucopyranosyl diphosphate); Thymidine 5'-(4-amino-4,6-dideoxy-a-D-glucopyranosyl diphosphate); Uridine 5'-(4-amino-4,6-dideoxy-a-D-glucopyranosyl diphosphate); and

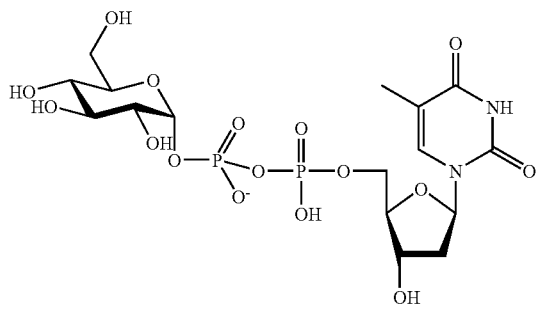

$C_{16}H_{25}N_2O_{15}P_2S^-$
Exact Mass: 579.05
Determined: 579.08

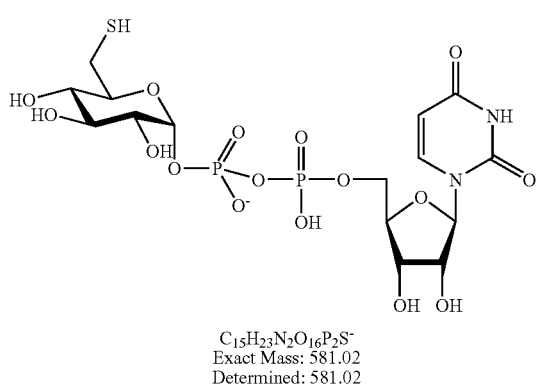

$C_{15}H_{23}N_2O_{16}P_2S^-$
Exact Mass: 581.02
Determined: 581.02

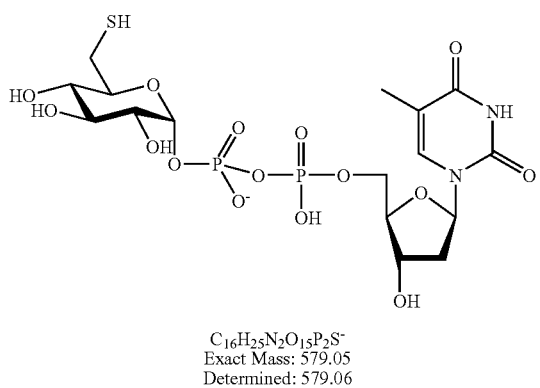

$C_{16}H_{25}N_2O_{15}P_2S^-$
Exact Mass: 579.05
Determined: 579.06

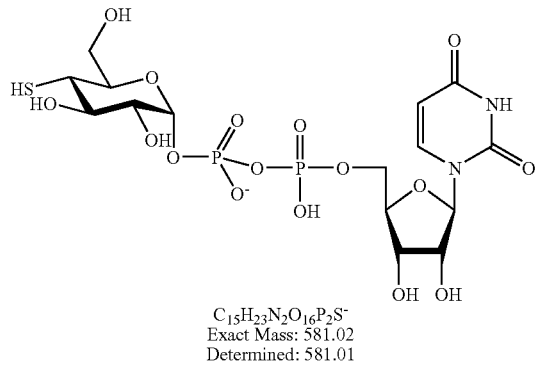

$C_{15}H_{23}N_2O_{16}P_2S^-$
Exact Mass: 581.02
Determined: 581.01

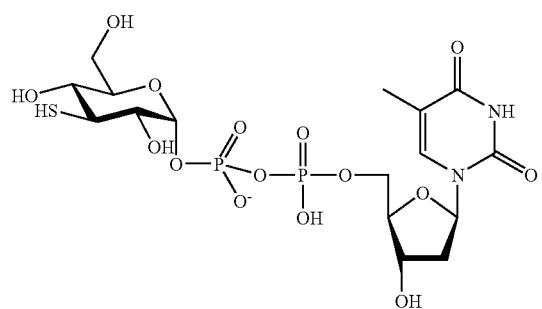
C$_{16}$H$_{25}$N$_2$O$_{15}$P$_2$S$^-$
Exact Mass: 579.05
Determined: 579.02
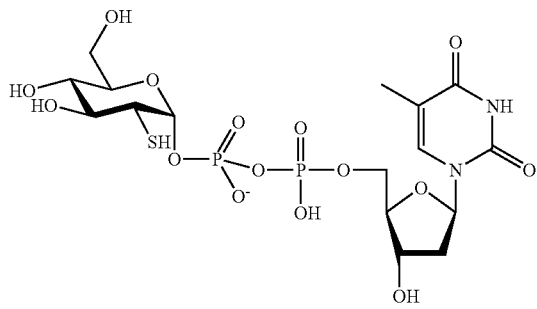
C$_{16}$H$_{25}$N$_2$O$_{15}$P$_2$S$^-$
Exact Mass: 579.05
Determined: 579.10
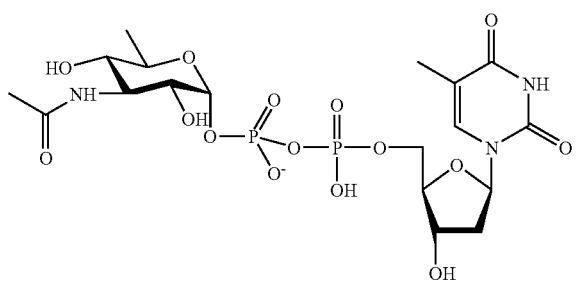
C$_{18}$H$_{28}$N$_3$O$_{15}$P$_2^-$
Exact Mass: 588.10
Determined: 588.04
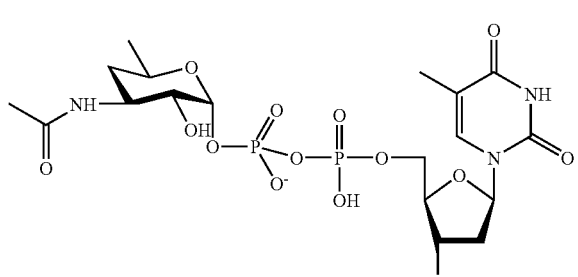
C$_{18}$H$_{28}$N$_3$O$_{14}$P$_2^-$
Exact Mass: 572.10
Determined: 572.14
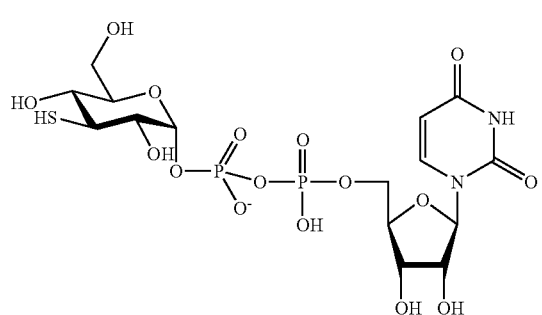
C$_{15}$H$_{23}$N$_2$O$_{16}$P$_2$S$^-$
Exact Mass: 581.02
Determined: 581.05
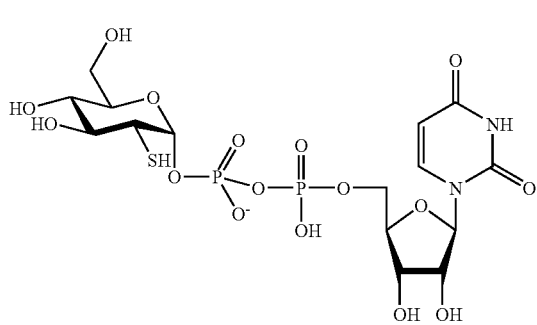
C$_{15}$H$_{23}$N$_2$O$_{16}$P$_2$S$^-$
Exact Mass: 581.02
Determined: 581.08
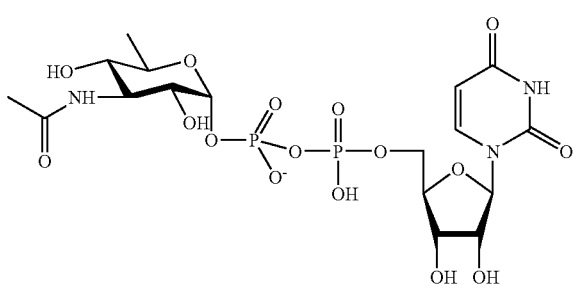
C$_{17}$H$_{26}$N$_3$O$_{16}$P$_2^-$
Exact Mass: 590.08
Determined: 590.15
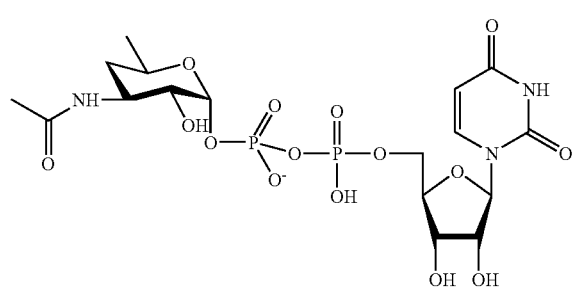
C$_{17}$H$_{26}$N$_3$O$_{15}$P$_2^-$
Exact Mass: 574.08
Determined: 574.10

-continued
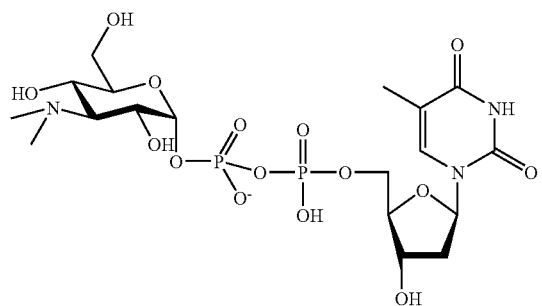
C$_{18}$H$_{30}$N$_3$O$_{15}$P$_2^-$
Exact Mass: 590.12
Determined: 590.15
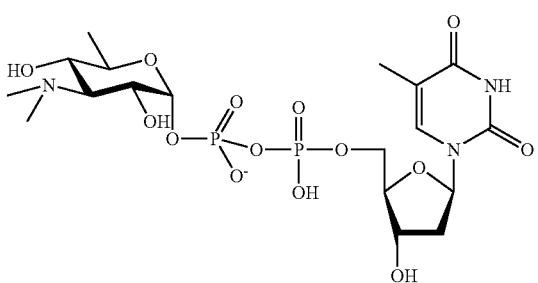
C$_{18}$H$_{30}$N$_3$O$_{14}$P$_2^-$
Exact Mass: 574.12
Determined: 574.12
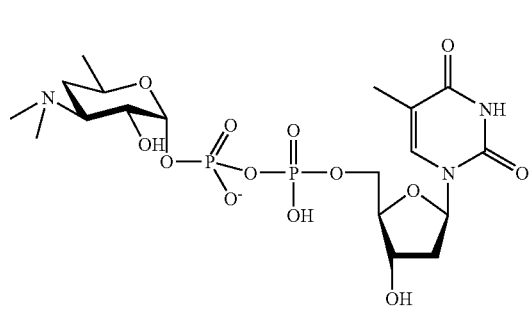
C$_{18}$H$_{30}$N$_3$O$_{13}$P$_2^-$
Exact Mass: 558.13
Determined: 558.17
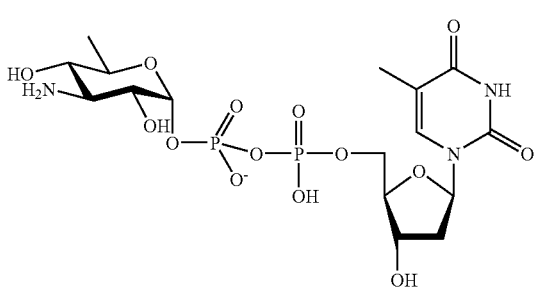
C$_{16}$H$_{36}$N$_3$O$_{14}$P$_2^-$
Exact Mass: 546.09
Determined: 546.05
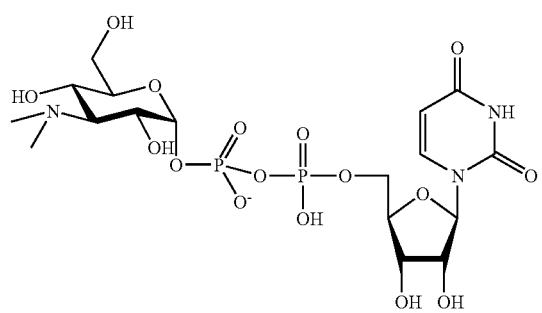
C$_{17}$H$_{28}$N$_3$O$_{16}$P$_2^-$
Exact Mass: 592.09
Determined: 592.09
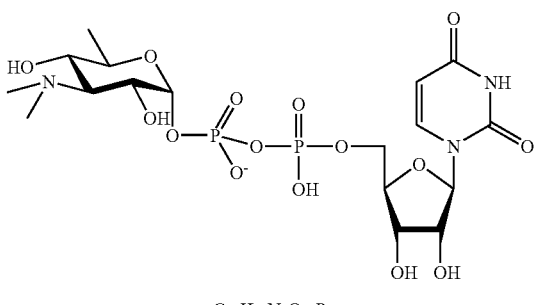
C$_{17}$H$_{28}$N$_3$O$_{15}$P$_2^-$
Exact Mass: 576.10
Determined: 576.03
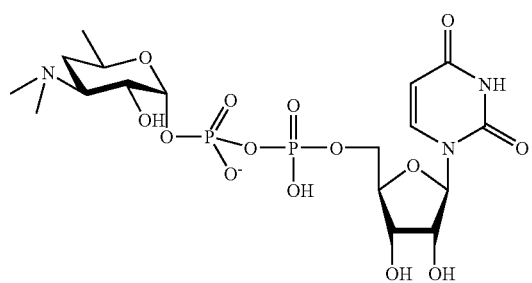
C$_{17}$H$_{28}$N$_3$O$_{14}$P$_2^-$
Exact Mass: 560.10
Determined: 560.15
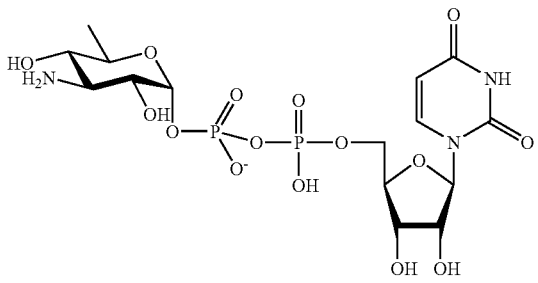
C$_{15}$H$_{24}$N$_3$O$_{15}$P$_2^-$
Exact Mass: 548.07
Determined: 548.13

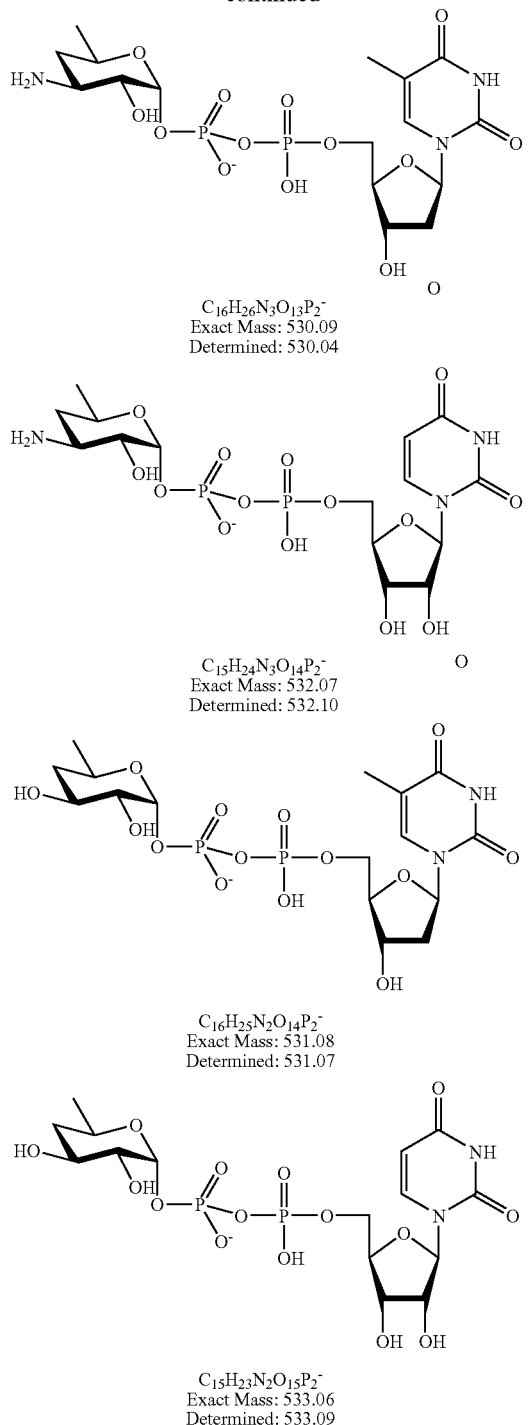

Methods for synthesizing these and other nucleotide sugars are described in Jiang J. et al., "Expanding the Pyrimidine Diphosphosugar Repertoire: The Chemoenzymatic Synthesis of Amino- and Acetamidoglucopyranosyl Derivatives" Angew Chem Int Ed Engl 40(8):1502-1505 (2001); Jiang J. et al., "A General Enzymatic Method for the Synthesis of Natural and 'Unnatural' UDP- and TDP-Nucleotide Sugars," Journal of the American Chemical Society 122(28): 6803-6804 (2000); U.S. Provisional Patent Application Ser. No. 60/254,927, U.S. patent application Ser. No. 10/013,542, and International Patent Application PCT/US01/47953, all entitled: "Active-Site Engineering of Nucleotidylyltransferases and General Enzymatic Methods for the Synthesis of Natural and 'Unnatural' UDP- and TDP-Nucleotide Sugars." Each of these references is hereby incorporated by reference in its entirety. Additional novel nucleotide sugars may be synthesized using the general synthetic methods described therein. As well, methods for synthesizing additional sugars and specific glycosylated moieties (e.g., vancomycin derivatives) are described in U.S. Provisional application Nos. 60/413,520, 60/413,393 and 60/413,376, filed Sep. 25, 2002 all of which are incorporated herein in their entirety for all purposes. Further, additional nucleotide sugars may be synthesized utilizing nucleotidyltransferases that have been mutated to alter or broaden their substrate specificity.

For example, the present inventors discovered the three dimensional structure of and the molecular details of substrate recognition by *Salmonella enterica* LT2 rml A-encoded a-D-glucopyranosyl phosphate thymidylyltransferase ($E_p$), which catalyzes the conversion of a-D-glucopyranosyl phosphate (Glc-1-P) and dTTP to dTDP-a-D-glucose (TDP-Glc) and pyrophosphate ($PP_i$). The present inventors have used this information to design mutants of $E_p$ having substrate specificity that varies from that of wild type $E_p$.

In particular, the present inventors have discovered that, in order to alter substrate specificity, it is preferable to mutate nucleotidyltransferases, such as $E_p$, at one or more amino acids in the active site, the divalent cation binding site, and/or the auxiliary site. More particularly, the present inventors have discovered that it is preferable to mutate $E_p$ at one or more amino acids selected from the group consisting of V173, G147, W224, N112, G175, D111, E162, T201, I200, E199, R195, L89, L89T, L109, Y146 and Y177. Methods for mutating nucleic acids and expressing mutant proteins therefrom are well known in the arts of genetic and protein engineering.

Exemplary nucleotide sugars which may be produced by mutated nucleotidyltransferases and which may be used in methods according to the present invention include, but are not limited to: Thymidine 5'-(6-acetamido-6-deoxy-a-D-glucopyranosyl diphosphate); Uridine 5'-(6-acetamido-6-deoxy-a-D-glucopyranosyl diphosphate); Thymidine 5'-(a-D-glucopyran-6-uronic acid diphosphate); Uridine 5'-(a-D-glucopyran-6-uronic acid diphosphate); Thymidine 5'-(2-acetamido-2-deoxy-a-D-glucopyranosyl diphosphate); Uridine 5'-(2-acetamido-2-deoxy-a-D-glucopyranosyl diphosphate); Thymidine 5'-(4-amino-4,6-dideoxy-a-D-glucopyranosyl diphosphate); Uridine 5'-(4-amino-4,6-dideoxy-a-D-glucopyranosyl diphosphate); Thymidine 5'-(a-D-arabinopyranosyl diphosphate); and Uridine 5'-(a-D-arabinopyranosyl diphosphate).

Methods for producing mutated nucleotidyltransferases and for synthesizing these and other sugars are described in Barton W A, et al., "Structure, mechanism and engineering of a nucleotidylyltransferase as a first step toward glycorandomization," Nat Struct Biol 8(6):545-51 (2001); U.S. Provisional Patent Application Ser. No. 60/254,927, U.S. patent application Ser. No. 10/013,542, and International Patent Application PCT/US01/47953, all entitled: "Active-Site Engineering of Nucleotidylyltransferases and General Enzymatic Methods for the Synthesis of Natural and 'Unnatural' UDP- and TDP-Nucleotide Sugars." Each of these references is hereby incorporated by reference in its entirety. Additional mutated nucleotidyltransferases and additional novel nucleotide sugars may be synthesized using the general synthetic methods described therein.

In addition to the great diversity of nucleotide sugars now available, a large number of glycosyltransferases are available. Any known glycosyltransferase may be selected for use in the methods of the present invention. Preferably, glycosyltransferases for use in the present invention are selected from those glycosyltransferases known to be involved in the synthesis of bioactive metabolites. Additionally, glycosyltransferase for use in the methods of the present invention may be produced by expressing the product of a putative glycosyltransferase gene. Such genes are known in the art, and methods for expressing gene products are also known in the art.

In certain embodiments, the glycosyltransferase is selected from the group including, but not limited to, CalB, CalE, CalN, CalU, Gra orf14, Gra orf5, LanGT1, LanGT2, LanGT3, LanGT4, MtmGI, MtmGII, MtmGIII, MtmGTIV, NovM, RhlB, Rif orf 7, SnogD, SnogE, SnogZ, UrdGT1a, UrdGT1b, UrdGT1c, UrdGT2, AknK, AknS, DesVII, DnrS, OleG1, OleG2, TylCV, TylMII, TylN, DauH, DnrH, EryBV, EryCIII, Ngt, BgtA, BgtB, BgtC, GftA, GftB, GftC, GftD, GftE, Gp1-1, Gp1-2, RtfA, AveBI, BlmE, BlmF, MgtA, NysD1, OleD, OleI, SpcF, SpcG, StrH, Ugt51B1, Ugt51C1, UGT52, UgtA, UgtB, UgtC, UgtD and homologs thereof. See, e.g., U.S. Ser. Nos. 09/457,045; 09/724,797; Thorson, J. S. et al. "Nature's Carbohydrate Chemists: The Enzymatic Glycosylation of Bioactive Bacterial Metabolites," Curr. Org. Chem. 5: 139-167 (2001); Weymouth-Wilson, A. C. "The Role of Carbohydrates in Biologically Active Natural Products," Nat. Prod. Rep. 14: 99-110 (1997).

When one or more moieties capable of being glycosylated and a diverse pool of NDP-sugars are incubated in under appropriate conditions in the presence of a glycosyltransferase, a diverse library of glycorandomized structures is produced. Incubating the resultant glycosylated entities one or more additional times in the presence of the same or different glycosyltransferase(s) and a pool of the same or different sugars results in a library of glycorandomized structures that becomes more diverse and complex with each glycosylation incubation.

In this manner, coupled with the presented $E_p$-catalyzed production of NDP-sugar donor libraries and the appropriate aglycon, or moiety capable of being glycosylated, the flexibility of wild-type glycosyltransferases in secondary metabolism can be used to rapidly generate a diverse library of "glycorandomized" structures, in combinatorial fashion, based upon a particular natural product scaffold. Moieties capable of being glycosylated may be referred to as "aglycons." However, when the aglycon of a specific biomolecule is referred to (e.g., the aglycon of anthracyclines), the specific aglycon of that specific biomolecule is meant.

Using methods of combinatorial chemistry, glycosyltransferase(s) are incubated with a pool of nucleotide sugar substrates and a pool of entities capable of being glycosylated under conditions favoring the transfer by the glycosyltransferase of the glycosyl groups from the nucleotide sugar substrates to the entities capable of being glycosylated. General appropriate conditions are known in the art. Appropriate conditions may vary from one particular enzyme to another, and optimal conditions for any particular enzyme may be determine using methods known in the art.

The incubation may be carried out with one or more glycosyltransferases. Likewise, the pool of nucleotide sugars may comprise one or more sugars. Preferably, the pool of sugars comprises different nucleotidyl sugars. More preferably, the pool of sugars comprises a highly diverse population of nucleotidyl sugars. The pool of sugars may comprise known nucleotidyl sugars and/or novel nucleotidyl sugars. When it is desired to use novel nucleotidyl sugars, such sugars may be made by exploiting the promiscuity of nucleotidyltransferases by employing the methods described in Jiang, J. et al. (2000); Jiang J. et al. (2001); Barton W. A., et al., "Structure, Mechanism and Active-Site Engineering of a Nucleotidylyltransferase: The First Step in the Glycorandomization of Natural Product-Based Metabolites," Nature Structural Biology (2001), manuscript in press; and U.S. Ser. No. 60/254,927.

The incubation may be carried out with one or more entity capable of being glycosylated. Entities capable of being glycosylated may be selected from natural and synthetic aglycons, natural product metabolites, oligosaccharides, proteins, and peptides. Entities capable of being glycosylated may also be selected from the aglycons of bioactive anthracyclines, angucyclines, nonribosomal peptides (such as vancomycin), macrolides, enediynes, indolocarbazoles, pluramycins, aurelolic acids, orthosomycins, aminoglycosides, coumarins, bleomycins, amicetins, polyenes, benzoisochromanequinones, angucyclines, steroids, lipids, polyketides, oligosaccharides, peptides, proteins, other numerous classes of bioactive metabolites, and hybrids consisting of one or more of these components.

Entities capable of being glycosylated include entities that are already glycosylated, whether by methods of the present invention, by other synthetic or biosynthetic methods, or naturally occurring. Additional glycosyl groups may be attached to a previously attached glycosyl group in order to form a saccharide chain. Additional glycosyl groups may also or alternatively be attached to the original entity capable of being glycosylated, e.g., the aglycon.

The same glycosyltransferase may be used in repeated cycles of glycosylation of a pool of entities capable of being glycosylated. However, preferably, different glycosyltransferases are used in repeated cycles of glycosylation.

In this manner, entities that have been glycosylated according to the methods of the present invention may be subjected to repeated cycles of incubation with glycosyltransferases and pools of sugars until a population of the desired type and size of glycosylated entities is achieved. Preferably, the population of glycosylated entities produced is highly diverse. Also preferably, the pool of glycosylated entities produced comprises novel compounds. Most preferably, the pool of glycosylated entities comprises compounds with novel, enhanced, and/or therapeutically useful biological activity.

Two novel novobiocin (designated Nov-1 and Nov-2) derivatives and six novel erythromycin (designated Ery-1-Ery-6) analogs were produced using the methods of the present invention. By exposing these novel compounds to repeated cycles of glycosylation, a large library of diverse novel compounds may be produced.

The present invention will now be illustrated by the following examples, which show how certain specific representative embodiments of the compounds and methods of the present invention, the compounds, intermediates, process steps, and the like being understood as examples that are intended to be illustrative only. In particular, the invention is not intended to be limited to the conditions, order of the steps and the like specifically recited herein. Rather, the Examples are intended to be illustrative only.

EXAMPLES

Sugars

For all Examples, the sugars tested included or includes: UDP xylose (commercially available); Thymidine 5'-(a-D-glucopyranosyl diphosphate); Uridine 5'-(a-D-glucopyranosyl diphosphate); Thymidine 5'-(2-deoxy-a-D-glucopyranosyl diphosphate); Uridine 5'-(2-deoxy-a-D-glucopyranosyl diphosphate); Thymidine 5'-(3-deoxy-a-D-glucopyranosyl diphosphate); Uridine 5'-(3-deoxy-a-D-glucopyranosyl diphosphate); Thymidine 5'-(4-deoxy-a-D-glucopyranosyl diphosphate); Uridine 5'-(4-deoxy-a-D-glucopyranosyl diphosphate); Thymidine 5'-(6-deoxy-a-D-glucopyranosyl diphosphate); Uridine 5'-(6-deoxy-a-D-glucopyranosyl diphosphate); Thymidine 5'-(a-D-mannopyranosyl diphosphate); Uridine 5'-(a-D-mannopyranosyl diphosphate); Thymidine 5'-(a-D-galactopyranosyl diphosphate); Uridine 5'-(a-D-galactopyranosyl diphosphate); Thymidine 5'-(a-D-allopyranosyl diphosphate); Thymidine 5'-(a-D-altropyranosyl diphosphate); Thymidine 5'-(2-amino-2-deoxy-a-D-glucopyranosyl diphosphate); Uridine 5'-(2-amino-2-deoxy-a-D-glucopyranosyl diphosphate); Thymidine 5'-(3-amino-3-deoxy-a-D-glucopyranosyl diphosphate); Uridine 5'-(3-amino-3-deoxy-a-D-glucopyranosyl diphosphate); Thymidine 5'-(4-amino-4-deoxy-a-D-glucopyranosyl diphosphate); Uridine 5'-(4-amino-4-deoxy-a-D-glucopyranosyl diphosphate); Thymidine 5'-(6-amino-6-deoxy-a-D-glucopyranosyl diphosphate); Uridine 5'-(6-amino-6-deoxy-a-D-glucopyranosyl diphosphate); Thymidine 5'-(4-amino-4,6-dideoxy-a-D-glucopyranosyl diphosphate); Uridine 5'-(4-amino-4,6-dideoxy-a-D-glucopyranosyl diphosphate); Thymidine 5'-(2-acetamido-2-deoxy-a-D-glucopyranosyl diphosphate); Uridine 5'-(2-acetamido-2-deoxy-a-D-glucopyranosyl diphosphate); Thymidine 5'-(3-acetamido-3-deoxy-a-D-glucopyranosyl diphosphate); and Uridine 5'-(6-acetamido-6-deoxy-a-D-glucopyranosyl diphosphate).

Methods for making these and other sugars are described in Barton W A, et al., "Structure, mechanism and engineering of a nucleotidylyltransferase as a first step toward glycorandomization," Nat Struct Biol 8(6):545-51 (2001); Jiang J, et al., "Expanding the Pyrimidine Diphosphosugar Repertoire: The Chemoenzymatic Synthesis of Amino- and Acetamidoglucopyranosyl Derivatives" Angew Chem Int Ed Engl 40(8):1502-1505 (2001); Jiang J, et al., "A General Enzymatic Method for the Synthesis of Natural and 'Unnatural' UDP- and TDP-Nucleotide Sugars," Journal of the American Chemical Society 122(28): 6803-6804 (2000); U.S. Provisional Patent Application Ser. No. 60/254,927, U.S. patent application Ser. No. 10/013,542, and International Patent Application PCT/US01/47953, all entitled: "Active-Site Engineering of Nucleotidylyltransferases and General Enzymatic Methods for the Synthesis of Natural and 'Unnatural' UDP- and TDP-Nucleotide Sugars." Each of these references is hereby incorporated by reference in its entirety.

Example 1

Novel Macrolide Antibiotics 2.5 mM nucleotide sugar, 2 mM aglycon 17, and 10 μg of glycosyltransferase EryCIII in 50 mM potassium phosphate buffer (pH 8.0) was incubated at 37° C. for 12 hr, then concentrated via lyopholization.

The resultant mixture was analyzed by HPLC ($C_{18}$, 25% $CH_3CN$/20 mM potassium phosphate, pH 9.0 for the first 10 min followed by an increase to 40% $CH_3CN$ for an additional 25 min; erythronolides observed at 205 nm). Under these conditions, the retention times for the standards aglycon 17 and erythromycin $A_1$ were 11 min and 25 min, respectively. New peaks, in comparison to the appropriate controls, were observed in the presence of: thymidine 5'-(2-deoxy-a-D-glucopyranosyl diphosphate) (to give Ery-1 with a retention time of 15 min); thymidine 5'-(2-amino-2-deoxy-a-D-glucopyranosyl diphosphate) (to give Ery-2 with a retention time of 13 min); thymidine 5'-(3-deoxy-a-D-glucopyranosyl diphosphate) (to give Ery-3 with a retention time of 15 min); thymidine 5'-(4-deoxy-a-D-g-lucopyranosyl diphosphate) (to give Ery-4 with a retention time of 15 min); thymidine 5'-(6-deoxy-a-D-glucopyranosyl diphosphate) (to give Ery-5 with a retention time of 15 min); and thymidine 5'-(a-D-galactopyranosyl diphosphate) (to give Ery-6 with a retention time of 16 min). These peaks were isolated and characterized by HRMS, confirming the identity of the compounds presented in FIG. 3. The presented stereo- and regiochemistry of these structures is based upon the known reaction catalyzed by EryCIII.

The aglycon 17 can be obtained from *Saccharopolyspoar erythrea*, which produces the compound naturally. In addition, genetic manipulations can be made which result in *S. erythrea* which make greater quantities of this aglycon.

The nucleotide sugar library examined (see above under "Sugars") contained a few commercially available analogs, but was comprised primarily of synthetically if generated derivatives. Jiang, J. et al (2000); Jiang J. et al. (2001); Barton W. A., et al., "Structure, Mechanism and Active-Site Engineering of a Nucleotidylyltransferase: The First Step in the Glycorandomization of Natural Product-Based Metabolites," Nature Structural Biology (2001), manuscript in press; and U.S. Ser. No. 60/254,927. Each sugar was presented individually in a reaction separate from other sugars.

Figure 3:
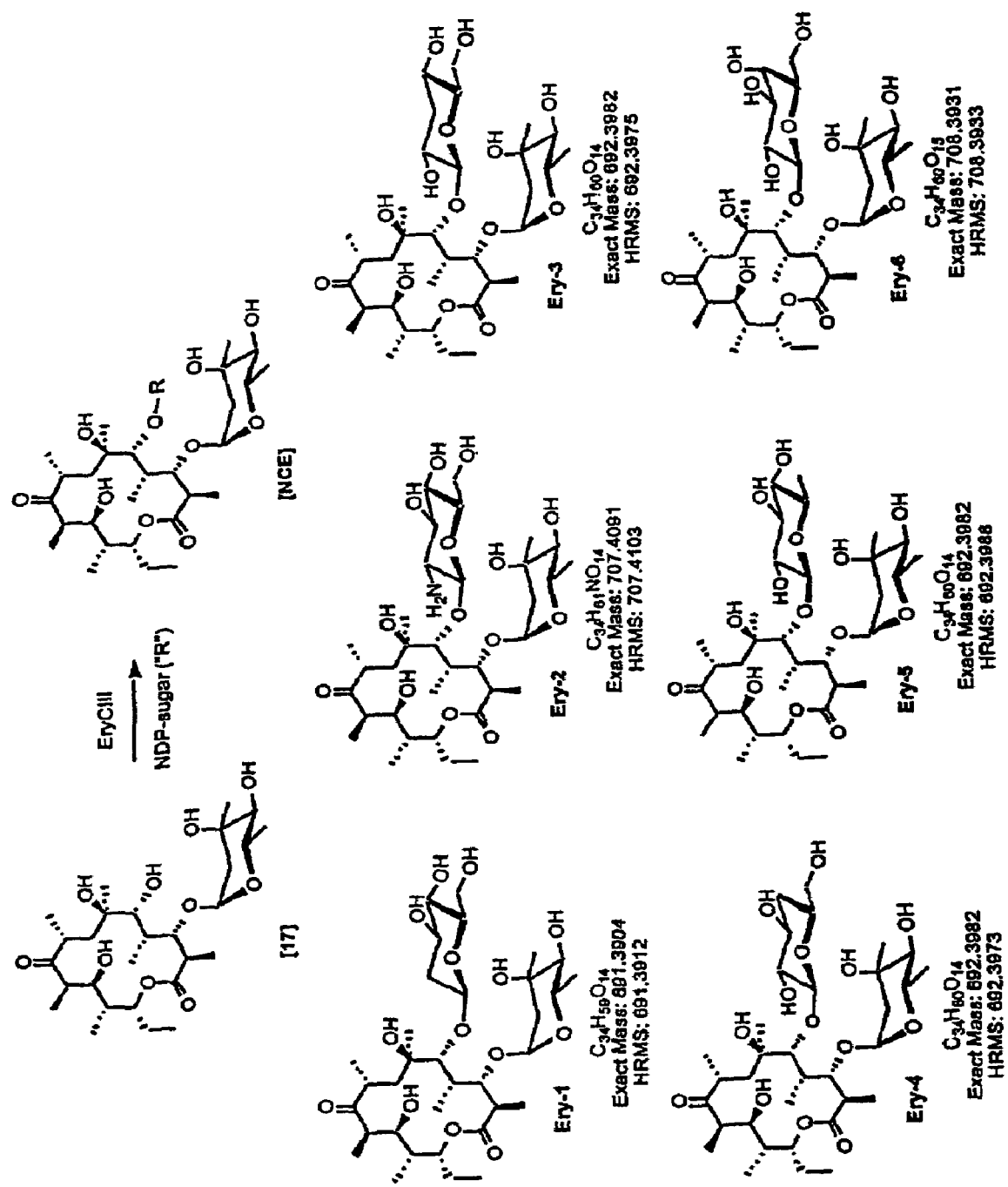
FIG. 3 provides chemical structures for new chemical entities (NCEs) Ery-1, Ery-2, Ery-3, Ery-4, Ery-5, and Ery-6.

In FIG. 3, the "R" designates the sugar portion of the NDP-sugar which is transferred by EryCIII to aglycon 17 to generate the new compounds (designated New Chemical Entity in FIG. 3). The gene encoding EryCIII (eryCIII, accessions AAB84072 and CAA74710; Stauton, J. et al. Chem. Rev. 97: 2611 (1997); Summers, R. G., et al. Microbiol. 143: 3251 (1997)) was PCR amplified directly from *S. erythrea* genomic DNA, isolated from a strain purchased from ATCC, and expressed as a C-terminus His-tag fusion protein. EryCIII was subsequently overexpressed in *E. coli*, partially purified using a nickel affinity column and used as a fresh preparation in the assays.

Example 2

Novel Coumarin Antibiotics 2.5 mM nucleotide sugar, 2 mM aglycon 20, and 10 μg of glycosyltransferase NovM in 50 mM potassium phosphate buffer (pH 8.0) was incubated at 37° C. for 12 hr, then concentrated via lyopholization.

The resultant mixture was analyzed by HPLC ($C_{18}$, 70-80% MeOH/0.1% TFA, novobiocin analogs visualized at 305 nm). Under these conditions, the retention times for the standards aglycon 20 and novobiocin (4) were 21 min and 23 min, respectively. New peaks, in comparison to the appropriate controls, were observed in the presence of: thymidine or uridine 5'-(6-deoxy-a-D-glucopyranosyl diphosphate) (to give Nov-1 with a retention time of 17 min); and thymidine 5'-(a-D-xylopyranosyl diphosphate) (to give Nov-2 with a retention time of 16 min). These peaks were isolated and characterized by HRMS, confirming the identity of the compounds presented in FIG. 4. The presented stereo- and regiochemistry of these structures is based upon the known reaction catalyzed by NovM.

The aglycon 20 was synthesized via the chemical hydrolysis of commercially available novobiocin. The nucleotide sugar library examined (see above under "Sugars") contained a few commercially available analogs, but was comprised primarily of synthetically generated derivatives. Jiang, J. et al. (2000); Jiang J. et al. (2001); Barton W. A., et al., "Structure, Mechanism and Active-Site Engineering of a Nucleotidylyltransferase: The First Step in the Glycorandomization of Natural Product-Based Metabolites," Nature Structural Biology (2001), manuscript in press; and U.S. Ser. No. 60/254,927. Each sugar was presented individually in a reaction separate from other sugars.

Figure 4:
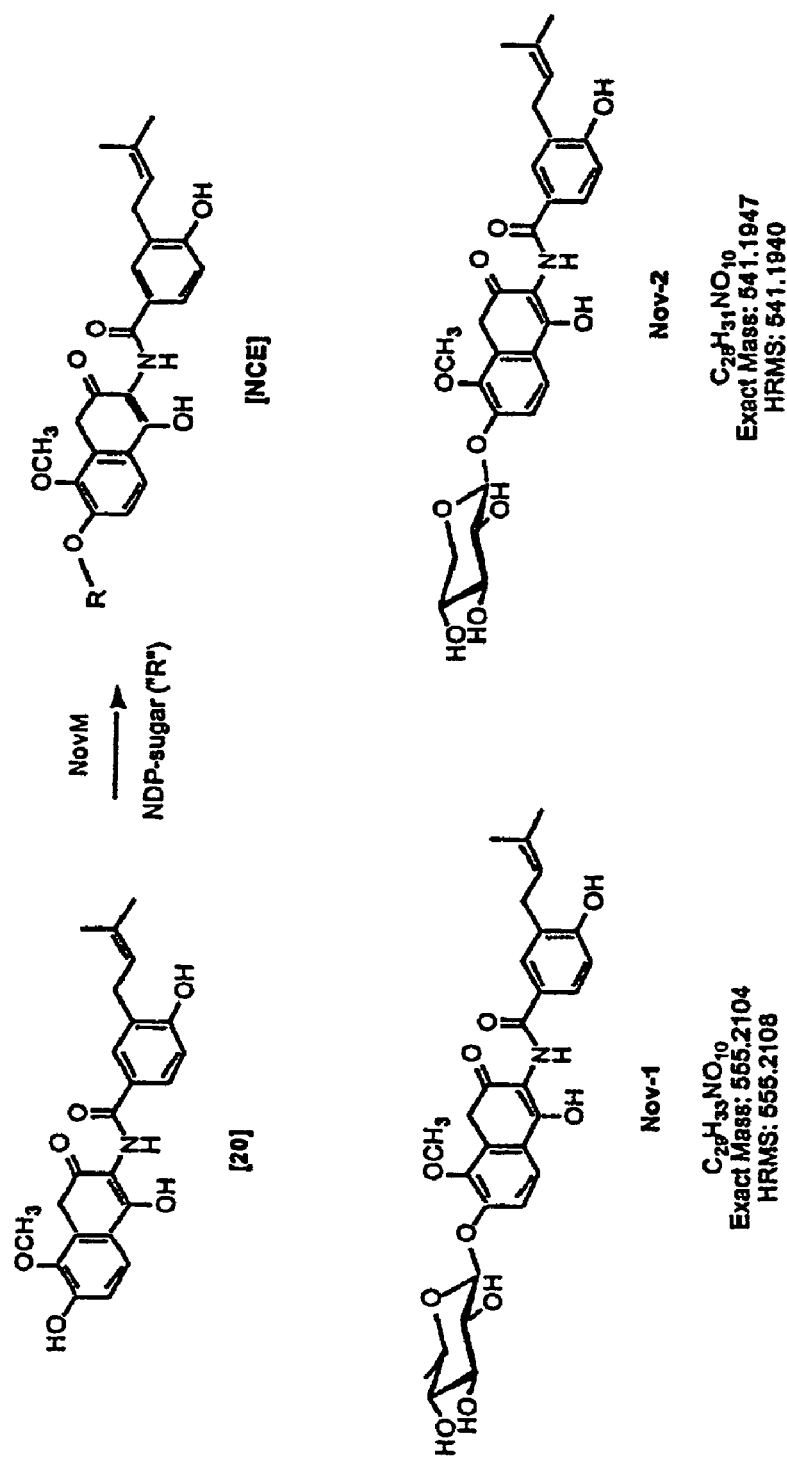
FIG. 4 provides chemical structures for new chemical entities (NCEs) Nov-1 and Nov-2.

In FIG. 4, the "R" designates the sugar portion of the NDP-sugar which is transferred by NovM to aglycon 20 to generate the new compounds (designated New Chemical Entity in FIG. 4). The gene encoding NovM (novM, accession AAF67506) was PCR amplified directly from S. spheroides genomic DNA, isolated from a strain purchased from ATCC, and expressed as a C-terminus His-tag fusion protein. NovM was subsequently overexpressed in E. coli, partially purified using a nickel affinity column and used as a fresh preparation in the assays.

Example 3

Generation of Larger Combinatorial Libraries 2 mM each of newly generated Ery-1 through Ery-6 are incubated at 37° C. for 12 hr with 2.5 mM nucleotide sugar and 10 µg of glycosyltransferase MegD1 (the next glycosyltransferase in the megalomicin cascade). In the presence of a pool of 20 nucleotide sugars, an anticipated 120 NCE's (6×20) are generated.

The resultant mixture is analyzed by HPLC ($C_{18}$, 70-80% MeOH/0.1% TFA, erythronolides observed at 205 nm). Novel compounds are identified. New peaks are isolated and characterized by HRMS. Stereo- and regiochemistry of the novel erythronolides are determined based upon the known reaction catalyzed by MegD1.

The nucleotide sugar library examined (see above under "Sugars") contains a few commercially available analogs, but is comprised primarily of synthetically generated derivatives. Jiang, J. et al. (2000); Jiang J. et al. (2001); Barton W. A., et al., "Structure, Mechanism and Active-Site Engineering of a Nucleotidylyltransferase: The First Step in the Glycorandomization of Natural Product-Based Metabolites," Nature Structural Biology (2001), manuscript in press; and U.S. Ser. No. 60/254,927. Each sugar is presented individually in a reaction separate from other sugars.

Example 4

Novel Non-Ribosomal Peptides 3 mM each of aglycon from vancomycin, teicoplanin or chloroeremomycin are incubated at 37° C. for 12 hr with 6 mM nucleotide sugars and 10 µg of glycosyltransferase (GtfA-E from Amycolatopis orientalis strains, accession AAB49299, Solenberg, P. J. et al, Chem. Biol. 4: 195 (1997)). Products from the first glycosylation are then used as the aglycon for the next glycosyltransferase. In the presence of a pool of 5 glycosyltransferases, 3 aglycons and 20 nucleotide sugars, an anticipated 8800 NCE's ([20×20×20]+[20×20]+[20×20]=8800) are generated.

The resultant mixture is analyzed by HPLC ($C_{18}$, 0-40% $CH_3CN$/0.1% TFA, erythronolides observed at 285 nm). Novel compounds are identified. New peaks are isolated and characterized by HRMS. Stereo- and regiochemistry of the novel non-ribosomal peptides are determined based upon the known reaction catalyzed by GtfA-E.

The nucleotide sugar library examined (see above under "Sugars") contains a few commercially available analogs, but is comprised primarily of synthetically generated derivatives. Jiang, J. et al. (2000); Jiang J. et al. (2001); Barton W. A., et al., "Structure, Mechanism and Active-Site Engineering of a Nucleotidylyltransferase: The First Step in the Glycorandomization of Natural Product-Based Metabolites," Nature Structural Biology (2001), manuscript in press; and U.S. Ser. No. 60/254,927. Each sugar is presented individually in a reaction separate from other sugars.

Example 5

Figure 5:
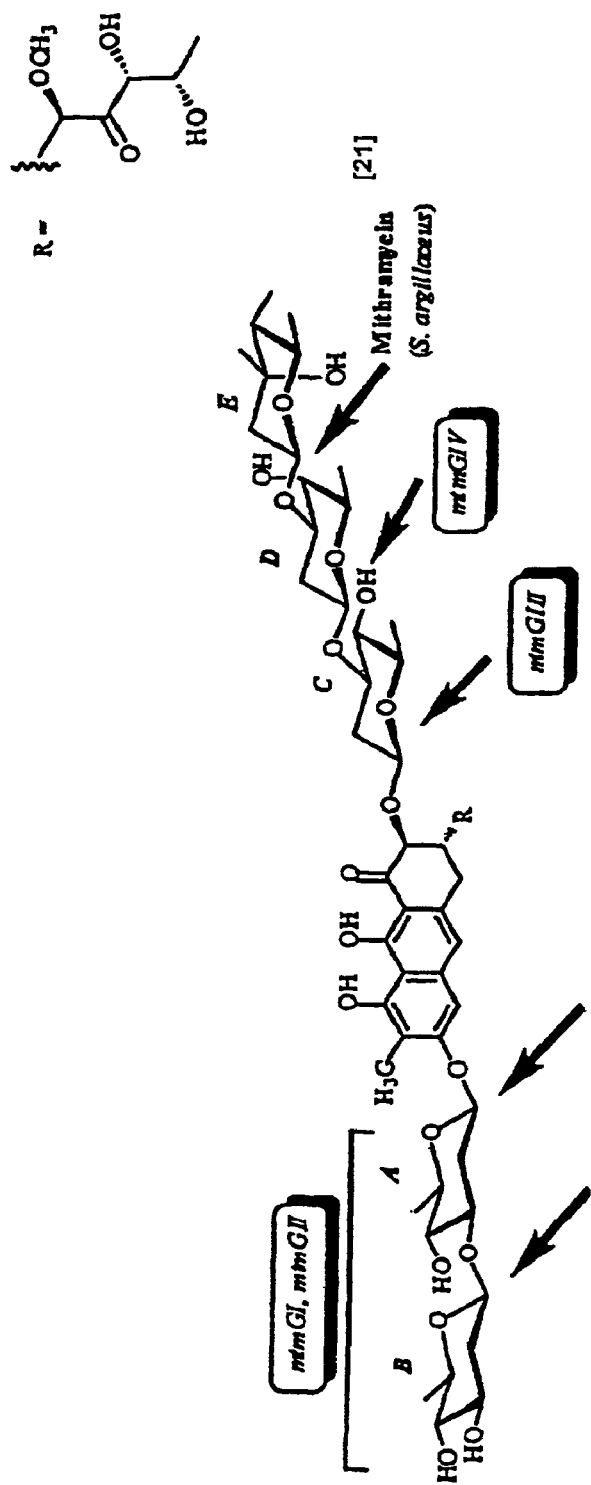
FIG. 5 provides a chemical structure for antitumor agent mithramycin. Various other features, objects, and advantages of the invention will be apparent to those skilled in the art from the following detailed description including illustrative examples setting forth how to make and use the invention.

Novel Aureolic Acids 2 mM of aglycon from the known antitumor agent mithramycin (FIG. 5, 21; Thorson, J. S. et al. (2001)) is incubated at 37° C. for 12 hr with 2.5 mM nucleotide sugars and 10 µg of glycosyltransferase (MtmI, encoded by mtmGI cloned from Streptomyces argillaceus (accession AAC64927)). Products from the first glycosylation are then used as the aglycon for the next glycosyltransferase, (MtmII, encoded by mtmGII cloned from Streptomyces argillaceus (accession AAC64927)). Products from the second glycosylation are then used as the aglycon for the third glycosyltransferase, (MtmIII, encoded by mtmGIII cloned from Streptomyces argillaceus (accession AAC64927)). Products from the third glycosylation are then used as the aglycon for the fourth glycosyltransferase, (MtmIV, encoded by mtmGIV cloned from Streptomyces argillaceus (accession AAC64927)).

The nucleotide sugar library examined (see above under "Sugars") contains a few commercially available analogs, but is comprised primarily of synthetically generated derivatives. Jiang, J. et al. (2000); Jiang J. et al. (2001); Barton W. A., et al., "Structure, Mechanism and Active-Site Engineering of a Nucleotidylyltransferase: The First Step in the Glycorandomization of Natural Product-Based Metabolites," Nature Structural Biology (2001), manuscript in press; and U.S. Ser. No. 60/254,927. Each sugar is presented individually in a reaction separate from other sugars.

For each of the glycosyltransferases, 20 reactions are carried out, each with one of 20 different sugar phosphates). The anticipated library size will be the result of combining 20 different sugars at 5 different positions (each individually attached by the appropriate glycosyltransferase) on mithramycin to give $20_5$, or >3 million distinct mithramycin-based variants.

The resultant mixture is analyzed by HPLC ($C_{18}$, 0-40% $CH_3CN$/0.1% TFA, erythronolides observed at 285 nm). Novel compounds are identified. New peaks are isolated and characterized by HRMS. Stereo- and regiochemistry of the novel aureolic acids are determined based upon the known reactions catalyzed by MtmI-MtmIV.

Example 6

Antibiotic Optimization of Novel Vancomycin Analogs and Chemoglycorandomization

As an example of a glycosylated natural product, vancomycin (FIG. 6A, 33) from Amycolatopsis orientalis is a last defense against methicillin-resistant Gram-positive bacterial infections such as those caused by *Staphylococcus aureus* or *Enterococcus facecium*. Nicolaou, K. C., Boddy, C. N., Brase, S., Winssinger, N. *Angew. Chem. Int. Ed.* 38, 2096-2152 (1999).

The biosynthesis of vancomycin proceeds via a nonribosomal peptide synthase-catalyzed assembly of the aglycon (FIG. 6, 31), in parallel with an enzymatic synthesis of the necessary functionalized nucleotide diphosphosugars (NDP-sugars), and culminates in the glycosyltransferase-catalyzed transfer of two sugars, attached in a stepwise fashion as an L-vancosaminyl-1,2-D-glucosyl disaccharide, to the 4-hydroxyphenylglycine of the heptapeptide scaffold. Of the two vancomycin glycosyltransferases, GtfE is efficient at utilizing variant aglycons and NDP-sugar donors Hubbard, B. K., Walsh, C. T. *Angew. Chem.* 42, 730-765 (2003). Solenberg, P. J., Matsushima, P., Stack, D. R., Wilkie, S. C., Thompson, R. C. & Baltz, R. H. *Chem. Biol.* 4, 195-202 (1997); Losey, H. C., Peczuh, M. W., Chen, Z., Eggert, U. S., Dong, S. D., Pelczer, I., Kahne, D. & Walsh, C. T. *Biochemistry* 40, 4745-4755 (2001); Losey, H. C., Jiang, J., Biggins, J. B., Oberthur, M., Ye, X.-Y., Dong, S. D., Kahne, D., Thorson, J. S. & Walsh, C. T. *Chem. Biol.* 9, 1305-1314 (2002).

Methods for natural product glycosylation diversification were developed via in vitro chemo-enzymatic strategies to overcome many limitations associated with either total synthesis and/or in vivo pathway engineering (structural complexity, pathway bias, toxicity) and have developed methodology for the rapid chemoenzymatic synthesis of natural and 'unnatural' NDP-sugar libraries to test this hypothesis. Weymouth-Wilson, A. C. *Nat. Prod. Rep.* 14, 99-110 (1997); Thorson, J. S., Hosted Jr., T. J., Jiang, J., Biggins, J. B., Ahlert, J. & Ruppen, M. *Curr. Org. Chem.* 5, 139-167 (2001); Mendez, C., Salas, J. A. *Trends Biotechnol.* 19, 449-456 (2001). In the context of the known flexibility of secondary-metabolite associated glycosyltransferases (such as GtfE), these NDP-sugar libraries should provide the potential to generate 'glycorandomized' natural products. Furthermore, using in vitro glycorandomization (IVG), NDP-sugars bearing specifically reactive groups could be included to allow for the mild downstream diversification of the natural product via chemoselective ligation reactions. Hang, H. C., Bertozzi, C. R. *Acc. Chem. Res.* 34, 727-736 (2001); Kolb, H. C., Finn, M. G., Sharpless, K. B. *Angew. Chem. Int. Ed.* 40, 2004-2021. Overall, this strategy is advantageous in that it combines the diversity of chemical synthesis, the ease of regio- and stereo-specific enzymatic coupling of sugars to extremely complex aglycon structures, and the strength of chemoselective ligation to elaborate the final products.

To test the application of the first stage of IVG toward vancomycin, and expand upon previous GtfE substrate specificity studies, 23 natural and 'unnatural' NDP-sugars were individually tested as substrates for GtfE (FIG. 6B). Solenberg, P. J., Matsushima, P., Stack, D. R., Wilkie, S. C., Thompson, R. C. & Baltz, R. H. *Chem. Biol.* 4, 195-202 (1997); Losey, H. C., Peczuh, M. W., Chen, Z., Eggert, U. S., Dong, S. D., Pelczer, I., Kahne, D. & Walsh, C. T. *Biochemistry* 40, 4745-4755 (2001); Losey, H. C., Jiang, J., Biggins, J. B., Oberthur, M., Ye, X.-Y., Dong, S. D., Kahne, D., Thorson, J. S. & Walsh, C. T. *Chem. Biol.* 9, 1305-1314 (2002).

The general reaction was accomplished via incubation of the sugar-1-phosphate, dTTP, nucleotidylyltransferase ($E_p$) and inorganic pyrophosphatase for 2 hr, to generate the activated dTDP-sugar, followed by the addition of heptapeptide aglycon 31, GtfE and further incubation for at least 2 hr, to complete the transfer of the sugar from the dTDP-sugar to 31. After incubation, the filtrate was directly analyzed by high pressure liquid chromatography coupled to a mass spectrometer (LC-MS) which allowed for both identification and quantification of products. As illustrated in FIG. 6B, 21 from this set were accepted as substrates (>25% conversion). Prior to this work, the number of total monoglycosylated vancomycin analogs totalled 11 members constructed via multi-step chemical synthesis. Nicolaou, K. C., Cho, S. Y., Hughes, R., Winssinger, N., Smethurst, C., Labischinski, H. & Endermann, R. *Chem. Eur. J.* 7, 3798-3823 (2001). In conjunction with the smaller set of previously reported substrates for GtfE, the current number of monoglycosylated vancomycins produced by IVG totals 31 and clearly demonstrates the potential for rapidly expanding this stage I library. Losey, H. C., Jiang, J., Biggins, J. B., Oberthur, M., Ye, X.-Y., Dong, S. D., Kahne, D., Thorson, J. S. & Walsh, C. T. *Chem. Biol.* 9, 1305-1314 (2002). In addition, the 'unnatural' substrate 56 was previously shown to function with the second glycosyltransferase GtfD, which suggests further potential to build upon this stage I library by the enzymatic addition of vancosamine or, possibly, other sugars.

More importantly, glycoconjugates bearing reactive 'handles' such as compounds 50-54 from this small library present the opportunity to test stage II via novel chemoglycorandomization. Chemoselective ligation reactions among mutually and uniquely reactive functional groups in an aqueous environment have been used extensively in recent years for the modification of biopolymers and offer advantages similar to those of enzymatic reactions (efficiency, regio- and stereospecificity), with the advantage of a much broader range of coupling partners. Hang, H. C., Bertozzi, C. R. *Acc. Chem. Res.* 34, 727-736 (2001); Kolb, H. C., Finn, M. G., Sharpless, K. B. *Angew. Chem. Int. Ed.* 40, 2004-2021 (2001). One such reaction is the Huisgen 1,3-dipolar cycloaddition of azides and acetylenes to give 1,2,3-triazoles (FIG. 6C). Kolb, H. C., Finn, M. G., Sharpless, K. B. *Angew. Chem. Int. Ed.* 40, 2004-2021 (2001); Hlasta, D. J. & Ackerman, J. H. *J. Org. Chem.* 59, 6184-6189 (1994).

With unsymmetrical alkynes in this reaction, the ratio of 1,4- to 1,5-regio-isomers can be stringently controlled, via the addition of CuI, to give the 1,4-disubstituted 1,2,3-triazole Hlasta, D. J. & Ackerman, J. H. *J. Org. Chem.* 59, 6184-6189 (1994); Wang, Q., Chan, T. R., Hilgraf, R., Fokin, V. V., Sharpless, K. B. & Finn, M. G. *J. Am. Chem. Soc.* 125, 3192-3193 (2003). To test the feasibility of 1,3-dipolar addition toward the chemoselective diversification of vancomycin, the monoglycosylated variant 50 was incubated with a variety of alkynes followed by analysis of reaction progress via HPLC.

FIG. 6C illustrates the outcome of representative chemoselective ligations. Consistent with previous observations, terminal alkynes bearing electron withdrawing substituents generally reacted well in the presence of CuI while those lacking electron withdrawing groups were less efficient, with one exception, 5-hexyne-1-ol, which provided 67 at 65% conversion. For the non-terminal alkynes, one symmetrical (dimethyl acetylenedicarboxylate) and one asymmetrical (ethyl 4,4,4-trifluoro-2-butynoate) alkyne, both bearing strong electron withdrawing groups, were tested. Both reacted completely without CuI catalyst with the asymmetrical alkyne presenting a 1:1 mixture of 1,4- and 1,5-regio-isomers by HPLC (compounds 69a and 69b, respectively). In addition to commercially available alkynes, two modified alkynes bearing fluorescent tags (dabcyl propargyl imide and dansyl cadavarine propargyl imide) were synthesized and examined, both leading to the desired products (75 and 76, respectively). As representative negative controls, monoglycosylated variants lacking azidosugar moieties (vancomycin, 40, 55 and 56) showed no reaction upon incubation with alkynes under identical conditions. From this small pilot demonstration, the library of known monoglycosylated variants was increased to a total of 50 members bearing uniquely diverse functionality, further illustrating the significant potential of this approach toward natural product diversification. While 50 was selected for demonstration purposes, compounds 51-54 are also clear candidates for chemoselective ligation reactions as well.

Figure 7:
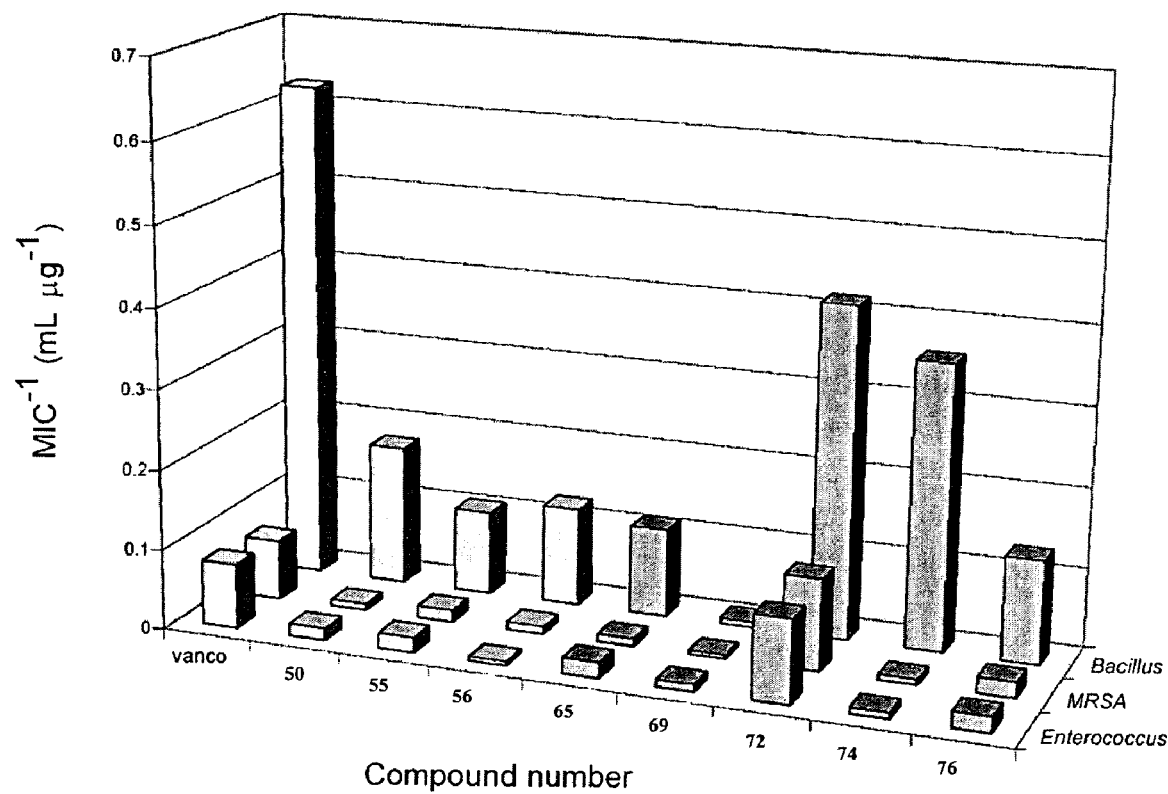
FIG. 7 provides antibiotic activity of selected library members.

To assess the utility of glycorandomization toward antibiotic optimization, random members (20%) of the glycorandomized library were submitted to antibacterial screens. The minimum inhibitory concentrations (MIC) against select Gram-positive strains (Bacillus, Staphylococcus and Enterococcus) are presented in FIG. 7. All previously tested monoglycosylated vancomycins were found to be significantly less potent than the parent vancomycin (ranging 4-10-fold). Nicolaou, K. C., Cho, S. Y., Hughes, R., Winssinger, N., Smethurst, C., Labischinski, H. & Endermann, R. Chem. Eur. J. 7, 3798-3823 (2001). Consistent with this, representative monoglycosylated derivatives 50, 55 and 56 from the stage I library were uniformly less active (~5-fold) than vancomycin. However, stage II chemoselective modification of 50 led to the discovery of a derivative (72) with notably enhanced properties. In particular, 72 was found to be slightly more active than vancomycin against both Staphylococcus and Enterococcus (~2-fold) but suprisingly, still less active (~2-fold) than vancomycin against Bacillus. Thus, 72 presents a clear organism-specificity not provided by the parent vancomycin. Moreover, the carboxylic acid substitution was found to be essential for the activity of 72 as 65 showed potencies similar to that of the underivatized monoglycosylated variants. While 72 somewhat contrasts the general belief that lipophilicity, with respect to vancomycin sugar substitution, enhances antibacterial properties, these results clearly support the significance of sugar substitution as a means to enhance desired properties. Nicolaou, K. C., Boddy, C. N., Brase, S., Winssinger, N. Angew. Chem. Int. Ed. 38, 2096-2152 (1999); Nicolaou, K. C., Cho, S. Y., Hughes, R., Winssinger, N., Smethurst, C., Labischinski, H. & Endermann, R. Chem. Eur. J. 7, 3798-3823 (2001); Ge, M.; Chen. Z.; Onishi, H. R.; Kohler, J.; Silver, L. L.; Kerns, R.; Fukuzawa, S.; Thompson, C.; Kahne, D. Science 284, 507-511 (1999).

This analysis also presented two additional derivatives (69 and 74) displaying distinct activity profiles in comparison to the monoglycosylated parent 50 or vancomycin. Given glycosyltransferases for the biosynthesis of many vital therapeutics are available and known to be promiscuous, the invention's results provide evidence that IVG is a useful approach for future drug development.

Following is a section describing the materials and method related to anitbiotic optimization via In Vitro glycorandomization: Table 1 illustrates reaction yields, retention times and MS characterization of 34-54 and 65-80.

TABLE 1

Stage I/II product characterization

| compound | Yield (%) | calculated mass | determined [M + H]+ | retention time (min) |
|---|---|---|---|---|
| 34 | 85 | 1304.3 | 1305.7 | 12.9 |
| 35 | 72 | 1345.4 | 1346.4 | 11.7 |
| 36 | 64 | 1345.4 | 1346.2 | 11.5 |
| 37 | 25 | 1271.4 | 1272.1 | 10.4 |
| 38 | 93 | 1304.3 | 1305.4 | 12.8 |
| 39 | 79 | 1345.4 | 1346.4 | 11.3 |
| 40 | 25 | 1287.4 | 1288.2 | 10.1 |
| 41 | 68 | 1304.3 | 1305.6 | 13.0 |
| 42 | 85 | 1274.3 | 1275.3 | 12.7 |
| 43 | 25 | 1329.4 | 1330.5 | 11.1 |
| 44 | 46 | 1304.3 | 1305.5 | 12.9 |
| 45 | 67 | 1304.3 | 1305.6 | 12.8 |
| 46 | 88 | 1304.3 | 1305.3 | 12.7 |
| 47 | 92 | 1318.4 | 1319.2 | 12.9 |
| 48 | 25 | 1313.4 | 1315.7 | 11.1 |
| 49 | 75 | 1272.4 | 1273.4 | 12.6 |
| 50 | 60 | 1329.3 | 1330.1 | 15.3 |
| 51 | 30 | 1329.3 | 1330.4 | 15.5 |
| 52 | 33 | 1329.3 | 1330.5 | 15.2 |
| 53 | 43 | 1329.3 | 1330.3 | 12.5 |
| 54 | 25 | 1288.1 | 1289.0 | 12.1 |
| 65 | 75 | 1413.4 | 1414.4 | 16.1 |
| 66 | 65 | 1455.4 | 1456.4 | 19.3 |
| 67 | 65 | 1427.4 | 1428.6 | 14.7 |
| 68 | 25 | 1421.4 | 1422.5 | 17.8 |
| 69a/b | 80 | 1495.4 | 1496.3 | 20.2/20.4 |
| 70 | 8 | 1452.5 | 1453.3 | 14.4 |
| 71 | 70 | 1471.4 | 1472.5 | 21.4 |
| 72 | 80 | 1399.4 | 1400.3 | 15.5 |
| 73 | 5 | 1517.4 | 1518.3 | 21.7 |
| 74 | 85 | 1555.5 | 1556.4 | 19.9 |
| 75 | 5 | 1635.5 | 1636.4 | 23.8 |
| 76 | 90 | 1716.5 | 1717.5 | 22.4 |
| 77 | 80 | 1461.4 | 1462.4 | 17.0/17.2 |
| 78 | 10 | 1397.4 | 1398.3 | 12.9 |
| 79 | 5 | 1445.4 | 1446.3 | 19.5 |
| 80 | 5 | 1398.4 | 1399.3 | 10.5 |

Sugar phosphates employed were prepared chemically as previously described or via the following methods. Jiang et al., J. Am. Chem. Soc. 122, 6803-6804 (2000); Jiang et al., Angew. Chem. Intl, Ed. Engl. 40, 1502-1505 (2001); Barton et al., Nat. Struct. Biol. 8, 545-551 (2001); Barton et al., Proc. Natl. Acad. Sci. U.S.A. 99, 13397-13402 (2002); Albermann et al., ChemBioChem 4, 443-446 (2003); Nagarajan et al, J. Chem. Soc. Chem. Commun. 1306-1307 (1988).

$E_p$ and GtfE were expressed and purified as previously described. Losey, H. C., Jiang, J., Biggins, J. B., Oberthur, M., Ye, X.-Y., Dong, S. D., Kahne, D., Thorson, J. S. & Walsh, C. T. Chem. Biol. 9, 1305-1314 (2002). Vancomycin aglycon 31 was prepared by selective hydrolysis of vancomycin in trifluoroacetic acid at room temperature for 5 hr. All other enzymes and reagents were directly purchased from Sigma or Aldrich. LC-MS analysis was accomplished on an Agilent 1100 HPLC-MSD SL quadrupole mass spectrometer containing a photodiode array detector.

General NDP-sugar Synthesis ($E_p$ Reaction)

A solution containing 4.2 mM sugar phosphate, 4.5 mM dTTP, 250 U $E_p$, 40 U inorganic pyrophosphatase in 50 mM Tris-HCl (pH 8.0), 10 mM $MgCl_2$ was incubated at 37° C. for 2 hr. An aliquot of the reaction was diluted with an equal volume of MeOH followed by removal of precipitated proteins via centrifugation (12,000×g) and direct analysis of product formation via HPLC-MS as previously described.

General Aglycon Glycosylation (GtfE Reaction)

Figure 1:
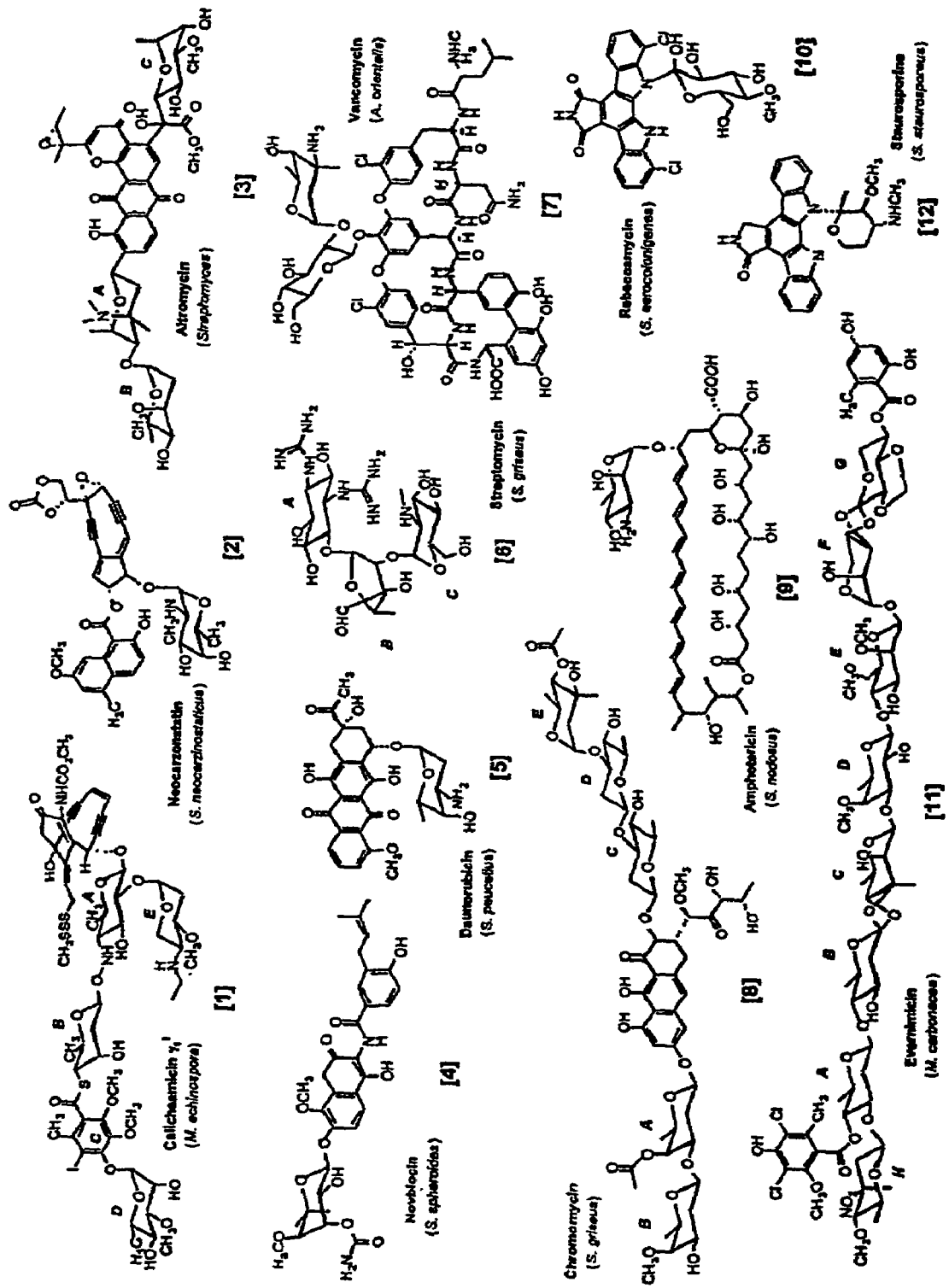
FIG. 1 provides chemical structures of several bioactive metabolites.

An appropriate volume of the $E_p$ reaction solution to present 2 mM NDP-sugar, 1 mM vancomycin aglycon, 20 U GtfE, 400 µg BSA in 75 mM Tricine-NaOH (pH 9.0) was incubated at 37° C. for at least 2 hr. An aliquot of the reaction was diluted with an equal volume of MeOH followed by removal of precipitated proteins via centrifugation (12,000× g) and direct analysis of product formation via LC-MS. Analytical HPLC utilized a Phenomenex Luna $C_{18}$ (250×4.6 mm, 5µ analytical column; A: 0.1% TFA, B: $CH_3CN$; stepwise gradient of 5-15% B over 15 min followed by 15-96% B in 10 min; 1 mL min$^{-1}$; $A_{282}$). Under these conditions, the typical retention times for monoglycosylated variants ranged from 10-15 min, while aglycon 1 eluted at 18 min. Reaction yields, retention times and MS characterization for compounds illustrated in FIG. 1B is provided in Table S1.

Chemoselective Ligation (1,3-dipolar cycloaddition)

A reaction to generate 50 was diluted 2-fold with MeOH, centrifuged (12,000×g) concentrated in vacuo to 20 µl. Compound 50 was subsequently purified via preparative reverse phase HPLC. Preparative HPLC utilized a Supelco Discovery BIO $C_{18}$ (250×10 mm, 5µ analytical column; A: 0.1% TFA, B: $CH_3CN$; stepwise gradient of 5-15% B over 15.3 min followed by 15-96% B in 10 min; 4 mL min$^{-1}$; $A_{282}$). The desired product, which eluted at 15 min, was collected, frozen, lyophilized and stored at −20° C. in the absence of light until dipolar cycloaddition.

To a solution containing 50 (0.16 µmol) in 40 µl of MeOH or $H_2O$:DMSO (4:1), was added 32 µmol of alkyne and 0.8 µmol of CuI, followed by heating to 70° C. Upon completion, an aliquot of the reaction mixture (5 µl) was diluted with 500 µl of MeOH:$H_2O$ (1:1), filtered (Waters Oasis HLB 1 cc extraction cartridge), diluted with acetic acid (10 µl) and analyzed via LC-MS. Under these conditions, the typical retention times for the modified monoglycosylated variants ranged from 10-25 min. Reaction yields, retention times and MS characterization for compounds illustrated in FIG. 6C is provided in Table 1.

Bioassays

The reaction mixture from 1,3-dipolar cycloaddition was centrifuged and 20 µl directly submitted for antibacterial screens (ACI Pharm Inc., 292 5$^{th}$ Ave., New York, N.Y., 10001) against six indicator strains—*Bacillus subtilis* (ATCC 6633), methicillin resistant *Staphylococcus aureus* (ZYABL 006), *Entercoccus faecalis* (ATCC 29212), *Pseudomonas aeruginosa* (ATCC 27853), *Klebsiella pneumoniae* (ATCC 10031) and *Escherichia coli* (ATCC 25922). For each chemoselective ligation sample submitted, the corresponding alkyne negative controls (750 mM) showed no antibacterial effect. For FIG. 7, serial dilutions (16 µg mL$^{-1}$-0.06 µg mL$^{-1}$) of compounds were screened in 96-well tissue culture plate growth assays as assessed by both turbidity and $A_{630}$. The reported MIC is the lowest concentration of antibiotic that completely inhibits bacterial growth by both detection methods.

Synthesis and Compound Characterization 2,4,6-Tri-acetyl-3-azido-3-deoxy-α-D-glucopyranosyl bromide. 1,2,4,6-Tetra-O-acetyl-3-azido-3-deoxy-α-D-glucopyranoside (430 mg, 1.02 mmol) was dissolved in a mixture of 30 mL $CH_2Cl_2$ and 3 mL EtOAc. Titanium tetrabromide (725 mg, 1.97 mmol) was added and the reaction mixture was stirred at room temperature for 3 days. The reaction was quenched with NaOAc (730 mg) and the suspension diluted with 150 mL $CH_2Cl_2$, extracted with water (30 mL), the organic layer dried over $Na_2SO_4$, filtered and evaporated. The resulting crude residue was purified by silica gel chromatography (4:1 hexane-EtOAc), to give the desired product in pure form (348 mg, 76.7%). $^1$H NMR (CDCl$_3$) 6.62 (d, 1H, $J_{1,2}$=4.0 Hz), 5.05 (t, 1H, J=10.0 Hz), 4.70 (dd, 1H, J =4.0, 10.0 Hz), 4.27 (dd, 1H, J=4.4, 12.4 Hz), 4.20 (m, 1H), 4.09 (t, J=10.4 Hz), 4.08 (m, 1H) 2.18, 2.15, and 2.10 (3 s, 9H). $^{13}$C NMR (CDCl$_3$) 170.44, 169.43, 169.02, 87.02, 72.13, 71.43, 66.86, 61.29, 60.88, 20.59, 20.53.

3-Methoxy-2-pyridyl-3-azido-3-deoxy-2,4,6-tri-O-acetyl-β-D-glucopyranoside. A mixture of 2,4,6-tri-O-acetyl-3-azido-3-deoxy-α-D-glucopyranosyl bromide and silver 3-methoxy-2-pyridoxide in 10 mL anhydrous toluene was refluxed for 1 hr. The mixture was filtered over celite, washed with $CH_2Cl_2$, and concentrated. Purified by flash chromatography on silica gel (hexane-EtOAc, gradient of 2:1 to 1:1) gave desired purified product in 80% yield. $^1$H NMR (CDCl$_3$) (dd, J=0.8, 4.4, Hz, 1H), 7.12 (dd, J=1.2, 8 Hz, 1H), 6.95 (dd, J=4.8, 8.0 Hz), 6.20 (d, J=7.6 Hz, 1H), 5.31 (dd, J=8.0, 10.0 Hz, 1H), 5.11 (t, J=10.0 Hz, 1H), 4.23 (dd, J=4.4, 12.4 Hz, 1H), 4.12 (dd, J=3.2, 10.0 Hz, 1H), 3.9 (m, 1H), 3.83 (s, 3H), 3.77 (t, J=10.0 Hz, 1H), 2.09 (s, 3H), 2.06 (s, 3H), 2.04 (s, 3H); $^{13}$C NMR (CDCl$_3$) 170.67, 169.16, 168.97, 151.62, 144.33, 136.66, 119.43, 119.10, 93.68, 73.01, 70.69, 68.17, 64.45, 61.72, 20.65, 20.62, 20.58. MS: cal;cd for $C_{18}H_{22}N_4O_9Na$ 461.1, found m/z 461.0 (M+Na)$^+$.

3-Azido-3-deoxy-α-D-glucose-1-phosphate. To a mixture of crystalline phosphoric acid (373 mg, 3.8 mmol) and 3-methoxy-2-pyridyl-3-azido-3-deoxy-β-D-glucopyranoside (170 mg, 0.545 mmol) was added 2 mL of anhydrous DMF. The reaction mixture was stirred at room temperature for three hours, then neutralized with saturated barium hydroxide followed by removal of precipitated barium phosphate by centrifugation. The supernatant was concentrated and the residue submitted to an anion exchange chromatography (Dowex 1×8, 1.2×12 cm) eluted with 100 mL water, 100 mL 0.1M $NH_4HCO_3$, 100 mL 0.2 $NH_4HCO_3$, and 100 mL 0.3M $NH_4HCO_3$. The product eluted with 0.2 M $NH_4HCO_3$ and these fractions were pooled and co-evaporated with ethanol several times to remove $NH_4HCO_3$. The product containing fractions were collected and lyophilized to give 85 mg sodium salt (62%). $^1$H NMR (D$_2$O) 5.37 (dd, J=3.2, 7.6 Hz, 1H), 3.87 (ddd, J=2.0, 4.8, 9.6 Hz, 1H), 3.78 (dd, J=2.0, 12.0 Hz, 1H), 3.71 (dd, J=10.0 Hz, 1H), 3.68 (dd, J=12.0, 4.8 Hz, 1H), 3.47 (m, 1H), 3.38 (t, J =10.0 Hz, 1H); $^{13}$C NMR (D$_2$O) 93.39, 72.14, 71.23, 68.71, 66.28, 60.69; $^{31}$P NMR (D$_2$O) 3.07. MS: calcd for $C_6H_{11}N_3O_8P^-$ 284.1, found m/z 284.0.

2,3,6-Tri-O-acetyl-4-azido-4-deoxy-α-D-glucopyranosoyl bromide. 1,2,3,6-Tetra-O-acetyl-4-azido-4-deoxy-α-D-glucopyranoside (1.56 g, 4.18 mmol) was dissolved in a mixture of 60 mL $CH_2Cl_2$ and 6 mL EtOAc. Titanium tetrabromide (2.35 g, 6.4 mmol) was added and the reaction mixture was stirred at room temperature for 3 days. The reaction was quenched with NaOAc (2.35 g), the suspension diluted with 250 mL of $CH_2Cl_2$ and extracted with water (30 mL), The organic layer was dried over $Na_2SO_4$, filtered and evaporated, and the residue was purified by silica gel chromatography (4:1 hexane:EtOAc) to give 895 mg of the desired product (74.5%). $^1$H NMR (CDCl$_3$) 6.55 (d, J=4 Hz, 1H), 5.59 (t, J=10.0 Hz, 1H), 4.79 (dd, J=4.0, 10.0 Hz, 1H), 4.40 (dd, J =2.4, 12.8 Hz, 1H), 4.33 (dd, J=4.0, 12.8 Hz, 1H), 4.06 (m, 1H, H-5), 3.71 (t, J=10.0 Hz, 1H), 2.14 (s, 3H), 2.13 (S, 3H), 2.10 (s, 3H); $^{13}$C NMR (CDCl$_3$) 170.55, 170.15, 169.63, 86.63, 72.70, 70.85, 70.77, 62.14, 59.48, 20.96, 20.88; MS: calcd for $C_{12}H_{16}BrN_3O_7Na$ 417.1, found m/z 417.0 (M+Na).

3-Methoxy-2-pyridyl 4-azido-4-deoxy-2,3,6-tri-O-acetyl-β-D-glucopyranoside. A mixture of 2,3,6-tri-O-acetyl-4-azido-4-deoxy-α-D-glucopyranosyl bromide (840 mg, 2.163 mmol) and silver 3-methoxy-2-pyridoxide (830 mg) in 35 mL anhydrous toluene was refluxed for 1 h. The mixture was filtered over celite, washed with $CH_2Cl_2$, concentrated, and purified by flash chromatography on silica gel (hexane:EtOAc 2;1-1:1) to give 744 mg of the desired product (75%). $^1$H NMR ($CDCl_3$) 7.70 (dd, J=1.6, 4.8 Hz, 1H), 7.11 (dd, J=1.6, 8.0 Hz, 1H), 6.95 (dd, J=4.8, 8.0 Hz, 1H), 6.23 (d, J=8.0 Hz, 1H, H-1), 5.31 (m, 2H), 4.39 (dd, J=2.4, 12.4 Hz, 1H, H-6), 4.28 (dd, J=4.0, 12.4 Hz, H-6), 3.83 (s, 3H), 3.77 (m, 1H), 3.70 (m, 1H), 2.13 (s, 3H), 2.08 (s, 3H), 1.98 (s, 3H); $^{13}$C NMR ($CDCl_3$) 170.73, 170.18, 169.80, 151.70, 144.25, 137.04, 119.49, 119.33, 93.60, 74.18, 72.69, 71.35, 62.90, 60.13, 56.11, 20.96, 20.92, 20.82. calcd for $C_{18}H_{22}BrN_4O_9Na$ 461.1, found m/z 461.0 (M+Na).

4-Azido-4-deoxy-α-D-glucose-1-phosphate. To a mixture of crystalline phosphoric acid (1.12 g, 11.4 mmol) and 3-methoxy-2-pyridyl 4-azido-4-deoxy-β-D-glucopyranoside (490 mg, 1.57 mmol) was added 3 mL of anhydrous DMF. The reaction mixture was stirred at room temperature for three hours then neutralized with saturated barium hydroxide. The precipitated barium phosphate was removed by centrifugation and washed with water. Supernatant and washings were subsequently combined, concentrated, and purified via anion exchange (Dowex 1×8, 1.2×12 cm) eluted with 100 mL water, 100 mL 0.1M $NH_4HCO_3$, 100 mL 0.2 $NH_4HCO_3$, and 100 mL 0.3M $NH_4HCO_3$. The product eluted with 0.2 M $NH_4HCO_3$ and these fractions were pooled and co-evaporated with ethanol several times to remove $NH_4HCO_3$. The obtained sugar phosphate ammonium salt was subsequently dissolved in 5 mL of water and applied to an AG-X8 cation-exchange column ($Na^+$ type), eluted with 100 mL water. The product containing fractions were collected and lyophilized to give 268 mg sodium salt (60.3%). MS: calcd for $C_6H_{11}N_3O_8$ 284.1, found m/z 284.3 (M+H)$^-$.

2,3,4-Tri-O-acetyl-6-azido-6-deoxy-α-D-glucopyranosoyl bromide. 1,2,3,4-Tetra-O-acetyl-6-azido-6-deoxy-α-D-glucopyranoside (665 mg, 1.78 mmol) was dissolved in a mixture of 30 mL $CH_2Cl_2$ and 3 mL EtOAc. Titanium tetrabromide (981 mg, 62.67 mmol) was added and the reaction mixture was stirred at room temperature for 3 days. NaOAc (980 mg) was added to quench the reaction and the suspension was diluted with 150 mL of $CH_2Cl_2$ and extracted with water (30 mL). The organic layer was dried over $Na_2SO_4$, filtered and evaporated and the residue purified by silica gel chromatography (4:1 hexane-EtOAc) to give 380 mg of the desired product (86%). $^1$H NMR ($CDCl_3$) 6.63 (d, J=4.0 Hz, 1H), 5.55 (t, J=9.6 Hz, 1H), 5.15 (t, J=9.0, Hz, 1H), 4.83 (dd, J =4.0, 9.6 Hz, 1H), 4.27 (m, 1H, H-5), 3.50 (dd, J=2.8, 13.6 Hz, 1H), 3.37 (dd, J=13.6, 5.2 Hz, 1H), 2.10 (s, 3H), 2.08 (S, 3H), 2.06 (s, 3H); $^{13}$C NMR($CDCl_3$) 169.79, 169.66, 169.36, 86.05, 72.96, 70.48, 69.94, 68.16, 50.17, 20.54, 20.53, 20.49; MS: calcd for $C_{12}H_{16}BrN_3O_7$ Na 417.1, found m/z 417.0 (M+Na).

3-Methoxy-2-pyridyl 6-azido-6-deoxy-2,3,4-tri-O-acetyl-β-D-glucopyranoside. A mixture of 2,3,4-tri-O-acetyl-6-azido-6-deoxy-α-D-glucopyranosyl bromide (370 mg, 0.94 mmol) and silver 3-methoxy-2-pyridoxide (400 mg) in 25 ml anhydrous toluene was refluxed for 1 h. The mixture was filtered over celite, washed with $CH_2Cl_2$, and concentrated. Purification by flash chromatography on silica gel (hexane-EtOAc 2;1 to 1:1), gave 338 mg of the desired product (82%). $^1$H NMR ($CDCl_3$) 7.73 (dd, J=1.2, 5.2 Hz, 1H), 7.12 (dd, J=1.2, 7.6 Hz, 1H), 6.95 (dd, J=4.8, 8.0 Hz, 1H), 6.27 (d, J =7.6 Hz, 1H), 5.35 (m, 2H), 5.10 (t, J=9.2 Hz, 1H), 3.93 (m, 1H), 3.40 (dd, J=6.8, 13.6 Hz, 1H), 3.25 (dd, J=2.8, 13.6 Hz, 1H), 2.06 (s, 3H), 2.04 (s, 3H), 1.00 (s, 3H); $^{13}$C NMR ($CDCl_3$) 170.22, 169.53, 169.27, 151.54, 144.32, 136.97, 119.50, 119.14, 93.49, 73.67, 72.96, 70.82, 69.56, 55.98, 50.90, 20.60; calcd for $C_{18}H_{22}BrN_4O_9Na$ 461.1, found m/z 461.0 (M+Na).

6-azido-6-deoxy-α-D-glucose-1-phosphate. To a mixture of crystalline phosphoric acid (0.52 g, 5.3 mmol) and 3-methoxy-2-pyridyl 6-azido-6-deoxy-β-D-glucopyranoside (134.3 mg, 0.43 mmol) was added 2 mL of anhydrous DMF. The reaction mixture was stirred at room temperature for three hours, then neutralized with saturated barium hydroxide. The precipitated barium phosphate was removed by centrifugation and washed with water and the supernatant and washings were combined and concentrated. The residue was dissolved in small amount of water and submitted to an anion exchange column (Dowex 1×8, 1.2×12 cm) eluted with 100 mL water, 100 mL 0.1M $NH_4HCO_3$, 100 mL 0.2 $NH_4HCO_3$, 100 mL 0.3M $NH_4HCO_3$. The product eluted with 0.2 M $NH_4HCO_3$ and these fractions were pooled and co-evaporated with ethanol several times to remove $NH_4HCO_3$. The obtained sugar phosphate ammonium salt was subsequently dissolved in 5 mL of water and applied to an AG-X8 cation-exchange column ($Na^+$ type), eluted with 100 mL water. The product containing fractions were collected and lyophilized to give 48 mg sodium salt (60.3%). $^1$H NMR ($D_2O$): 5.42 (dd, J=3.6, 7.6 Hz, 1H), 3.97 (m, 1H), 3.73 (t, J=7.2 Hz, 1H), 3.64 (dd, J=2.8, 13.6 Hz, 1H), 3.58 (dd, J=4.0, 13.6 Hz, 1H), 3.48 (ddd, J=2.0, 3.6, 9.6 Hz, 1H), 3.44 (t, J=9.6 Hz, 1H); $^{13}$C NMR ($CDCl_3$) 94.22, 73.07, 72.20, 70.94, 70.38, 51.06; $^{31}$P NMR ($D_2O$) 2.33 MS: calcd for $C_6H_{11}N_3O_8$ 284.1, found m/z 284.2 (M+H)$^-$.

Example 7

Figure 8:
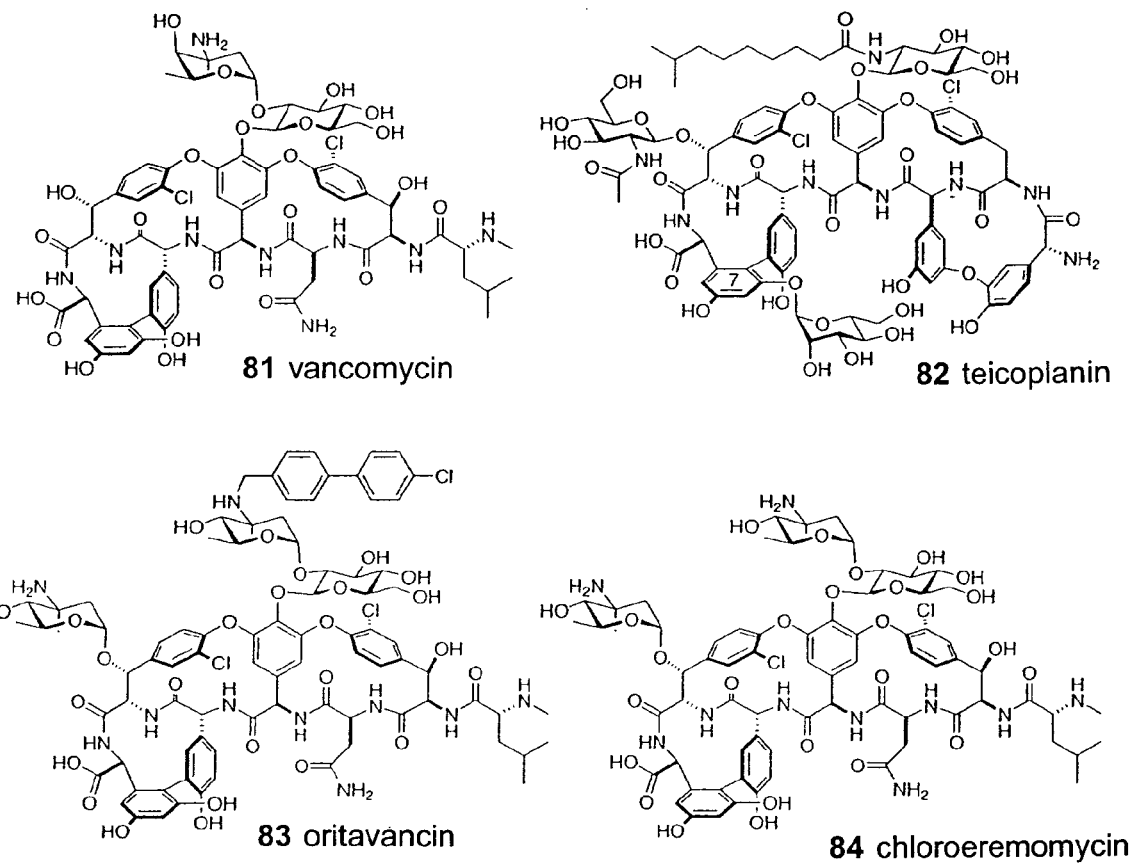
FIG. 8: provides structures of Vancomycin, Teicoplanin, Oritavancin, Chloroeremomycin

Analogs of the glycopeptide antibiotics vancomycin (81) and teicoplanin (82) (FIG. 8) with alterations in one or both sugar moieties of the disaccharide have been prepared by tandem action of the vancomycin pathway glycosyltransferases GtfE and GtfD. All four regioisomers (2-, 3-, 4-, 6-) of TDP-deoxyglucoses and UDP/TDP-aminoglucoses were prepared, predominantly by action of D-glucopyranosyl-1-phosphate thymidylyltransferase, $E_p$. GtfE transferred the deoxyglucoses or aminoglucoses onto the 4-OH of 4-hydroxyphenylglycine of both the vancomycin and teicoplanin aglycone scaffolds. Kinetic analysis indicated the 2-, 3-, 4-, and 6-amino-glucoses were transferred by GtfE with only a 10-30 fold drop in $k_{cat}$ and no effect on $K_m$ compared to the native substrate, UDP/TDP-glucose, suggesting preparative utility. The next enzyme, GtfD, could utilize the variant glucosyl-peptides as substrates for transfer of L-4-epi-vancosamine. The aminosugar moieties in these variant glycopeptides introduced sites for acylation or reductive alkylation.

Chemical Synthesis of UDP-Glucose Derivatives

Six glucose-1-phosphate analogs were coupled to the nucleotide uridine monophosphate to produce three analogs replacing the position 2 hydroxyl of glucose with fluoro, azido, and amino groups (UDP-2-fluoro-glucose, UDP-2-azido-glucose, and UDP-2-amino-glucose) and three analogs replacing the position 6 hydroxyl of glucose (UDP-6-chloro-glucose, UDP-6-azido-glucose, UDP-6-amino-glucose) as potential substrates for GtfE and the aglycones of teicoplanin or vancomycin. The synthetic approach to generate these compounds is shown in FIG. 9. Starting with the corresponding acetylated lactols (85a, 85b, 89a-c), the 3,4-acetoxy sugar-1-phosphates (86a, 86b, 90a-c) were generated by phosphorylation, and subsequent coupling using UMP-morpholidate resulted in the six UDP-glucose derivatives (87a, 87b, 88, 91a, 91b, 92), with overall yields between 18-32 percent (FIG. 9), Wittmann V, Wong C-H. 1H-Tetrazole as Catalyst in Phosphoromorpholidate Coupling Reactions: Efficient Synthesis of GDP-Fucose, GDP-Mannose, and UDP-Galactose. J Org Chem 1997;62:2144-2147. The purity and identity of each compound were verified by mass spectrometry (EI) and $^1$H-, $^{13}$C-, and $^{31}$P-NMR (data not shown).

Chemoenzymatic Synthesis of TDP-Glucose Derivatives.

Figure 10:
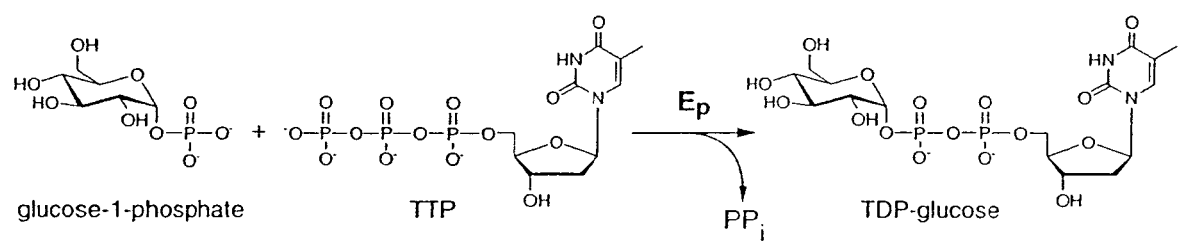
FIG. 10: provides a scheme for $E_p$-mediated synthesis of TDP-glucose

In parallel to the chemical syntheses noted above the inventors evaluated the ability of the thymidylyl transferase $E_p$ to take a variety of D-glucose-1-P derivatives for thymidylyl transfer catalysis (FIG. 10), building on prior efforts that suggested relaxed specificity could be expected, Jiang J, Biggins J B, Thorson J S. A General Enzymatic Method for the Synthesis of Natural and 'Unnatural' UDP- and TDP-Nucleotide Sugars. J Am Chem Soc 2000;122: 6803-6804, Jiang J, Biggins J B, Thorson J S. Expanding the Pyrimidine Diphosphosugar Repertoire: The Chemoenzymatic Synthesis of Amino- and Acetamidoglucopyranosyl Derivatives. Angew Chem Int Ed Engl 2001;40(8):1502-1505. In the deoxy series, the 2-, 3-, 4-, and 6-deoxyglucose-1-phosphate species were prepared as previously described, and were shown to be thymidylylated by $E_p$ to the TDP-sugar products as evaluated by HPLC analysis (data not shown), Jiang J, Biggins J B, Thorson J S. Expanding the Pyrimidine Diphosphosugar Repertoire: The Chemoenzymatic Synthesis of Amino- and Acetamidoglucopyranosyl Derivatives. Angew Chem Int Ed Engl 2001;40(8):1502-1505. Under the incubation conditions noted in the experimental section, the inventors observed 70-100 percent conversion to 4- and 6-deoxy-glucosyl-TDP species, while the TDP-2-deoxy-glucose was generated in only about 10 percent yield, and TDP-3-deoxy-glucose was generated in about 30 percent yield. In incubations for subsequent reaction with GtfE and aglycones, this resulted in 250 µM TDP-2-deoxy-glucose in the GtfE reaction, 0.75 mM TDP-3-deoxy-glucose, and approximately 2 mM solutions of TDP-4-deoxy-glucose and TDP-6-deoxy-glucose. The double variant glucose derivative, TDP-4-amino-6-deoxy-glucose was also made using $E_p$-mediated conversion of the corresponding sugar-1-phosphate in 80-90 percent yield resulting in a final concentration of 2 mM in subsequent incubations with GtfE.

Since the chemical coupling noted above gave UDP-2-amino-glucose and UDP-6-amino-glucose, the inventors prepared the other two regiosiomers enzymatically as the TDP-sugars by $E_p$-mediated conversions of 3-amino-glucose-1-phospate and 4-amino-glucose-1-phosphate to produce TDP-3-amino-glucose and TDP-4-amino-glucose in 80-90% yields in the three hour incubations, Jiang J, Biggins J B, Thorson J S. Expanding the Pyrimidine Diphosphosugar Repertoire: The Chemoenzymatic Synthesis of Amino- and Acetamidoglucopyranosyl Derivatives. Angew Chem Int Ed Engl 2001;40(8):1502-1505. Large scale incubations were performed to generate 18 mg of TDP-3-amino-glucose and 3.5 mg of TDP-4-amino-glucose after purification for further studies to determine kinetic parameters with GtfE.

Thus all four regioisomers of TDP-deoxyglucose and NDP-aminoglucose, as well as the doubly variant TDP-4-amino-6-deoxy-glucose and the 6-desmethyl-glucose, UDP-xylose (FIG. 11), were available for testing as sugar donors for GtfE catalysis.

Figure 11:
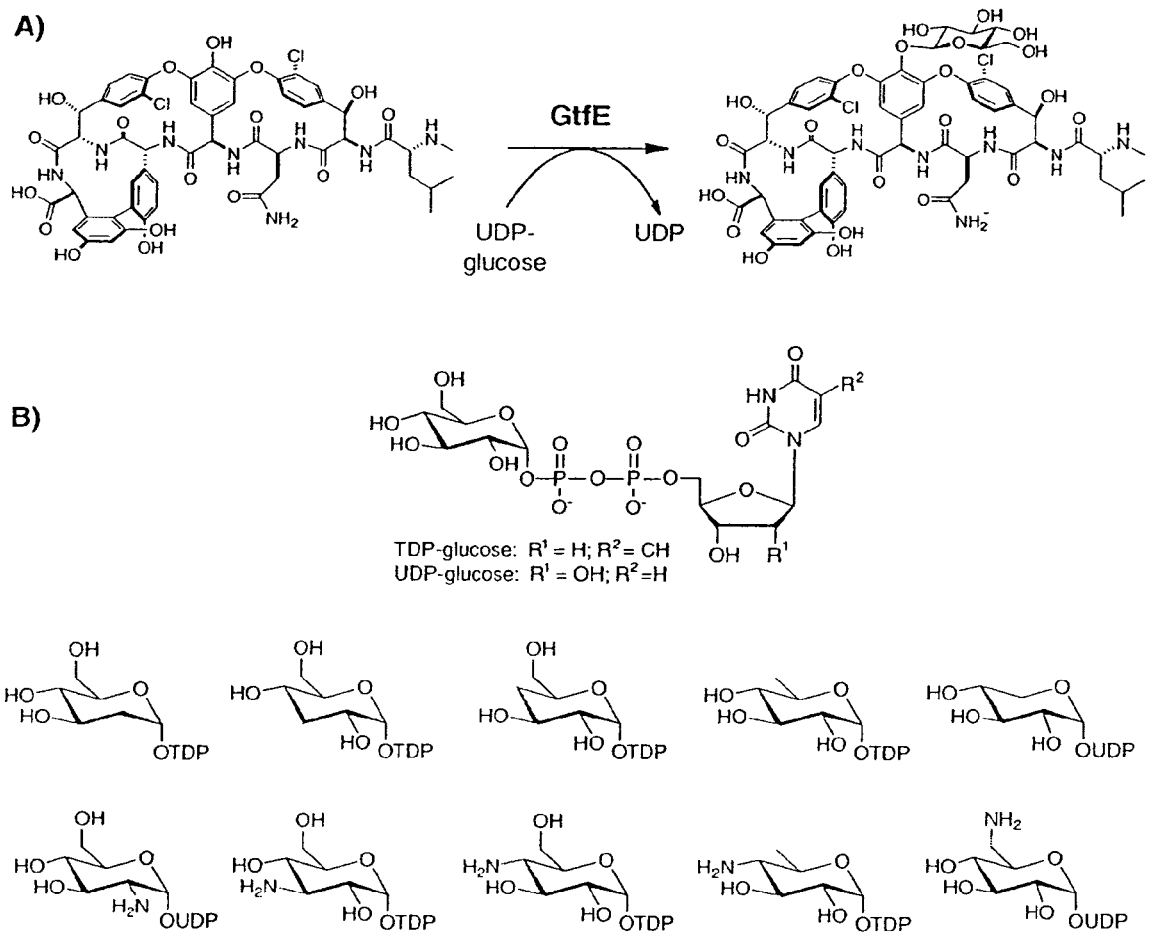
FIG. 11 provides GtfE recognition and transfer of alternate nucleotide-sugar donors onto the heptapeptide acceptor substrate (A) Reaction pathway of GtfE (B) Deoxy- and amino-derivatives of NDP-glucose tested
Figure 12:
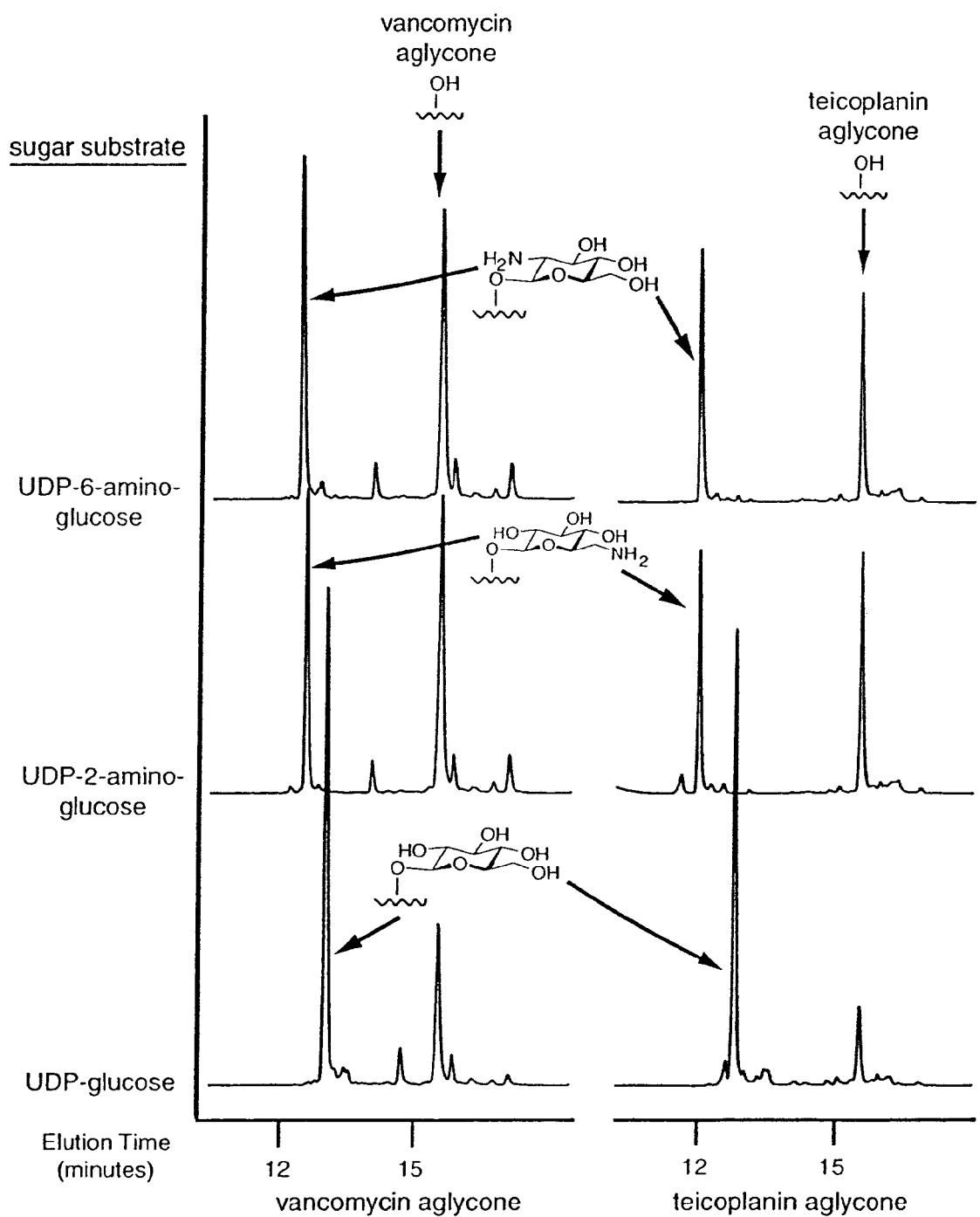
FIG. 12: provides transfer of aminoglucoses by GtfE (A) HPLC traces of glucose, 2-amino-glucose, and 6-amino-glucose being transferred to vancomycin aglycone. Mass spectrometry results for 2-amino-glucosyl-AGV calculated [M+H$^+$]=1304.4, observed [M+H$^+$]=1304.5, for 6-amino-glucosyl-AGV, calculated=1304.4, observed=1304.5. (B) HPLC traces of glucose, 2-amino-glucose, and 6-amino-glucose being transferred to teicoplanin aglycone. Mass spectrometry results for 2-amino-glucosyl-AGT calculated [M+H$^+$]=1359.4, observed [M+H$^+$]=1359.5, for 6-amino-glucosyl-AGV, calculated=1359.4, observed=1359.4.

Transfer of Glucose Derivatives by GtfE to the Vancomycin and Teicoplanin Aglycones The ten UDP- and TDP-glucose derivatives shown in FIG. 11, as well as UDP-2- and 6-azido-glucose, UDP-2-fluoro-glucose, and UDP-6-chloro-glucose were assayed as substrates for pure GtfE with both its native aglycone heptapeptide substrate (AGV=vancomycin aglycone) and also with the teicoplanin aglycone (AGT=teicoplanin aglycone), which differs in amino acids 1 and 3. Glycosylated peptide products were first analyzed by HPLC, and new peaks were corroborated for molecular weight by Maldi-TOF mass spectrometry. Each of the nucleotide sugar substrates shown in FIG. 11B could be recognized and the sugar moiety transferred by GtfE to the vancomycin and teicoplanin scaffolds as analyzed by HPLC and mass spectrometry, while UDP-2-azido-, UDP-2-fluoro-, and UDP-6-azido-glucose proved inadequate for transfer by GtfE. In FIG. 12, representative HPLC traces are shown using the donor sugar substrates UDP-glucose, UDP-2-amino-glucose, and UDP-6-amino-glucose, showing glycosyl transfer to both the vancomycin and teicoplanin aglycone acceptor substrates. $K_m$ and $k_{cat}$ data for selected NDP-sugar substrates with GtfE are collected in Table 2. (The acceptor substrate, the vancomycin aglycone, was held constant at 1 mM in each experiment.)

TABLE 2

Steady-state kinetic parameters for purified NDP-glucose derivatives

| Substrate[a] | $K_m$ (mM) | $k_{cat}$ (min$^{-1}$) | $k_{cat}/K_m$ (mM$^{-1}$ min$^{-1}$) | Relative $k_{cat}/K_m$ |
|---|---|---|---|---|
| UDP-glucose | 0.72 ± 0.11 | 31 ± 2 | 43 | 1 |
| TDP-glucose | 0.62 ± 0.09 | 29 ± 2 | 47 | 1/0.9 |
| UDP-2-NH$_2$-glucose | 0.79 ± 0.08 | 2.7 ± 0.2 | 3.4 | 1/13 |
| TDP-3-NH$_2$-glucose | 0.72 ± 0.06 | 3.6 ± 0.2 | 5 | 1/9 |
| TDP-4-NH$_2$-glucose | 1.1 ± 0.1 | 1.3 ± 0.1 | 1.2 | 1/36 |
| UDP-6-NH$_2$-glucose | 1.2 ± 0.2 | 1.5 ± 0.2 | 1.3 | 1/33 |
| UDP-xylose | 1.8 ± 0.2 | 7.9 ± 0.5 | 4.4 | 1/10 |
| UDP-6-Cl-glucose | 21 ± 6 | 0.3 ± 0.1 | 0.014 | 1/3100 |

First, both UDP-glucose and TDP-glucose as substrates have equal catalytic efficiency ($k_{cat}/K_m$), indicating that GtfE is not fastidious about the 5-methyl of thymine or the 2'-hydroxyl of ribose versus deoxyribose. This permissivity towards the NDP moiety allows cross comparison of the other UDP- and TDP-glucose analogs. The 6-desmethyl (xylose) and the 6-chloromethyl group in UDP-6-chloro-glucose are tolerated at about 10 and less than 0.1 percent catalytic efficiency, respectively. All $K_m$ and $k_{cat}$ data were gathered using the vancomycin aglycone as the acceptor substrate. The four regioisomeric TDP-deoxyglucoses also served as substrates and could be transferred not only to the vancomycin scaffold but also the teicoplanin scaffold. For example, as shown in panel B of FIG. 13, the 4-deoxy-glucosyl-AGT product (95) could be accumulated and detected by HPLC analysis of GtfE incubations with AGT and TDP-4-deoxy-glucose. TDP-2-fluoro-glucose was not detectably processed by GtfE, perhaps due to the electronic effects of 2-F on the reactivity at the adjacent $C_1$.

$K_m$ and $k_{cat}$ data were obtained for all four regioisomers of NDP-aminoglucose reacting with the vancomycin aglycone scaffold and are shown in Table 2. GtfE is remarkably permissive for the amino group at carbons 2, 3, 4, and 6 of the glucose ring, with all four NDP-aminoglucoses having equivalent $K_m$ values (0.7-1.2 mM) and also a narrow range of $k_{cat}$ values (1.3-3.6 min$^{-1}$). Compared to the authentic glucosyl donor substrate, TDP- or UDP-glucose, the 10-40 fold reduction in catalytic efficiency with the four regioisomeric NDP-aminoglucoses is almost entirely a $k_{cat}$ effect. The $pK_a$ of the amine of the aminoglucoses has been reported to be between 7.75-9, Niemietz C, Hauer R, Hofer M. Active transport of charged substrates by a proton/sugar co-transport system. Amino-sugar uptake in the yeast *Rhodotorula gracilis*. Biochem J 1981;194(2):433-41, Sem D S, Cleland W W. Phosphorylated aminosugars: synthesis, properties, and reactivity in enzymatic reactions. Biochemistry 1991;30(20):4978-84, Since the reactions are all carried out at pH 9, which is at or above the $pK_a$ of the aminoglucose substrates, it is not yet known whether GtfE transfers the aminoglucose moiety with a protonated amine or as the free base. Regardless, the ability of GtfE to transfer sugars with an amine displayed at many points of the hexose ring periphery indicated that this combination of enzyme and nucleotide sugars would be a useful platform for evaluation of the next glycosyltransferase, GtfD.

Activity of the Second Glycosyltransferase GtfD: Transfer of L-4-epi-vancosaminyl Groups to the Glucosylpeptide Variants The deoxyglucosyl- and aminoglucosyl-heptapeptide products from GtfE incubations could thus be evaluated as substrates for the next enzyme, GtfD, the L-vancosaminyltransferase, involved in the maturation of late stage biosynthetic intermediates of the vancomycin pathway. The natural sugar donor is presumed to be TDP-L-β-vancosamine, where vancosamine is a trideoxy-3-methyl-3-amino-hexose. This TDP sugar is not available for study. However, the inventors have reported both the biosynthesis of the 4-epi form, TDP-L-β-4-epi-vancosamine, by action of five purified enzymes EvaA-E, from the biosynthetic operon in the chloroeremomycin producer, and also the chemical synthesis of the α/β anomeric mixture of UDP-L-4-epi-vancosamine, Losey H C, Peczuh M W, Chen Z, Eggert U S, Dong S D, Pelczer I, et al. Tandem action of glycosyltransferases in the maturation of vancomycin and teicoplanin aglycones: novel glycopeptides. Biochemistry 2001;40(15): 4745-55, Chen H, Thomas M G, Hubbard B L, Losey H C, Walsh C T, Burkart M D. Deoxysugars in glycopeptide antibiotics: enzymatic synthesis of TDP-L-epivancosamine in chloroeremomycin biosynthesis. Proc Natl Acad Sci USA 2000;97(22): 11942-7. The latter material was available for use in tandem incubations of GtfE and GtfD.

The tandem action of GtfE and GtfD was attempted using TDP-4-amino-glucose and GtfE in the first stage and UDP-L-4-epi-vancosamine and GtfD in the second stage (FIG. 13A). The heptapeptide scaffold used in this case was the vancomycin aglycone, and GtfE action resulted in transfer of 4-amino-glucose (93). The product of GtfE and GtfD action was 4-epi-vancosaminyl-(1,2)-4-amino-glucosyl-AGV (94), containing a 1,2-disaccharide moiety with two amino sugars (FIG. 13A). The tandem incubation of GtfE and GtfD combines to yield a derivative of vancomycin with an alteration in each of the two sugars: an amine derivative of glucose and a position 4 epimer of vancosamine.

Tandem incubations of GtfE and GtfD were also carried out on the teicoplanin aglycone scaffold. As exemplified in the right hand column of FIG. 13B, incubation commenced with GtfE and TDP-4-deoxy-glucose to yield 4-deoxy-glucosyl-AGT (95). The second stage involved UDP-L-epi-vancosamine as the donor substrate and GtfD as the catalyst to produce the novel teicoplanin analog 4-epi-vancosaminyl-(1,2)-4-deoxy-glucosyl-AGT (96), two sugars which are not normally found appended to the teicoplanin heptapeptide scaffold. Both the heptapeptide scaffold and the two sugars in the disaccharide moiety differ in the two glycopeptide variants shown in FIG. 13.

Analogous incubations demonstrated that the inventors were able to generate derivatives of the vancomycin disaccharide containing 3-, 4-, and 6-deoxyglucoses and 3-, 4-, and 6-aminoglucoses, as well as 4-amino-6-deoxyglucose attached to both the vancomycin and teicoplanin heptapeptide scaffolds (data not shown). Each new product detected by HPLC was subsequently analyzed by Maldi-TOF mass spectrometry to verify mass.

Discussion

In the naturally occurring glycopeptide antibiotics the sugars matter: to some extent in determining potency, to a large extent in increasing solubility, to increase dimerization constants, and to restrict conformational flexibility of the aglycone scaffold, Grdadolnik S G, Pristovsek P, Mierke D F. Vancomycin: conformational consequences of the sugar substituent. J Med Chem 1998;41(12):2090-9, Kannan R, Harris C H, Harris T M, Waltho J P, Skelton N J, Williams D H. Function of the amino sugar and N-terminal amino acid of the antibiotic vancomycin in its complexation with cell wall peptides. J Am Chem Soc 1988;110:2946-2953, Mackay J P, Gerhard U, Beauregard D A, Maplestone R A, Williams D H. Dissection of the contributions toward dimerization of glycopeptide antibiotics. J Am Chem Soc 1994; 116:4573-4580. The amino groups in the aminohexose moieties of both teicoplanin (glucosamine), 82, and oritavancin (4-epi-vancosamine), 83, are sites for either natural acylation (teicoplanin) or semisynthetic alkylation (oritavancin), modifications that improve activity against Vancomycin Resistant *Enterococci* (VRE). The ability to generate additional aminosugar variants of glycopeptides would be of particular interest.

As is typical in many glycopeptide and glycosylated polyketide biosynthetic clusters, the genes for producing the dedicated aminodeoxysugars and the glycosyltransferases that use the TDP-aminodeoxysugars as donors are integral orfs in those gene clusters. Otten S L, Liu X, Ferguson J, Hutchinson C R. Cloning and characterization of the *Streptomyces peucetius* dnrQS genes encoding a daunosamine biosynthesis enzyme and a glycosyl transferase involved in daunorubicin biosynthesis. J Bacteriol 1995; 177(22):6688-92, Volchegursky Y, Hu Z, Katz L, McDaniel R. Biosynthesis of the anti-parasitic agent megalomicin: transformation of erythromycin to megalomicin in *Saccharopolyspora erythraea*. Mol Microbiol 2000;37(4):752-62, Pelzer S, Sussmuth R, Heckmann D, Recktenwald J, Huber P, Jung G, et al. Identification and analysis of the balhimycin biosynthetic gene cluster and its use for manipulating glycopeptide biosynthesis in *Amycolatopsis mediterranei* DSM5908. Antimicrob Agents Chemother 1999;43(7):1565-73. Our prior efforts have validated the function of eight such orfs in chloroeremomycin biosynthetic cluster [8, 16], encoding five enzymes for conversion of TDP-4-keto-6-deoxy-glucose to TDP-L-4-epi-vancosamine, and three enzymes that attach TDP-glucose or TDP-L-4-epi-vancosamine at three sites to complete antibiotic maturation, Losey H C, Peczuh M W, Chen Z, Eggert U S, Dong S D, Pelczer I, et al.

Tandem action of glycosyltransferases in the maturation of vancomycin and teicoplanin aglycones: novel glycopeptides. Biochemistry 2001;40(15):4745-55, Chen H, Thomas M G, Hubbard B L, Losey H C, Walsh C T, Burkart M D. Deoxysugars in glycopeptide antibiotics: enzymatic synthesis of TDP-L-epivancosamine in chloroeremomycin biosynthesis. Proc Natl Acad Sci USA 2000;97(22): 11942-7. Likewise the inventors have established that GtfD and GtfE, cloned from the vancomycin producer and purified after heterologous expression in *Escherichia coli*, act in tandem to generate the disaccharyl chain of vancomycin.

In this study the inventors began with assay of the glucosyltransferase, GtfE, that adds the first sugar, a D-glucosyl unit, to the phenolic oxygen of the 4-hydroxyphenylglycine residue at position four of the crosslinked heptapeptide aglycone scaffold of vancomycin, Losey H C, Peczuh M W, Chen Z, Eggert U S, Dong S D, Pelczer I, et al. Tandem action of glycosyltransferases in the maturation of vancomycin and teicoplanin aglycones: novel glycopeptides. Biochemistry 2001;40(15):4745-55. The inventors have focused initially on the four regioisomeric deoxyglucoses and the four corresponding aminoglucose isomers, given the occurrence of deoxy and amino substitutions in the natural sugar chains of glycopeptide antibiotics, Nicolaou K C, Boddy C N, Brase S, Winssinger N. Chemistry, Biology, and Medicine of the Glycopeptide Antibiotics. Angew Chem Int Ed Engl 1999;38(15):2096-2152. The inventors also evaluated the 6-chloro, and 2- and 6-azido versions of UDP-glucose because of their potential for subsequent chemical elaboration to additional derivatives after GtfE or GtfE/D tandem action. None of the latter three UDP-sugars were robust substrates for GtfE. Likewise, UDP-2-fluoro-glucose was not recognized, probably due to inductive deactivation at the adjacent $C_1$ position.

Figure 13:
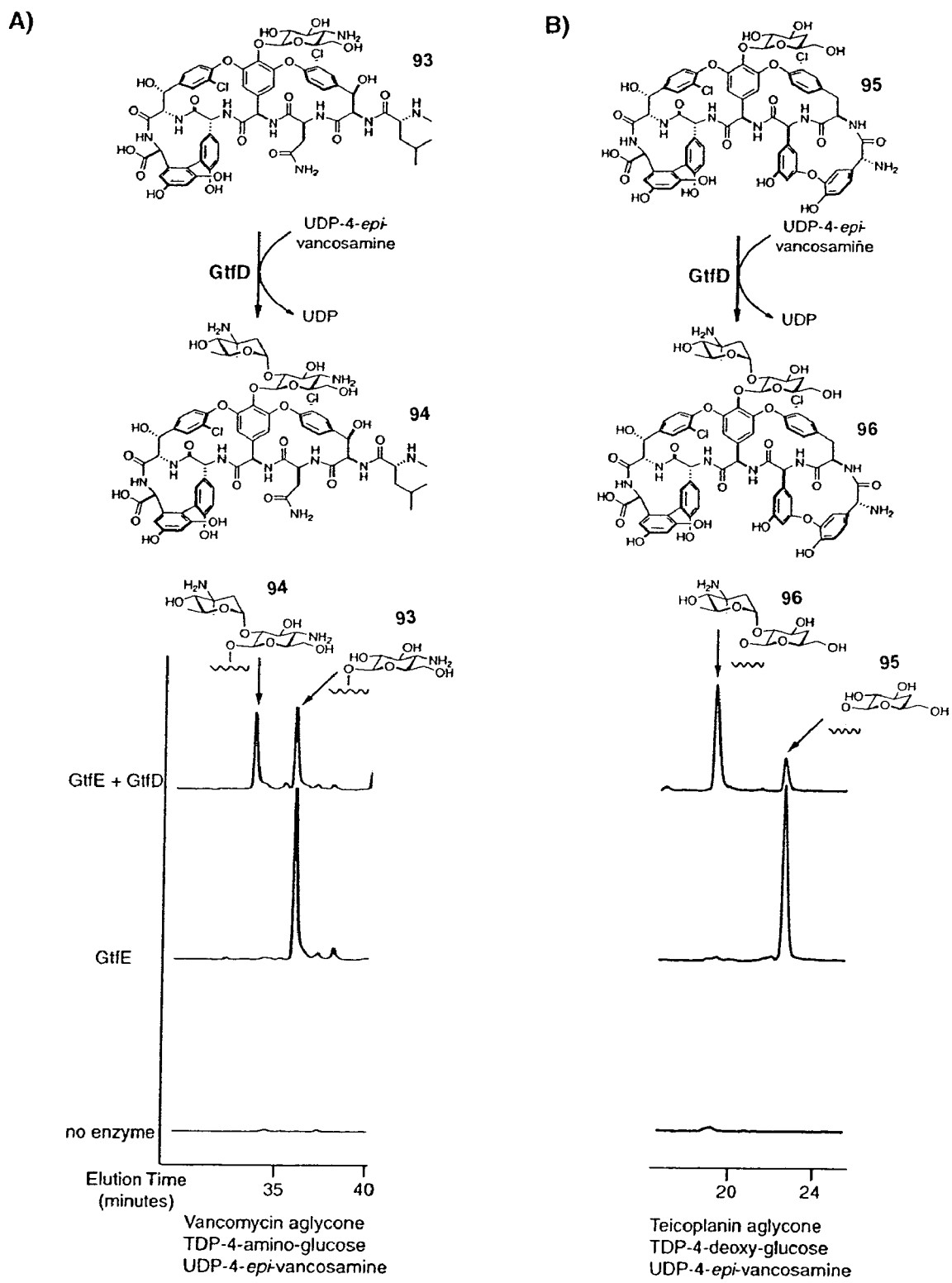
FIG. 13 provides recognition of modified scaffolds by GtfD (A) Reaction pathway of 4-epi-vancosaminylation by GtfD of the vancomycin scaffold with 4-amino-glucose attached, and the corresponding HPLC traces with no enzyme, GtfE alone (4-amino-glucosyl-AGV, calculated [M+H]=1304.4, observed=1304.4), or GtfE+D (4-amino-epivancomycin, calculated [M+H]=1446.4, observed=1446.4). (B) Reaction pathway of 4-epi-vancosaminylation by GtfD of the teicoplanin scaffold with 4-deoxy-glucose attached, and the corresponding HPLC traces with no enzyme, GtfE alone (4-deoxy-glucosyl-AGT, calculated [M+H]=1344.3, observed=1344.4), or GtfE+D (4-epi-vancosaminyl-4-deoxy-glucosyl-AGT, calculated [M+H]=1487.4, observed=1487.4).

The 2-, 3-, 4-, and 6-deoxy-glucosyl-AGV products from GtfE action could provide differential elements of hydrophobic surface patches on the sugar and might be of use in combinations to modulate solubility properties of such glycopeptide variants. Of these four isomers the 2-deoxy-glucosyl-AGV would be a dead end product vis a vis further elongation since the 2-OH of the glucose moiety is the nucleophile in the next reaction, the vancosaminyl/4-epi-vancosaminyl transfer by GtfD or GtfC to create the (4-epi)-vancosaminyl-(1,2)-glucosyl linkage. The inventors have demonstrated as shown in FIG. 13 that the subsequent enzyme GtfD is sufficiently promiscuous that it can indeed transfer 4-epi-vancosamine to a vancomycin scaffold with a 4-deoxy-glucose moiety in lieu of glucose.

The regioisomeric aminoglucoses attached to both the vancomycin and teicoplanin scaffolds are particularly interesting since the amino groups are chemical handles for both natural acylation and synthetic reductive alkylation to produce lipoglycopeptides. In teicoplanin, 82, it is the 2-aminoglucose moiety that is enzymatically acylated. In oritavancin, 83, the only amino group in the disaccharide moiety is in the distal sugar, the 4-epi-vancosamine, in which the amine is at position 3 of the hexose ring, which is the site of chlorobiphenyl alkylation to gain activity against VRE. The ability to move the amino group around the glucose ring to all four available positions and append to the vancomycin or teicoplanin scaffold will allow subsequent acylation to probe any differences in efficacy from differential placement of the fatty acyl chain, Dong S D, Oberthur M, Losey H C, Anderson J W, Eggert U S, Peczuh M W, et al. The structural basis for induction of VanB resistance. J Am Chem Soc 2002;In press. On the vancomycin scaffold, the 2-aminoglucose is likely to be incompetent for subsequent chain elongation by GtfE since that would generate a bridging —NH group to the terminal vancosamine sugar and no activity was detected with GtfD. The other three sites, 3-amino, 4-amino, and 6-amino, are permissive for elongation and should allow site-specific alkylation/acylation for subsequent evaluation of potency and spectrum against both sensitive and resistant enterococci, as well as a broader range of Gram-positive bacterial pathogens.

Experiments investigating tandem action of GtfE, then GtfD, were successful, indicating that amino- or deoxy-hybrid disaccharide chains can be built on both aglycone scaffolds. FIG. 13 shows that both the 4-amino-glucosyl-AGV and the 4-deoxy-glucosyl-AGT could be elongated by transfer of 4-epi-vancosamine by action of GtfD. Preparatively useful amounts should be obtainable for subsequent acylation and/or reductive alkylation to test for improved antibacterial properties. The 4-epi-vancosaminyl-4-amino-glucosyl-AGV (94) is representative of a new subclass of vancomycin/teicoplanin hybrids with two amino groups in the disaccharide and selective alkylation/acylation chemistry should be possible to evaluate the utility of double substitution against both antibiotic-sensitive and resistant bacteria.

Analogous experiments showed that heptapeptide scaffolds with 3-, 4-, and 6-deoxyglucose and 3-, 4-, and 6-amino-glucose attached could be further elongated with 4-epi-vancosamine by GtfD. In addition the doubly variant 4-amino-6-deoxy-glucose could also be elongated by GtfD, suggesting that both GtfE and GtfD can tolerate more than a single change. These experiments suggest that the vancomycin glycosyltransferases are very good candidates for use in combinatorial biosynthesis of glycopeptide antibiotics.

The Gtfs that carry out the last stages of glycopeptide antibiotic maturation are promising reagents for introduction of structural versatility on complex aglycone scaffolds. To implement this approach further requires four things. First is an expanded library of TDP-D-glucose analogs, where the $E_p$ thymidylyltransferase with its engineered relaxation of specificity towards glucose-1-phosphate derivatives should be a particularly useful reagent, Barton W A, Lesniak J, Biggins J B, Jeffrey P D, Jiang J, Rajashankar K R, et al. Structure, mechanism and engineering of a nucleotidylyl-transferase as a first step toward glycorandomization. Nat Struct Biol 2001;8(6):545-51, Thorson J S, Hoster T J, Jiang J, Biggins J B, Ahlert J. Nature's carbohydrate chemists: the enzymatic glycosylation of bioactive bacterial metabolites. Curr Org Chem 2001;5:139-167, Barton W A, Biggins J B, Jiang J, Thorson J S, Nikolov D B. Expanding an 'unnatural' pyrimidine diphophosugar library via nucleotidyltransferase engineering. Proc Natl Acad Sci USA 2002;in press. Second will be a library of TDP-L-vancosamine analogs. Because the sugar is of the L-configuration and because the biosynthesis of TDP-L-sugars are invariably multiple enzymatic steps from TDP-D-glucose, a chemical approach to libraries of TDP-L-hexoses may be the shorter path, Chen H, Thomas M G, Hubbard B L, Losey H C, Walsh C T, Burkart M D. Deoxysugars in glycopeptide antibiotics: enzymatic synthesis of TDP-L-epivancosamine in chloroeremomycin biosynthesis. Proc Natl Acad Sci USA 2000;97(22): 11942-7, Liu H W, Thorson J S. Pathways and mechanisms in the biogenesis of novel deoxysugars by bacteria. Annu Rev Microbiol 1994;48:223-56. The three most common biochemically-generated substituents that tailor the hexose backbones are deoxy, amino, and C- and N-methyl groups, and these would be good starting elements in synthetic TDP-L-hexose libraries. The third requirement would be for additional variants of the crosslinked aglycone scaffolds as starting substrates for glycosylation. These could include backbone alterations such as those found in the complestatin aglycone, O-sulfation found in the naturally occurring A47934 antibiotic of the teicoplanin family and selective semisynthetic alterations at the N-and C-termini of the heptapeptide scaffold, such as found in dalbavancin, Chiu H T, Hubbard B K, Shah A N, Eide J, Fredenburg R A, Walsh C T, et al. Molecular cloning and sequence analysis of the complestatin biosynthetic gene cluster. Proc Natl Acad Sci USA 2001;98 (15):8548-53, Solenberg P J, Matsushima P, Stack D R, Wilkie S C, Thompson R C, Baltz R H. Production of hybrid glycopeptide antibiotics in vitro and in *Streptomyces toyocaensis*. Chem Biol 1997;4(3):195-202, Pootoolal J, Thomas M G, Marshall C G, Neu J M, Hubbard B K, Walsh C T, et al. Assembling the glycopeptide antibiotic scaffold: The biosynthesis of A47934 from *Streptomyces toyocaensis* NRRL15009. Proc Natl Acad Sci USA 2002;99(13):8962-7, Steiert M, Schmitz F J. Dalbavancin (Biosearch Italia/Versicor). Curr Opin Investig Drugs 2002;3(2):229-33. The fourth requirement would be for a broader set of Gtfs. These could come from as yet uncloned glycopeptide biosynthetic clusters that would put in the other aminodeoxy sugars found in this class of natural products, such as L-acosamine or L-ristosamine. Nicolaou K C, Boddy C N, Brase S, Winssinger N. Chemistry, Biology, and Medicine of the Glycopeptide Antibiotics. Angew Chem Int Ed Engl 1999; 38(15):2096-2152. Alternatively, recent advances in structure determination of GtfB and the related MurG might suggest productive reengineering approaches to broaden glycosyl transfer capacity, Mulichak A M, Losey H C, Walsh C T, Garavito R M. Structure of the UDP-glucosyltransferase GtfB that modifies the heptapeptide aglycone in the biosynthesis of vancomycin group antibiotics. Structure (Camb) 2001;9(7):547-57, Ha S, Walker D, Shi Y, Walker S. The 1.9 Å crystal structure of *Escherichia coli* MurG, a membrane-associated glycosyltransferase involved in peptidoglycan biosynthesis. Protein Sci 2000;9(6):1045-52.

Finally, libraries of TDP-D-hexoses and TDP-L-hexoses would also be useful substrate collections for Gtfs that transfer glycosyl groups to nonpeptidic aglycones such as the 14 and 16 membered polyketide macrolactones, deoxyerythronolactone and tylactone on the way to erythromycin and tylosin, as well as the polycyclic polyketide aglycones, e.g. in the mithramycin and daunomycin families, Otten S L, Liu X, Ferguson J, Hutchinson C R. Cloning and characterization of the *Streptomyces peucetius* dnrQS genes encoding a daunosamine biosynthesis enzyme and a glycosyl transferase involved in daunorubicin biosynthesis. J Bacteriol 1995;177(22):6688-92, Steiert M, Schmitz F J. Dalbavancin (Biosearch Italia/Versicor). Curr Opin Investig Drugs 2002;3(2):229-33, Mulichak A M, Losey H C, Walsh C T, Garavito R M. Structure of the UDP-glucosyltransferase GtfB that modifies the heptapeptide aglycone in the biosynthesis of vancomycin group antibiotics. Structure (Camb) 2001;9(7):547-57, Ha S, Walker D, Shi Y, Walker S. The 1.9 Å crystal structure of *Escherichia coli* MurG, a membrane-associated glycosyltransferase involved in peptidoglycan biosynthesis. Protein Sci 2000;9(6):1045-52, Gaisser S, Bohm G A, Doumith M, Raynal M C, Dhillon N, Cortes J, et al. Analysis of eryBI, eryBIII and eryBVII from the erythromycin biosynthetic gene cluster in *Saccharopolyspora erythraea*. Mol Gen Genet 1998;258(1-2):78-88, Gandecha A R, Large S L, Cundliffe E. Analysis of four tylosin biosynthesis genes from the tylLM region of the *Streptomyces fradiae* genome. Gene 1997; 184(2):197-203, Blanco G, Fernandez E, Fernandez M J, Brana A F, Weissbach U, Kunzel E, et al. Characterization of two glycosyltransferases involved in early glycosylation steps during biosynthesis of the antitumor polyketide mithramycin by *Streptomyces argillaceus*. Mol Gen Genet 2000;262(6):991-1000.

The inventors have used a combination of chemical and chemoenzymatic approaches to generate a library of nucleotide sugar substrates for glycosyltransferases from the vancomycin biosynthetic operon in order to evaluate the potential for combinatorial biosynthesis within the glycopeptide class of antibiotics. They have demonstrated the ability to incorporate numerous analogs of NDP-glucose onto the heptapeptide scaffolds of both vancomycin and teicoplanin, including all four regioisomeric deoxy- and aminoglucoses, using the glucosyltransferase GtfE. In addition, subsequent elaboration of the modified glucosylpeptides with 4-epi-vancosamine by the vancosaminyltransferase, GtfD, generated vancomycin and teicoplanin derivatives with variant disaccharides. The ability to incorporate all four regioisomeric aminoglucoses allows for subsequent selective modification of the amine by chemical acylation or reductive alkylation, which has been shown to increase activity against vancomycin-resistant *enterococci* as exemplified by the semisynthetic glycopeptide oritavancin. The ability to append disaccharides with two amino-sugars onto the vancomycin and teicoplanin scaffolds, for example the vancomycin heptapeptide with the disaccharide 4-epi-vancosamine-(1,2)-4-amino-glucose attached, provides two sites for subsequent chemical modification and increases the potential to discover derivatives that are active against vancomycin-resistant *enterococci*. The observed relaxed specificity of the vancomycin glycosyltransferases GtfE and GtfD demonstrates the potential for combinatorial biosynthesis within the glycopeptide class of antibiotics. Synthesis of UDP-2-amino-glucose, UDP-2-azido-glucose, UDP-2-fluoro-glucose, UDP-6-amino-glucose, UDP-6-azido-glucose, and UDP-6-chloro-glucose.

The different UDP-glucose derivatives were prepared starting from the corresponding acetylated lactols (FIG. 9), which were obtained from the anomeric acetates by cleavage with hydrazine acetate in DMF, Ambrose M G, Binkley R W. Synthesis of deoxyhalogeno sugars. Reaction of halide ions, with 1,2,3,4-tetra-O-acetyl-6-O-[(trifluoromethyl)sulfonyl]-beta-D-glucopyranose. J Org Chem 1983;48(674-677), Haradahira T, Maeda M, Kai Y, Omae H, Kojima M. Improved synthesis of 2-deoxy-2-fluoro-D-glucose using fluoride ion. Chem Pharm Bull 1985;33:165-172, Mehta S, Meldal M, Ferro V, Duus J O, Bock K. Internally quenched fluorogenic, alpha-helical dimeric peptides and glycopeptides for the evaluation of the effect of glycosylation on the conformation of peptides. J Chem Soc, Perkins Trans 1 1997:1365-1374, Pavliak V, Kovac P. A short synthesis of 1,3,4,6-tetra-O-acetyl-2-azido-2-deoxy-beta-D-glucopyranose and the corresponding alpha-glucosyl chloride from D-mannose. Carbohydr Res 1991;210:333-7, Silva D J, Wang H, Allanson N M, Jain R K, Sofia M J. Stereospecific solution- and solid-phase glycosylations. Synthesis of beta-linked saccharides and construction of disaccharide libraries using phenylsulfenyl 2-deoxy-2-trifluoroacetamido. The 2-azido and 6-azido lactols (85a and 85b) were coupled with dicyanoethyl diisopropylphosphoramidite with tetrazole in dichloromethane ($CH_2Cl_2$) and oxidized to the protected 1-phosphates with 3-chloroperbenzoic acid (mCPBA) in $CH_2Cl_2$ (−40-0° C.). Removal of the cyanoethyl groups was achieved by treatment with tetramethyl guanidine (TMG) and chlorotrimethylsilane (TMSCl) in acetonitrile ($CH_3CN$) at room temperature for one hour Gaffney P R J, Reese C B. Synthesis of naturally occurring phosphatidylinositol 3,4,5- trisphosphate [PtdIns(3,4,5)P3] and its diastereoisomers. J Chem Soc, Perkins Trans 1 2001:192-205. The 3,4-acetoxy sugar-1-phosphates (86a and 86b) were coupled with UMP-morpholidate, using tetrazole as a catalyst in pyridine at room temperature for 48 h. Deacetylation ($Et_3N$/MeOH/$H_2O$, 1:2:2 for 24 h) gave UDP-2-azido-glucose (87a) and UDP-6-azido-glucose (87b), respectively. Hydrogenation ($H_2$, Pd—C) for 4 h in methanol of the 87b yielded UDP-6-amino-glucose (88) (FIG. 9A).

For synthesis of the 6-chloro, 2-fluoro and 2-amino UDP-glucose derivatives, a slightly modified reaction scheme was followed (FIG. 9). Coupling of the 6-chloro and 2-fluoro lactols (89a and 89b), and 2-N-trifluoroacetyl lactol (89c) with dibenzyl diisopropylphosphoramidite with tetrazole in $CH_2Cl_2$, oxidation with mCPBA in $CH_2Cl_2$ (−40-0° C.), and hydrogenation of the benzyl groups ($H_2$, Pd—C) for 4 h in methanol afforded the 3,4-acetoxy sugar-1-phosphates (90a, 90b, and 90c). Deacetylation with NaOMe in methanol for 1 h gave an anomeric mixture of phosphates, which was coupled with UMP-morpholidate using tetrazole as a catalyst in pyridine at room temperature for 48 h to give UDP-6-chloro-glucose (91a), UDP-2-fluoro-glucose (91b), and UDP-2-N-TFA-glucose (91c). UDP-2-amino-glucose (92) was obtained from 91c following removal of the trifluoroacetoyl protecting group with $Et_3N$/MeOH/$H_2O$ (1:2:2) for 24 h (FIG. 9B), Wittmann V, Wong C-H. 1H-Tetrazole as Catalyst in Phosphoromorpholidate Coupling Reactions: Efficient Synthesis of GDP-Fucose, GDP-Mannose, and UDP-Galactose. J Org Chem 1997;62:2144-2147. For all compounds, identity and purity were verified by $^1H$-, $^{13}C$-, and $^{31}P$-NMR, and mass spectrometry (EI).

Chemoenzymatic Synthesis of TDP-deoxy- and TDP-aminoglucose Derivatives by $E_p$.

The procedure for the enzymatic conversion of glucose-1-phosphate to TDP-glucose by the $E_p$ enzyme has been described previously, as has the ability of $E_p$ to accept many derivatives of glucose-1-phosphate for catalysis, Jiang J, Biggins J B, Thorson J S. A General Enzymatic Method for the Synthesis of Natural and 'Unnatural' UDP- and TDP-Nucleotide Sugars. J Am Chem Soc 2000;122:6803-6804; and Jiang J, Biggins J B, Thorson J S. Expanding the Pyrimidine Diphosphosugar Repertoire: The Chemoenzymatic Synthesis of Amino- and Acetamidoglucopyranosyl Derivatives. Angew Chem Int Ed Engl 2001;40(8):1502-1505. $E_p$ was purified as previously described, and 2-, 3-, 4-, and 6-deoxy- and amino-glucose-1-phosphates, as well a 4-amino-6-deoxy-glucose-1-phosphate were synthesized as before. The in vitro reactions were carried out as previously described, except glucose-1-phosphate derivative concentrations were 5 mM, TTP concentration was 5 mM, and 5 units of inorganic pyrophosphatase were used in each reaction. Reaction progress was monitored by HPLC ($A_{260}$) using an Alltech Strong Anion Exchange (SAX) column (250×4.6 mm) and a linear gradient of 50-250 mM potassium phosphate, pH 5 over 20 minutes.

Large scale incubations were carried out in order to make and purify TDP-3- and 4-amino-glucose. A 25 mL enzymatic reaction containing 25 mg 3-amino-glucose-1-phosphate at a final concentration of 3.8 mM was incubated for 3 h at 37° C. Once the reaction reached 75 percent completion as monitored by SAX HPLC (see above), it was quenched by addition of 25 mL cold methanol. After centrifugation, the supernatant was concentrated and then lyophilized. After resuspension in 0.5 mL water, the mixture was chromatographed on a 10 g silica gel column with 1:1 methanol:ammonium hydroxide as the eluent. Fractions were analyzed by silica gel thin layer chromatography using the same eluent, and detected by UV. Fractions containing TDP-3-amino-glucose were pooled and concentrated. SAX HPLC and $^{31}P$-NMR analysis were used to verify the purity of the sample.

A 3.2 mL $E_p$ reaction containing 3 mg 4-amino-glucose-1-phosphate at a final concentration of 3.5 mM was incubated for 2 h at 37° C. and quenched with an equal volume cold methanol. After centrifugation, the supernatant was concentrated and purified by HPLC using a Alltech semiprep SAX column (10×250 mm) with a linear gradient of 50-175 mM ammonium acetate pH 5.5 over 20 minutes. TDP-4-amino-glucose-containing fractions were pooled and lyophilized, and purity was analyzed by $^{31}P$-NMR.

In Vitro Glycosylation Reactions

Glycosyltransferases GtfE and GtfD were overproduced and purified as previously described, Losey H C, Peczuh M W, Chen Z, Eggert U S, Dong S D, Pelczer I, et al. Tandem action of glycosyltransferases in the maturation of vancomycin and teicoplanin aglycones: novel glycopeptides. Biochemistry 2001;40(15):4745-55; and 9. Solenberg P J, Matsushima P, Stack D R, Wilkie S C, Thompson R C, Baltz R H. Production of hybrid glycopeptide antibiotics in vitro and in *Streptomyces toyocaensis*. Chem Biol 1997;4(3):195-202. Reactions were carried out and analyzed by HPLC as previously described. In brief, synthetic UDP-glucose derivatives were added to a final concentration of 5 mM in a 100 µL reaction, and 50 µL of the $E_p$ reaction mixture to make each TDP-glucose derivative was added to make a final reaction volume of 100 µL. Each 100 µL reaction contained either 1 mM vancomycin aglycone or 0.5 mM teicoplanin aglycone. The final concentration of GtfE and GtfD in each reaction was 5 µM. Reactions with GtfD also contained 2 mM UDP-L-4-epi-vancosamine. 50 µL time points were taken at 0 and 20 h, and quenched with 9 vol methanol. After centrifugation, the supernatants were dried and resuspended in water for HPLC analysis. All glycosylation reactions were monitored by UV (285 nm) using a Vydac C18 small pore column with a linear gradient of 0-20 percent acetonitrile in water with 0.1 percent trifluoracetic acid. The molecular weight of new products was analyzed by Maldi-TOF mass spectrometry using a Perseptive Biosystems Voyager-DE STR mass spectrometer.

In order to determine steady-state kinetic parameters of GtfE, the concentrations of each sugar listed in Table 2 were varied. All reactions were carried out with 1 mM vancomycin aglycone as the acceptor substrate. For UDP- and TDP-glucose, [GtfE] was 50 nM, and the sugar substrates were varied from 0.25 mM-8 mM; for UDP-xylose, [GtfE] was 200 nM and UDP-xylose was varied from 0.5-24 mM; for UDP-6-chloro-glucose, [GtfE] was 5 µM, and the sugar substrates were varied from 1-32 mM; for UDP-2-amino-glucose [GtfE] was 150 nM, and UDP-2-amino-glucose was varied from 0.125-8 mM; for TDP-3-amino-glucose, [GtfE] was 200 nM, and TDP-3-amino-glucose was varied from 0.15-6 mM; for TDP-4-amino-glucose, [GtfE] was 250 nM, and TDP-4-amino-glucose was varied from 0.25-8 mM; and for UDP-6-amino-glucose, [GtfE] was 200 nM, and UDP-6-amino-glucose was varied from 0.25-12 mM. Each experiment was performed in duplicate or triplicate.

Additional Vancomycin Analogs Via Glycorandomization

Figure 14:
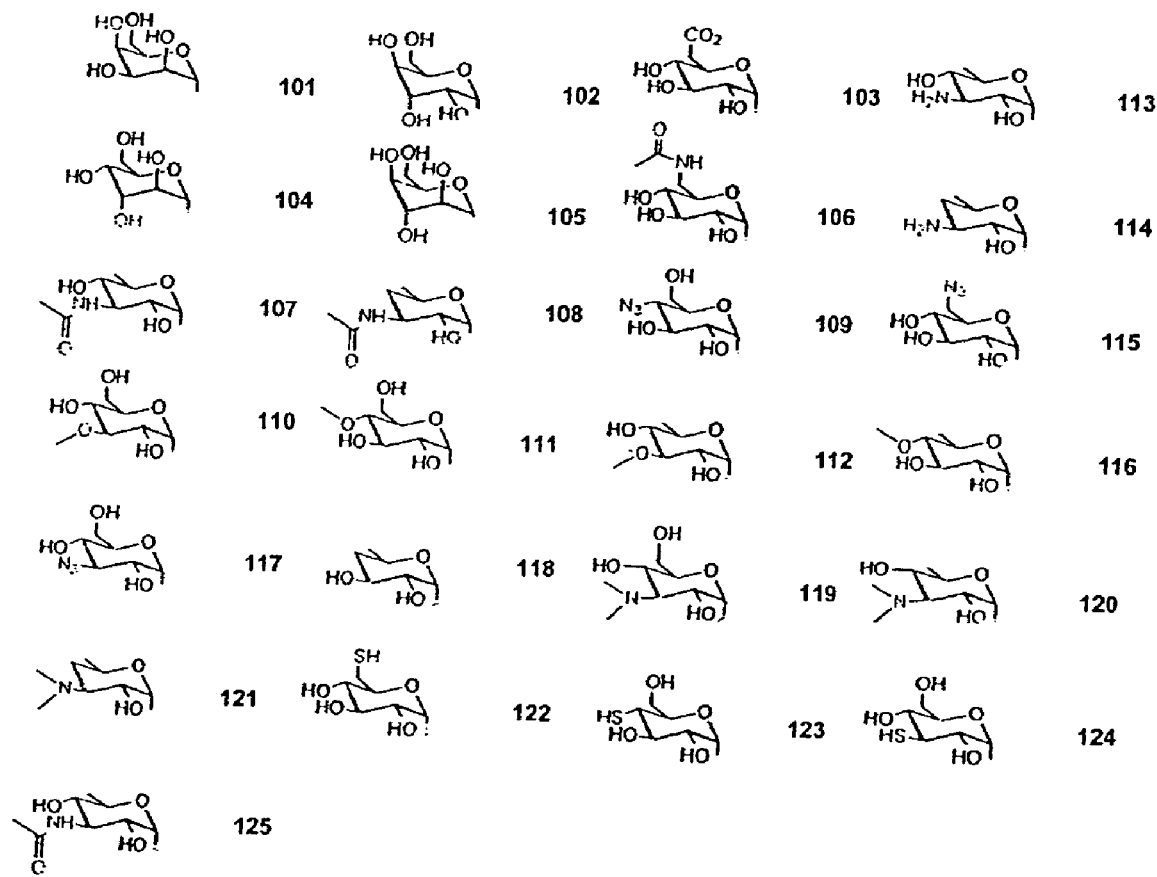
FIG. 14 illustrates annother embodiment of an expanded library of sugars useful in practicing the present invention.
Figure 15:
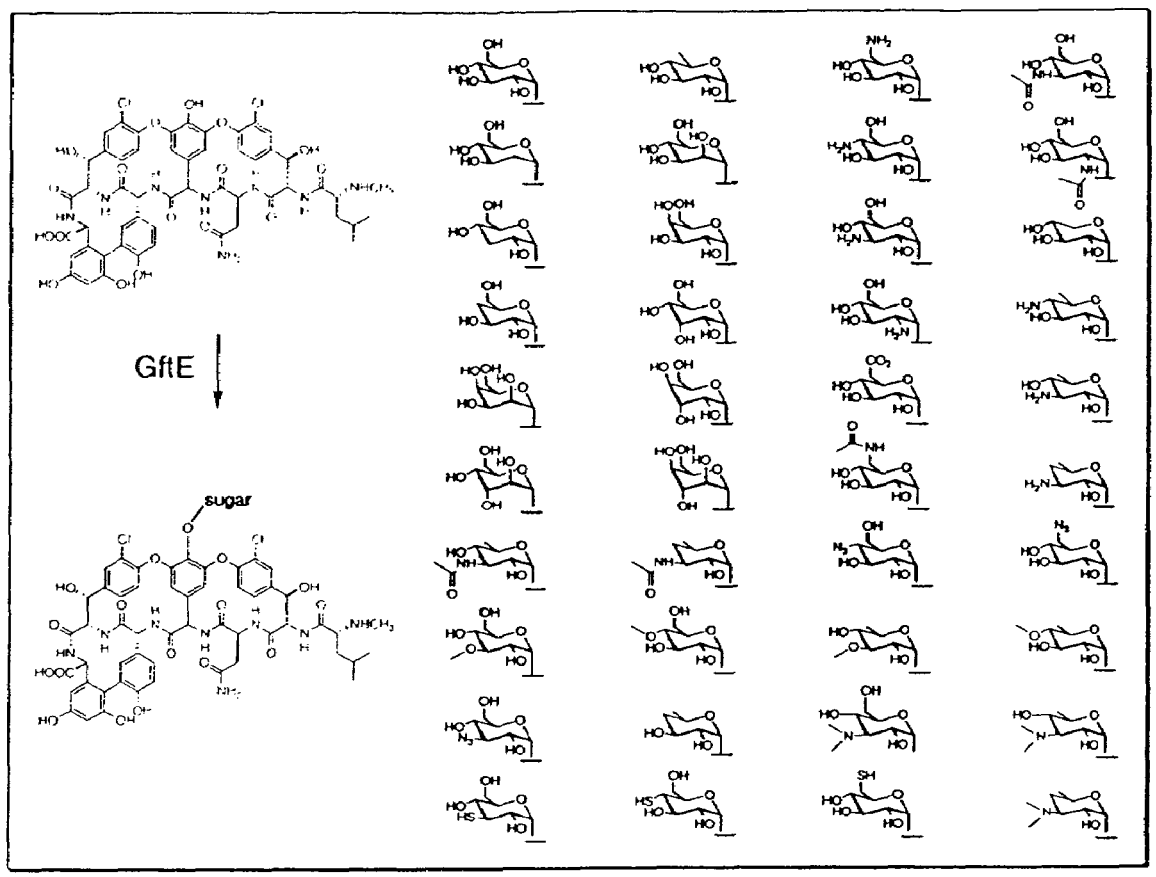
FIG. 15 depicts additional variant vancomycins based upon the expanded library of sugar shown in FIG. 14.

A small library of vancomyin analogs is described above. However, this library size has been significantly increased via the use of our expanded library of nucleotide sugars shown in FIG. 14. The new variants are illustrated in FIG. 15. Furthermore, the fact that monoglycosylated derivatives generated can be accepted by the next transferase in the vancomycin pathway, as noted above, illustrates the significant power of this methodology—namely the potential for exponential library growth.

The experimental procedure for generating the new analogs shown in FIG. 15 follows the GftE experimental method described above. For the expanded library work, the vancomycin aglycon was generated by chemical hydrolysis of commercially available vancomycin via published methodology well known to those in the field. All new products were confirmed by HPLC isolation and HRMS, as described herein or using techniques common to the field.

Synthesis of the sugar phosphates in FIG. 14 was: described below; reported previously in a reference cited herein, or unnecessary due to the availability of the particular sugar phosphate through commercial sources (e.g., Sigma).

Route to Compound 117—2,4, 6Tri-acetyl-3-azido-3-deoxy-α-D-glucopyranosoyl bromide. 1,2,4,6-Tetra-O-acetyl-3-azido-3-deoxy-D-glucopyranoside (430 mg, 1015 mmol) was dissolved in a mixture of 30 mL $CH_2Cl_2$ and 3 mL EtOAc. Titanium tetrabromide (725 mg, 1.97 mmol) was added and the reaction mixture was stirred at room temperature for 3 days. NaOAc (730 mg) was added to quench the reaction, then the suspension was diluted with 150 mL of $CH_2Cl_2$ and extracted with water (30 mL), The organic layer was dried over $Na_2SO_4$, filtered and evaporated, the residue was purified by silica gel chromatography (4:1 hexane-EtOAc), gave the desired product (348 mg, 76.7%). $^1$H NMR ($CDCl_3$): δ 6.62 (d, 1H, $J_{1,2}$=4.0 Hz), 5.05 (t, 1H, J =10.0 Hz, H-4), 4.70 (dd, 1H, J=4.0, 10.0 Hz, H-2), 4.27 (dd, 1H, J=4.4, 12.4 Hz, H-6), 4.20 (m, 1H, H-5), 4.09 (t, J=10.4 Hz, H-3), 4.08 (m, 1H, H-6), 2.18, 2.15, and 2.10 (3 s, 9H, acetate $CH_3$). $^{13}$C NMR ($CDCl_3$): δ 170.44, 169.43, 169.02, 87.02, 72.13, 71.43, 66.86, 61.29, 60.88, 20.59, 20.53.

Route to Compound 117—(3-Methoxy-2-pyridyl) 3-azido-3-deoxy-2,4,6-tri-O-acetyl-β-D-glucopyranoside. A mixture of 2,4,6-Tri-O-acetyl-3-azido-3-deoxy-α-D-glucopyranosyl bromide and silver 3-methoxy-2-pyridoxide in 10 ml anhydrous toluene was refluxed for 1 h. The mixture was filtered over Celite, washed with $CH_2Cl_2$, and concentrated. Purified by flash chromatography on silica gel (hexane-EtOAc 2;1 to 1:1), gave desired product $^1$H NMR ($CDCl_3$): δ 7.05 (dd, J=0.8, 4.4, Hz, 1H), 7.12 (dd, J=1.2, 8 Hz, 1H), 6.95 (dd, J=4.8, 8.0 Hz), 6.20 (d, J=7.6 Hz, 1H), 5.31 (dd, J=8.0, 10.0 Hz, 1H), 5.11 (t, J=10.0 Hz, 1H), 4.23 (dd, J=4.4, 12.4 Hz, 1H), 4.12 (dd, J=3.2, 10.0 Hz, 1H), 3.9 (m, 1H), 3.83 (s, 3H), 3.77 (t, J=10.0 Hz, 1H), 2.09 (s, 3H), 2.06 (s, 3 H), 2.04 (s, 3H); $^{13}$C NMR ($CDCl_3$): δ 170.67, 169.16, 168.97, 151.62, 144.33, 136.66, 119.43, 119.10, 93.68, 73.01, 70.69, 68.17, 64.45, 61.72, 20.65, 20.62, 20.58. MS: cal;cd for $C_{18}H_{22}N_4O_9Na$ 461.1, found m/z 461.0 (M+Na)$^+$.

3-azido-3-deoxy-α-D-glucose-1-phosphate (compound 117). To a mixture of crystalline phosphoric acid (373 mg, 3.8 mmol) and 3-Methoxy-2-pyridyl 3-azido-3-deoxy-β-D-glucopyranoside (170 mg, 0.545 mmol) was added 2 mL od anhydrous DMF. The reaction mixture was stirred at room temperature for three hours, then neutralized with saturated barium hydroxide. The precipitated barium phosphate was emoved by centrifugation and washed with water, the supernatant and washings were combined and concentrated. The residue was dissolved in small amount of water and submitted to an anion exchange column (Dowex 1×8, 1.2×12 cm) eluted with 100 mL water, 100 mL 0.1M $NH_4HCO_3$, 100 mL 0.2 $NH_4HCO_3$, 100 mL 0.3M $NH_4HCO_3$. The product eluted with 0.2 M $NH_4HCO_3$ and these fractions were pooled and co-evaporated with ethanol several times to remove $NH_4HCO_3$. The obtained sugar phosphate ammonium salt was subsequently dissolved in 5 mL of water and applied to an AG-X8 cation-exchange column ($Na^+$ type), eluted with 100 mL water. The product containing fractions were collected and lyophilized to give 85 mg sodium salt, yield 62%. $^1$H NMR ($D_2O$): δ 5.37 (dd, J=3.2, 7.6 Hz, 1H), 3.87 (ddd, J=2.0, 4.8, 9.6 Hz, 1H), 3.78 (dd, J=2.0, 12.0 Hz, 1H), 3.71 (dd, J=10.0 Hz, 1H), 3.68 (dd, J=12.0, 4.8 Hz, 1H) 3.47 (m, 1 H), 3.38 (t, J=10.0 Hz, 1H); $^{13}$C NMR ($D_2O$)): δ 93.39, 72.14, 71.23, 68.71, 66.28, 60.69; $^{31}$P NMR ($D_2O$): δ 3.07. MS: calcd for $C_6H_{11}N_3O_8P^-$ 284.1, found m/z 284.0.

Route to Compound 9—2,3,6-Tri-O-acetyl-4-azido-4-deoxy-α-D-glucopyranosoyl bromide. 1,2,3,6-Tetra-O-acetyl-4-azido-4-deoxy-D-glucopyranoside (1.56 g, 4.18 mmol) was dissolved in a mixture of 60 mL $CH_2Cl_2$ and 6 mL EtOAc. Titanium tetrabromide (2.35 g, 6.4 mmol) was added and the reaction mixture was stirred at room temperature for 3 days. NaOAc (2.35 g) was added to quench the reaction, then the suspension was diluted with 250 mL of $CH_2Cl_2$ and extracted with water (30 mL), The organic layer was dried over $Na_2SO_4$, filtered and evaporated, the residue was purified by silica gel chromatography (4:1 hexane-EtOAc), Recycled 0.42 g start material, gave the desired product (895 mg, 74.5%). $^1$H NMR ($CDCl_3$): δ 6.55 (d, J=4 Hz, 1H, H-1), 5.59 (t, J=10.0 Hz, 1H, H-3), 4.79 (dd, J=4.0, 10.0 Hz, 1H, H-2), 4.40 (dd, J=2.4, 12.8 Hz, 1H, H-6), 4.33 (dd, J=4.0, 12.8 Hz, 1H, H-6), 4.06 (m, 1H, H-5), 3.71 (t, J=10.0 Hz, 1 H, H-4), 2.14 (s, 3H), 2.13 (S, 3H), 2.10 (s, 3H); $^{13}$C NMR ($CDCl_3$): δ 170.55, 170.15, 169.63, 86.63, 72.70, 70.85, 70.77, 62.14, 59.48, 20.96, 20.88; MS: calcd for $C_{12}H_{16}BrN_3O_7Na$ 417.1, found m/z 417.0 (M+Na).

Route to Compound 109—(3-Methoxy-2-pyridyl) 4-azido-4-deoxy-2,3,6-tri-O-acetyl-β-D-glucopyranoside. A mixture of 2,3,6-Tri-O-acetyl-4-azido-4-deoxy-α-D-glucopyranosyl bromide (840 mg, 2.163 mmol) and silver 3-methoxy-2-pyridoxide (830 mg) in 35 ml anhydrous toluene was refluxed for 1 h. The mixture was filtered over Celite, washed with $CH_2Cl_2$, and concentrated. Purified by flash chromatography on silica gel (hexane-EtOAc 2;1 to 1:1), gave desired product 744 mg, yield: 75%. $^1$H NMR ($CDCl_3$): 7.70 (dd, J=1.6, 4.8 Hz, 1H), 7.11 (dd, J=1.6, 8.0 Hz, 1H), 6.95 (dd, J=4.8, 8.0 Hz, 1H), 6.23 (d, J=8.0 Hz, 1H, H-1), 5.31 (m, 2H), 4.39 (dd, J=2.4, 12.4 Hz, 1H, H-6), 4.28 (dd, J=4.0, 12.4 Hz, H-6), 3.83 (s, 3H), 3.77 (m, 1H), 3.70 (m, 1H), 2.13 (s, 3H), 2.08 (s, 3H), 1.98 (s, 3H); $^{13}$C NMR ($CDCl_3$): δ 170.73, 170.18, 169.80, 151.70, 144.25, 137.04, 119.49, 119.33, 93.60, 74.18, 72.69, 71.35, 62.90, 60.13, 56.11, 20.96, 20.92, 20.82. calcd for $C_{18}H_{22}BrN_4O_9Na$ 461.1, found m/z 461.0 (M+Na).

4-azido-4-deoxy-α-D-glucose-1-phosphate (Compound 109). To a mixture of crystalline phosphoric acid (1.12 g, 11.4 mmol) and 3-Methoxy-2-pyridyl 4-azido-4-deoxy-β-D-glucopyranoside (490 mg, 1.57 mmol) was added 3 mL of anhydrous DMF. The reaction mixture was stirred at room temperature for three hours, then neutralized with saturated barium hydroxide. The precipitated barium phosphate was removed by centrifugation and washed with water, the supernatant and washings were combined and concentrated. The residue was dissolved in small amount of water and submitted to an anion exchange column (Dowex 1×8, 1.2×12 cm) eluted with 100 mL water, 100 mL 0.1M $NH_4HCO_3$, 100 mL 0.2 $NH_4HCO_3$, 100 mL 0.3M $NH_4HCO_3$. The product eluted with 0.2 M $NH_4HCO_3$ and these fractions were pooled and co-evaporated with ethanol several times to remove $NH_4HCO_3$. The obtained sugar phosphate ammonium salt was subsequently dissolved in 5 mL of water and applied to an AG-X8 cation-exchange column (Na+ type), eluted with 100 mL water. The product containing fractions were collected and lyophilized to give 268 mg sodium salt, yield 60.3%. $^1$H NMR (CDCl$_3$): Need proton spectrum MS: calcd for C$_6$H$_{11}$N$_3$O$_8$ 284.1, found m/z 284.3 (M+H)$^-$.

Route to Compound 115—2,3,4-Tri-O-acetyl-6-azido-6-deoxy-α-D-glucopyranosoyl bromide. 1,2,3,4-Tetra-O-acetyl-6-azido-6-deoxy-D-glucopyranoside (665 mg, 1.78 mmol) was dissolved in a mixture of 30 mL CH$_2$Cl$_2$ and 3 mL EtOAc. Titanium tetrabromide (981 mg, 62.67 mmol) was added and the reaction mixture was stirred at room temperature for 3 days. NaOAc (980 mg) was added to quench the reaction, then the suspension was diluted with 150 mL of CH$_2$Cl$_2$ and extracted with water (30 mL), The organic layer was dried over Na$_2$SO$_4$, filtered and evaporated, the residue was purified by silica gel chromatography (4:1 hexane-EtOAc), Recycled 247 mg start material, gave the desired product (380 mg, 86%). $^1$H NMR (CDCl$_3$): δ 6.63 (d, J=4.0 Hz, 1H, H-1), 5.55 (t, J=9.6 Hz, 1H, H-3), 5.15 (t, J=9.0, Hz, 1H, H-4), 4.83 (dd, J=4.0, 9.6 Hz, 1H, H-2), 4.27 (m, 1H, H-5), 3.50 (dd, J=2.8, 13.6 Hz, 1H, H-6), 3.37 (dd, J=13.6, 5.2 Hz, 1H, H-6), 2.10 (s, 3H), 2.08 (S, 3H), 2.06 (s, 3H); $^{13}$C NMR (CDCl$_3$): δ169.79, 169.66, 169.36, 86.05, 72.96, 70.48, 69.94, 68.16, 50.17, 20.54, 20.53, 20.49; MS: calcd for C$_{12}$H$_{16}$BrN$_3$O$_7$ Na 417.1, found n/z 417.0 (M+Na).

Route to Compound 115—(3-Methoxy-2-pyridyl) 6-azido-6-deoxy-2,3,4-tri-O-acetyl-β-D-glucopyranoside A mixture of 2,3,4-Tri-O-acetyl-6-azido-6-deoxy-α-D-glucopyranosyl bromide (370 mg, 0.94 mmol) and silver 3-methoxy-2-pyridoxide (400 mg) in 25 ml anhydrous toluene was refluxed for 1 h. The mixture was filtered over Celite, washed with CH$_2$Cl$_2$, and concentrated. Purified by flash chromatography on silica gel (hexane-EtOAc 2;1 to 1:1), gave desired product 338 mg, yield: 82%. $^1$H NMR (CDCl$_3$): 7.73 (dd, J=1.2, 5.2 Hz, 1H), 7.12 (dd, J=1.2, 7.6 Hz, 1H), 6.95 (dd, J=4.8, 8.0 Hz, 1H), 6.27 (d, J=7.6 Hz, 1H, H-1), 5.35 (m, 2H), 5.10 (t, J=9.2 Hz, 1H), 3.93 (m, 1H), 3.40 (dd, J=6.8, 13.6 Hz, 1H, H-6), 3.25 (dd, J=2.8, 13.6 Hz, 1H, H-6), 2.06 (s, 3H), 2.04 (s, 3H), 1.00 (s, 3H); $^{13}$C NMR (CDCl$_3$): δ 170.22, 169.53, 169.27, 151.54, 144.32, 136.97, 119.50, 119.14, 93.49, 73.67, 72.96, 70.82, 69.56, 55.98, 50.90, 20.60; calcd for C$_{18}$H$_{22}$BrN$_4$O$_9$Na 461.1, found m/z 461.0 (M+Na).

6-azido-6-deoxy-α-D-glucose-1-phosphate (Compound 115). To a mixture of crystalline phosphoric acid (0.52 g, 5.3 mmol) and 3-Methoxy-2-pyridyl 6-azido-6-deoxy-β-D-glucopyranoside (134.3 mg, 0.43 mmol) was added 2 mL of anhydrous DMF. The reaction mixture was stirred at room temperature for three hours, then neutralized with saturated barium hydroxide. The precipitated barium phosphate was removed by centrifugation and washed with water, the supernatant and washings were combined and concentrated. The residue was dissolved in small amount of water and submitted to an anion exchange column (Dowex 1×8, 1.2× 12 cm) eluted with 100 mL water, 100 mL 0.1M NH$_4$HCO$_3$, 100 mL 0.2 NH$_4$HCO$_3$, 100 mL 0.3M NH$_4$HCO$_3$. The product eluted with 0.2 M NH$_4$HCO$_3$ and these fractions were pooled and co-evaporated with ethanol several times to remove NH$_4$HCO$_3$. The obtained sugar phosphate ammonium salt was subsequently dissolved in 5 mL of water and applied to an AG-X8 cation-exchange column (Na+ type), eluted with 100 mL water. The product containing fractions were collected and lyophilized to give 48 mg sodium salt, yield 60.3%. $^1$H NMR (D$_2$O): 5.42 (dd, J=3.6, 7.6 Hz, 1H, H-1), 3.97 (m, 1H), 3.73 (t, J=7.2 Hz, 1H), 3.64 (dd, J=2.8, 13.6 Hz, 1H), 3.58 (dd, J=4.0, 13.6 Hz, 1H), 3.48 (ddd, J=2.0, 3.6, 9.6 Hz, 1H), 3.44 (t, J =9.6 Hz, 1H); $^{13}$C NMR (CDCl$_3$): δ 94.22, 73.07, 72.20, 70.94, 70.38, 51.06; 31 P NMR (D2O): δ 2.33; MS: calcd for C$_6$H$_{11}$N$_3$O$_8$ 284.1, found m/z 284.2 (M+H)$^-$.

Routes to Compound 110-112, 116—1,2,4,6-tetra-O-benzoyl-3-methoxy-D-glucopyranoside. 2.6 g (13.4 mmol) of 3-methoxy-D-glucopyranoside was dissolved in 50 ml anhydrous pyridine, 9.33 ml of benzoyl chloride was added through a syringe within 20 min, the reaction mixture was stirred overnight at room temperature. The solvent was removed by concentration under reduced pressure, the residue was patitioned between 300 mL EtOAc and 100 mL water, the organic layer was washed with water, brine, dried over Na2SO4, and concentrated, purified by silica gel chromatography (hexane:EtOAc 2:1), get 7.95 g product.

Routes to Compound 110-112, 116—Ethyl 2,4,6-tri-O-benzoyl-3-methoxy-1-thio-β-D-glucopyranoside. A mixture of 4.14 g of 1,2,4,6-tetra-O-benzoyl-3-methoxy-D-glucopyranoside (6.78 mmol), 2.2 mL of (ethylthio)trimethylsilane (13.5 mmol) and 6.5 g (20.0 mmol) zinc iodide in 100 ml anhydrous dichloromethane was refluxed for 1 hr under argon atmosphere. The reaction was then cooled and diluted with 200 ml CH2Cl2, washed with water, saturated NaHCO3 solution, water, brine, the organic layer was dried over NaSO4, concentrated and purified by chromatography (Hexane:EtOAc 8:1), afforded pure product 2.89 g, yield 77%. $^1$H NMR (CDCl$_3$): 8.11-8.00 (m, 6H), 7.60-7.36 (m, 9H), 5.50 (t, J=7.2 Hz, 1H), 5.40 (t, J=7.2 Hz, 1H), 4.75 (d, J=10.0 Hz, 1H), 4.61 (dd, J=3.2, 12.0 Hz, 1H), 1.45 (dd, J=6.0, 12.0 Hz, 1H), 4.08 (m, 1H), 3.91 (t, J=9.2 Hz, 1H), 3.47 (s, 3H), 2.70 (m, 2H), 1.25 (t, J=7.6 Hz, 3H); $^3$C NMR (CDCl$_3$): δ 166.04 165.00, 164.95, 133.37, 133.22, 132.96, 130.00, 83.75, 83.18, 76.08, 71.76, 70.67, 63.47, 60.02, 24.16, 14.81. MS: calcd for C$_{30}$H$_{30}$NaO$_8$S 573.1, found m/z 573.1.

Routes to Compound 110-112, 116—Ethyl 2,4,6-tri-O-benzyl-3-methoxy-1-thio-β-D-glucopyranoside. $^1$H NMR (CDCl$_3$): δ 7.48-7.30 (m, 15H), 4.99 (d, J=10.8 Hz, 1H), 4.91 (d, J=10.8 Hz, 1H), 4.83 (d, J=10.8 Hz, 1H), 4.65 (d, J=12.0 Hz, 2H), 4.52 (d, J=9.6 Hz, 1H), 3.82 (dd, J=2.0, 10.8 Hz, 1H), 3.76 (s, 3H), 3.75 (dd, J=4.8, 10.8 Hz, 1H), 3.60 (t, J=9.6 Hz, 1H), 3.52 (ddd, J=2.0, 4.8, 9.6 Hz, 1H), 3.46 (m, 2H), 2.86 9 m, 2H), 1.41 (t, J=7.2 Hz, 3H); $^{13}$C NMR (CDCl$_3$): δ 138.05, 138.00, 137.92, 128.20, 128.15, 127.86, 127.64, 127.60. 127.55, 127.39, 88.47, 84.76, 81.55, 78.79, 77.72, 75.22, 74.71, 73.21, 68.92, 61.11, 24.79, 15.03.

Routes to Compound 110-112, 116—Dibenzyl-(2,4,6-tri-Obenzyl-3-methoxy-α-D-glucopyranosyl) phosphate. Use general procedure for the phosphorylation (via ethyl 1-thio-β-D-hexopyranoside. 600 mg Ethyl 2,4,6-tri-O-benzyl-3-methoxy-1-thio-β-D-glucopyranoside (1.18 mmol) gave 820 mg product, yield 95.9%. $^1$H NMR (CDCl$_3$): δ7.47-7.25 (m, 25H), 6.01 (dd, J=3.2, 6.8 Hz, 1H), 5.10 (m, 4H), 4.88 (d, J=10.4 Hz, 1H), 4.83 (d, J=11.6 Hz, 1H), 4.74 (d, J=11.6 Hz, 1H), 4.61 (d, J=12.4 Hz, 1 H), 4.56 ((d, J=10.8 Hz, 1H), 4.48 (d, J=12.4 Hz, 1H), 3.95 (m, 1H), 3.73-3.64 (m, 7H), 3.62 (m, 1H), 3.53 (dd, J=1.6, 10.8 Hz, 1H); $^{13}$C NMR (CDCl$_3$): δ 138.06, 137.65, 137.62, 135.72, 135.65, 128.32, 128.26, 128.25, 128.23, 128.18, 128.14, 127.81,. 127.77, 127.73, 127.66, 127.59, 127.53, 65.57, 83.04, 78.90, 74.84, 73.29, 72.80, 72.20, 69.12, 69.07, 68.93, 67.72, 61.09; $^{31}$P NMR (CDCl$_3$): δ −1.05. MS calcd for C$_{42}$H$_{45}$O$_9$PNa 747.3, found m/z 747.2.

Disodium 4-methoxy-α-D-glucopyranosyl phosphate—Compound 110. Use general procedure for the final deprotection and conversion to the sodium salt. 778 mg Dibenzyl- (2,4,6-tri-Obenzyl-3-methoxy-α-D-glucopyranosyl) phosphate (1.07 mmol) gave 200 mg product, Yield 68%. $^1$H NMR (D$_2$O): δ 5.32 (dd, J=2.8, 7.6 Hz, 1H), 3.81 (m, 1H), 3.74 (dd, J=2.0, 12.4 Hz, 1H), 3.63 (dd, J=5.2, 12.4 Hz, 1H), 3.51 (s, 3H), 3.47 (m, 2H) 3.37 (m, 1H); $^{13}$C NMR (D$_2$O): δ 94.06, 82.98, 72.30, 71.67, 69.20, 60.72, 60.03; $^{31}$P NMR (D$_2$O): δ 2.81; MS calcd for C$_7$H$_{14}$O$_9$P 273.0, found m/z 273.1. Compounds 11, 12 and 16 generated via similar strategies from appropriate starting materials.

Route to Compound 114—Methyl-2-O-benzoyl-4,6-dideoxy-α-D-ribo-hexopyranoside. A mixture of 4.5 g (16.9 mmol) of Methyl 2-O-benzoyl-4,6-dideoxy-α-D-erythro-hexopyranoside (see Stephen Hanessian and Rene Roy Can J. Chem. 63, 163 (1985)), PCC (14.6 g, 67.7 mmol) and NaOAc (2.77 g, 33.8 mmol) in 200 ml of dichloromethane was stirred at room temperature overnight, then ether was added to the dark suspension, the salts were filtered, and the filtrate and washins were evaporated, the residue was sried under vacuo for 2 hrs. Then the crude product was dissolved in 100 mL methanol, sodium borohydride (768 mg, 20 mmol) was added, the solution was stirred for 20 mins. Excess hydride was destroyed by addition of acetic acid to pH 6, the solution was evaporated to dryness, and the residue was partioned between EtOAc (300 mL) and 50 mL water, the organic layer was separated and washed with water, brine, dried over Na2SO4, the filtrate was evaporated to dryness. Purification by silica gel chromatography (hexane-EtOAc 6:1) gave 3.89 g pure product, yield: 87.1%. $^1$H NMR (CDCl$_3$): δ 8.11 (m, 2H), 7.59 (m, 1H), 7.45 (m, 2H), 5.05 (t, J=3.2 Hz, 1 H), 5.00 (m, 1H), 4.25 (m, 2H), 3.74 (dd, J=0.8, 8.8 Hz, 1H), 3.47 (s, 3H), 2.01 *m, 1H), 1.72 (m, 1H), 1.27 (d, J=6.4 Hz, 3H); MS: calcd for C14H18NaO5 289.1, found m/z 289.1 (M+Na).

Route to Compound 114—Methyl 3-azido-2-O-benzoyl-3,4,6-trideoxy-α-D-glucopyranoside. To a solution of Methyl-2-O-benzoyl-4,6-dideoxy-α-D-ribohexopyranoside (3.89 g, 14.6 mmol) and pyridine 4.74 mL (58.6 mmol) in 100 mL of dichloromethane at −10° C. was slowly added triflic anhydride (3.2 mL, 19.0 mmol). Stirring was continued for for 1 hr at −10° C. and then 2 hrs at room temperature. The mixture was diluted with EtOAc (300 mL), the solution was washed with 5% HCl, saturated NaHCO$_3$ and brine, dried over Na$_2$SO$_4$, and concentrated to give the crude triflate, the crude triflate was dissolved in 30 mL anhydrous DMF, sodium azide (1.3 g, 50 mmol) was added, and stirring was continued for overnight. The mixture was diluted with EtOAc (250 mL) and was washed with water (3×30 mL), and brine (30 mL), dried over Na2SO4, and concentrated. Purification by flash chromatography (silica gel, Hexane:EtOAc 10:1), gave 3.6 g product, yield 84.7%. $^1$H NMR (CDCl$_3$): δ 8.11 (m, 2H), 7.59 (m, 1H), 7.46 (m, 2H), 5.03 (d, j=3.2 Hz, 1H), 4.90 (dd, J=3.6, 10.8 Hz, 1H), 4.13 (m, 1H), 4.00 (m, 1H), 2.07 (ddd, J=2.4, 4.8, 13.2 Hz, 1H), 1.48 (m, 1H), 1.24 (d, J=6.4 Hz, 3H); $^{13}$C NMR (CDCl$_3$): δ 165.81, 133.27, 130.03, 129.86, 128.36, 97.03, 74.46, 63.11, 56.76, 55.08, 38.11, 20.53; MS calcd for C$_{14}$H$_{17}$N$_3$O$_4$ 314.1, found m/z 314.1.

Route to Compound 114—1,2-di-O-benzoyl-3azido-3,4,6-trideoxy-α-D-glucose. To a solution of methyl 3-azido-2-O-benzoyl-3,4,6-trideoxy-α-D-glucopyranoside (3.6 g, 12.37 mmol) in 50 mL methanol, 1 mL 30% MeONa was added, the mixture was stirred overnight at room temperature, it was then neutralized with DOWEX 50WX8-100 ion-exchange resin, the filtrate was concentrated and dissolved in 27 mL 2N H$_2$SO$_4$, the mixture was stirred for 6 hrs at 120° C., Barium carbonate was added until pH reach 7, the precipitate barium sulfate was removed by filtration, the filtrate was concentrated and purified by silica gel chromatography (CHCl$_3$:MeOH 10:1), gave 1.14 g product, yield 53%. This compound was then benzoylated with benzoyl chloride/pyridine condition, gave 1,2-di-O-benzoyl-3azido-3,4,6-tiideoxy-α-D-glucose 2.12 g.

Route to Compound 114—Ethyl 3-azide-2-O-benzoyl-3-deoxy-1-thio-3,4,6-trideoxy-β-D-glucopyranoside. A mixture of 2.12 g 1,2-di-O-benzoyl-3azido-3,4,6-tiideoxy-α-D-glucose (5.56 mmol), 1.8 mL of (ethylthio)trimethylsilane (11.1 mmol) and 2.32 g (16.7 mmol) zinc iodide in 100 ml anhydrous dichloromethane was refluxed for 1 hr under argon atmosphere. The reaction was then cooled and diluted with 200 ml CH$_2$Cl$_2$, washed with water, saturated NaHCO$_3$ solution, water, brine, the organic layer was dried over NaSO$_4$, concentrated and purified by chromatography (Hexane:EtOAc 10:1), afforded pure product 1.51 g, yield 84%. $^1$H NMR (CDCl$_3$): δ 8.15 (m, 2H), 7.62 (m, 1H), 7.47 (m, 2H), 5.10 (t, J=9.2 Hz, 1H), 4.53 (d, J=9.6 Hz, 1H), 3.73 (m, 2H), 2.72 (m, 2H), 2.14 (ddd, J=2.0, 4.8, 13.2 Hz, 1H), 1.60 (m, 1H), 1.33 (d, J=6.0 Hz, 3H), 1.23 (t, J=7.2 Hz, 3H); $^{13}$C NMR (CDCl$_3$): 165.42, 133.74, 133.26, 130.16129.86, 128.45, 138.39, 83.49, 72.71, 72.31, 61.65, 37.90, 23.74, 20.98, 14.71.

Route to Compound 114—Ethyl 3-azide-2-O-benzyl-3-deoxy-1-thio-3,4,6-trideoxy-α-D-glucopyranoside. $^1$H NMR (CDCl$_3$): δ 7.46 (m, 2H), 7.30 (m, 3H), 4.92 (d, J=10.0 Hz, 1H), 4.74 (d, J=10.0 Hz, 1H), 4.41 (d, J=9.6 Hz, 1H), 3.55 (m, 2H), 3.20 (t, J=9.6 Hz, 1H), 2.75 (m, 2H), 1.96 (dd, J=8.8, Hz 13.2 Hz, 1H), 1.41 (m, 1H), 1.31 (t, J=7.6 Hz, 3H), 1.25 (d, J=6.0 Hz, 3H); $^{13}$C NMR (CDCl$_3$): 137.43, 128.60, 128.32, 127.93, 85.04, 80.98, 75.22, 72.16, 63.50, 38.21, 24.87, 20.92, 14.96; MS: calcd for C$_{15}$H$_{21}$NaN$_3$O$_2$S 330.1, found 330.1 (M+Na).

Route to Compound 114—Dibenzyl-(3-azide-2-O-benzyl-3,4,6-trideoxy-α-D-glucopyranosyl) phosphate. Use general procedure for the phosphorylation (via ethyl 1-thio-β-D-hexopyranoside) Ethyl 3-azide-2-O-benzyl-3-deoxy-1-thio-3,4,6-trideoxy-β-D-glucopyranoside (350 mg, 1.14 mmol) gave 378 mg desired product, yield 63.4%. $^1$H NMR (CDCl$_3$): δ 7.40-7.23 (m, 15H), 5.93 (dd, J=3.2, 6.8 Hz, 1H), 5.07 (d, J=8.0 Hz, 1H), 5.06 (d, J=8.0 Hz, 1H), 5.02 (m, 2H), 4.76 (d, J=11.2 Hz, 1H), 4.65 (d, J=11.2 Hz, 1H), 4.00 (m, 1H), 3.77 (m, 1H), 3.40 (dt, J=10.0, 3.2 Hz, 1H), 1.91 (ddd, J=2.4 4.8, 13.2 Hz, 1H), 1.31 (m, 1H), 1.09 (d, J=6.4 Hz, 3H); $^{31}$P NMR (CDCl$_3$): δ −0.91; $^{13}$C NMR (CDCl$_3$): δ 137.01, 135.83, 135.76, 135.68, 128.47, 128.42, 128.40, 128.37, 128.33, 128.17, 128.05, 127.96, 127.77, 127.63, 95.34, 78.63, 72.35, 69.28, 69.23, 69.08, 69.03, 65.65, 57.32, 37.61, 20.47.

Disodium 3-amino-3,4,6-trideoxy-α-D-glucopyranosyl phosphate—Compound 114. Use general procedure for the final deprotection and conversion to the sodium salt. Dibenzyl-(3-azide-2-O-benzyl-3,4,6-trideoxy-α-D-glucopyrano-syl) phosphate 378 mg (0.72 mmol) gave 93 mg product, Yield 57%. $^1$H NMR (D$_2$O): δ 5.33 (dd, J=3.2, 7.2 Hz, 1H), 4.14 (m, 1H), 3.53 (m, 2H), 2.04 (ddd, J=2.4, 4.0, 12.8 Hz, 1H), 1.40 (m, 1H), 1.08 (d, J=6.4 Hz, 3H); $^{13}$C NMR (D$_2$O): δ 93.36, 70.27, 64.63, 49.13, 35.72, 19.81; $^{31}$P NMR (D2O): δ 2.91; MS calcd for C$_6$H$_{13}$NO$_6$P 226.1, found m/z 226.1.

Route to Compound 108—Ethyl 3-acetamino-2-O-benzyl-3-deoxy-1-thio-3,4,6-trideoxy-β-D-glucopyranoside. Ethyl 3-azide-2-O-benzyl-3-deoxy-1-thio-3,4,6-trideoxy-β-D-glucopyranoside was reduced by SnCl2/PhSH/Et3N (See J. Org. Chem 1996, 61, 6153) and acetylated (Ac2O/Py) (see Angew Chem paper). 290 mg (0.94 mmol) gave 280 mg pure product, yield 91%. $^1$H NMR (CDCl$_3$): δ 7.37 (m, 5H), 5.11 (d, J=6.0 Hz, 1H), 4.85 (d, J=12.0 Hz, 1H), 4.59 (d, J=12.0 Hz, 1H), 4.51 (d, J=9.2 Hz, 1H), 3.95 (m, 1H), 3.60 (m, 1H), 2.13 (ddd, J=2.0, 4.8, 13.2 Hz, 1H), 1.74 (s, 3H), 1.34 (t, J=7.6 Hz, 3H), 1.24 (m, 1H), 1.20 (d, J=6.4 Hz, 3H); $^{13}$C NMR (CDCl$_3$): 169.72, 137.95, 128.80, 128.60, 128.11, 85.61, 78.88, 73.85, 72.58, 51.64, 39.31, 25.07, 23.34, 20.86, 14.95; MS: calcd for $C_{17}H_{25}NaNO_3S$ 346.1, found 346.2 (M+Na).

Route to Compound 108—Dibenzyl-(3-aetamino-2-O-benzyl-3,4,6-trideoxy-α-D-glucopyranosyl) phosphate. Use general procedure for the phosphorylation (via ethyl 1-thio-β-D-hexopyranoside) Ethyl 3-aaetamino-2-O-benzyl-3-deoxy-1-thio-3,4,6-trideoxy-β-D-glucopyranoside (260 mg, 0.80 mmol) gave 323 mg desired product, yield 75%. $^1$H NMR (CDCl$_3$): δ 7.22 (m, 15H), 6.06 (d, J=7.2 Hz, –NHAc), 5.90 (dd, J=3.2, 6.4 Hz, 1H), 4.84 (m, 4H), 4.62 (d, J=11.6 Hz, 1H), 4.35 (d, J=12.0 Hz, 1H), 4.20 (m, 1H), 3.94 (1H), 3.35 (dt, J=2.8, 10.4 Hz, 1H), 2.01 (dt, J-2.0, 11.2 Hz, 1H), 1.17 (m, 1H), 0.95 (d, J=6.0 Hz, 3H); $^{31}$P NMR (CDCl$_3$): δ −1.47; $^{13}$C NMR (CDCl$_3$): δ 175.54, 137.92, 136.00, 135.96, 135.93, 135.89, 128.76, 128.73, 128.68, 128.64, 128.58, 128.34, 128.19, 128.17, 128.11, 127.74, 95.98, 77.24, 72.08, 69.70, 69.65, 69.34, 39.28, 66.52, 46.50, 38.89, 23.58, 20.75; MS calcd for $C_{29}H_{34}NaNO_7P$ 562.2, found m/z 562.2.

Disodium 3-aetamino-3,4,6-trideoxy-α-D-glucopyranosyl phosphate—Compound 108. Use general procedure for the final deprotection and conversion to the sodium salt. Dibenzyl-(3-acetamino-2-O-benzyl-3,4,6-trideoxy-α-D-glucopyranosyl) phosphate 323 mg (0.60 mmol) gave 89 mg product, Yield 56%. $^1$H NMR (D$_2$O): δ 5.41 (dd, J=3.2, 6.8 Hz, 1H), 4.20 (m,1H), 4.09 (dt, J=4.4, 11.2 Hz, 1H), 3.47 (m,1H), 1.95 (s, 3H), 1.90 (m, 1H), 1.30 (m,1H), 1.11 (d, J=6.0 Hz, 3H); $^{13}$C NMR (D$_2$O): δ 174.22, 94.34, 71.27, 65.53, 47.43, 37.96, 22.24, 19.88

Route to Compound 118—Ethyl 2,3-di-O-benzyl-4,6-dideoxy-1-thio-β-D-glucopyranoside. $^1$H NMR (D$_2$O): δ 7.41-7.22 (m, 2H), 4.88 (d, J=10.0 Hz, 1H), 4.80 (d, J=10.0 Hz, 1H), 4.68 (m, 1H), 4.40 (d, J=9.6 Hz, 1H), 3.61 (m, 1H), 3.50 (m, 1H), 3.31 (t, J=9.6 Hz, 1H), 2.73 9 m, 2H), 2.08 (ddd, J=2.0, 4.2, 13.2 Hz, 1H), 1.46 (m, 1H) 1.30 (t, J=6.4 Hz, 3H), 1.25 (d, J=6.0 Hz, 3 H); $^{13}$C NMR (D$_2$O): 138.80, 138.64, 128.62, 128.57, 128.54, 127.92, 127.88, 127.84, 85.04, 82.11, 80.53, 75.77, 72.19, 72.13, 38.98, 24.95, 21.46, 15.29.

Disodium 4,6-dideoxy-α-D-glucopyranosyl phosphate—Compound 118. Use general procedure for the final deprotection and conversion to the sodium salt. Dibenzyl-(2,3-di-O-benzyl-4,6-trideoxy-α-D-glucopyranosyl) phosphate 267 mg (0.45 mmol) gave 80 mg product, Yield 56%. $^1$H NMR (D$_2$O): δ 5.40 (dd, J=3.2, 6.8 Hz, 1H), 4.20 (m, 1H), 3.92 (m,1H), 3.36 (ddd, J=2.0, 3.6, 9.6 Hz, 1H), 2.02 (m,1H), 1.31 (m 1H), 1.15 (d, J=6.4 Hz, 3H); $^{13}$C NMR (D$_2$O): δ 94.71, 73.86, 67.45, 65.52, 40.05, 20.03; $^{31}$PNMR (D$_2$O): δ 2.18 MS calcd for $C_6H_{12}O_7P^-$ 227.0, found m/z 227.1.

Route to Compounds 113, 119, 120, 121 and 125—(see J. Am. Chem. Soc 1988, 110, 4696-4705) Methyl 2-O-Benzoyl (R)-4,6-O-benzylidine-α-D-glucopyranoside. Methyl (R)-4,6-O-benzylidine-α-D-glucopyranoside (23.4 g 82.9 mmol) and 35 ml triethyamine were dissolved in 200 ml anhydrous dichloromethane, to this solution (cooled with ice bath), 19.2 ml of Benzoyl Chloride was added dropwise through a dropping funnel (within 40 min), then the reaction mixture was allowed to warm to r. t and stirred overnight. It was then diluted with 300 ml dichloromethane, washed with saturated sodium bicarbonate solution, water, brine, dried over Na2SO4, concentrated and purified by silica gel chromatography (hexane:EtOAc 5:1), gave 24.77 g product, yield: 77%. $^1$H NMR (CDCl$_3$): δ 8.11 (d, J=7.2 Hz, 2H), 7.76-7.36 (m, 8H), 5.56 (s, 1H) 5.08 (d, J=3.7 Hz, 1), 5.05 (dd, J=3.8, 9.4 Hz, 1H), 4.36 (t, J-9.4 Hz, 1H), 4.33 (m, 1 H), 3.92 (m, 1H), 3.79 (t, J=10.2 Hz, 1 h), 3.61 (t, J=9.4 Hz, 1H), 3.39 (s, 3H), 2.97 (Br, 1H, —OH); $^{13}$C NMR (CDCl$_3$): δ 166.15, 136.92, 133.28, 129.87, 129.38, 129.21, 128.34, 128.26, 126.26, 101.91, 97.63, 81.32, 73.97, 68.78, 68.66, 61.94, 55.39; MS: calcd for $C_{21}H_{22}O_7Na$ 409.1, found: 409.0 (M+Na).

Route to Compounds 113, 119, 120, 121 and 125—Methyl 2-O-Benzoyl (R)-4,6-O-benzylidine-α-D-allopyranoside. A mixture of Methyl 2-O-Benzoyl (R)-4,6-O-benzylidine-α-D-glucopyranoside 10.47 g (27.1 mmol) of, PCC (13.4 g, 37.6 mmol) and 3A molecular sieves (24.3 g) in 150 ml of dichloromethane was stirred at room temperature overnight, the mixture was diluted with CH$_2$Cl$_2$ and loaded into a Florisil column. Elution with a 1:1 mixture of CH$_2$Cl$_2$ EtOAc gave the crude ketone product, the residue was dried under vacuo for 2 hrs. Then the crude product was dissolved in a mixed solvent of 150 mL THF and 30 mL methanol, this solution was cooled to −15° C., sodium borohydride (1.03 g, 27.2 mmol) was added, the solution was stirred for 10 mins. The reaction mixture was poured into a saturated NH$_4$Cl-ice mixture and diluted with EtOAc (500 mL), the organic layer was separated washed with water (50 mL), brine (30 mL), dried over Na$_2$SO$_4$, and concentrated. Purification by silica gel chromatography (hexane-EtOAc 3:1) gave 8.95 g pure product, yield: 85%. $^1$H NMR (CDCl$_3$): δ 8.14 (m, 2H), 7.60-7.34 (m, 8H), 5.67 (s, 1H), 5.08 (t, J=3.6 Hz, 1H), 5.03 (d, J=3.6 Hz, 1H), 4.49 (br, 1H), 4.41 (dd, J=5.1, 10.2 Hz, 1H), 4.25 (dt, J=5.1, 10.0 Hz, 1H), 3.82 (t, J=10.3 Hz, 1H), 3.64 (dd, J=2.4, 9.7 Hz, 1H), 3.47 (s, 3H); $^{13}$CNMR (CDCl$_3$): δ 170.91, 136.93, 133.34, 129.84, 129.77, 129.10, 128.92, 128.49, 128.28, 128.05, 126.13, 101.70, 98.48, 78.35, 69.59, 68.85, 67.96, 57.72, 55.93; MS: calcd for $C_{21}H_{22}O_7Na$ 409.1, found: 409.0 (M+Na).

Route to Compounds 113, 119, 120, 121 and 125—Methyl 2-O-benzoyl-(R)-4,6-O-benzylidine-3-O-(tert-Butyldimethylsilyl)-α-D-allopyranoside. To a solution of Methyl 2-O-Benzoyl (R)-4,6-O-benzylidine-α-D-allopyranoside (8.85 g, 23.2 mmol) and 2,6-lutidine (4.1 mL, 35.2 mmol) in dichloromethane at 0° C. was slowly added t-BuMe$_2$SiOtf (6.4 mL, 27.8 mmol). The solution was allowed to reach room temperature and stirred for 2 hr. The reaction mixture was diluted with 350 mL EtOAc and washed sequentially with water, 5% HCl, saturated NaHCO$_3$ solution and brine, dried over Na$_2$SO$_4$, concentrated and purified by silica gel chromatography (hexanes:EtOAc 5:1), gave 102 g product, yield 88%. $^1$H NMR (CDCl$_3$): δ 8.13 (m,2H), 7.59 (m, 1H), 7.49 (m, 4H), 7.38 (m, 3H), 5.58 (s, 1H), 5.05 (dd, J=2.9, 4.1 Hz, 1H), 4.89 (d, J=4.1 Hz, 1H), 4.54 (t, J=2.2 Hz, 1H), 4.38 (m, 2H), 3.76 (m, 1H), 3.65 (dd, J=2.3, 9.1 Hz, 1H), 3.43 (s, 3H), 0.92 (s, 9H), −0.04 (s, 3H), −0.075 (s, 3); $^{13}$CNMR (CDCl$_3$): δ 165.96, 137.39, 133.22, 129.95, 129.68, 128.89, 128.28, 128.00, 126.37, 101.95, 98.25, 78.84, 70.97, 69.27, 68.08, 57.59, 55.83, 25.90, 25.59, 18.18; MS: calcd for $C_{27}H_{36}O_7SiNa$ 523.2, found: 523.2 (M+Na).

Route to Compounds 113, 119, 120, 121 and 125—Methyl 2-O-benzoyl-3-O-(tert-Butyldimethylsilyl)-6-iodine-6-deoxy)-α-D-allopyranoside. 10.2 g of ethyl 2-O-benzoyl-(R)-4,6-O-benzylidine-3-O-(tert-Butyldimethylsilyl)-α-D-allopyranoside was dissolve in 100 mL EtOAc, to this solution, 0.5 g Pd(OH)$_2$ was added, this solution was stirred overnight under hydrogen atmosphere, the catalyst was removed by filtration, filtrate and washings were combined and concentrated. This compound was used for the iodination without further purification. A mixture of hydrogenation product, Ph$_3$P (16 g, 61.1 mmol), I$_2$ (10.34 g, 40.8 mmol), and imidazole (4.16 g, 61.2 mmol) in 100 mL anhydrous benzene was stirred for 4 hrs at 55° C., it was then diluted with EtOAc (500 mL)<washed with 10% Na$_2$S$_2$O$_3$ solution (2×40 mL), water (50 mL), brine (50 mL), dried and concentrated, purified by flash chromatography (hexane: EtOAc 8:1-6:1), obtained 7.85 g product, yield 74% for two steps. $^1$H NMR (CDCl$_3$): δ 8.14 (d, J=7.3 Hz, 2H), 7.60 (t, J=7.7 Hz, 1H), 7.47 (t, J=7.6 hz, 2H), 5.04 (m, 1H), 4.85 (d, J =4.1 Hz, 1H), 4.38 (t, J=2.9 Hz 1H), 3.72 (dt, J=2.4, 9.6 Hz, 1H), 3.66 (dd, J=2.4, 10.6 Hz, 1 H), 3.48 (s, 3H), 3.37 (dd, J=7.6, 106 Hz, 1H) 0.94 (s, 9H), 0.03 (s, 3H0, 0.00 (s, 3H); $^{13}$CNMR (CDCl$_3$): δ 165.98, 133.39, 129.97, 129.55, 128.38, 97.67, 71.17, 71.00, 70.06, 67.45, 55.89, 25.62, 18.26, 7.69, −4.59, −4.83; MS: calcd for C$_{20}$H$_{31}$O$_6$SiNaI 545.1, found: 545.1 (M+Na).

Route to Compounds 113, 119, 120, 121 and 125— Methyl 2-O-benzoyl-3-O-(tert-Butyldimethylsilyl)-6-deoxy-α-D-allopyranoside. A mixture of Methyl 2-O-benzoyl-3-O-(tert-Butyldimethylsilyl)-6-iodine-6-deoxy)-α-D-allopyranoside (6.38 g, 12.7 mmol) and AIBN (80 mg) and Bu$_3$SnH 6.6 mL, 24.5 mmol) in 80 mL anhydrous toluene was refluxed for 2 hrs under argon atmosphere, it was then cooled and concentrated, purified by flash chromatography (hexane:EtOAc 8:1), gave 4.68 g product, yield 97%. $^1$H NMR (CDCl$_3$): δ 8.12 (m, 2H), 7.60 (dt, J=2.2, 5.8 Hz, 1H), 7.48 (m, 2H), 5.04 9 dd, J=3.1, 4.0 Hz, 1H), 4.96 9d, J=3.6 Hz, 1H), 4.36 (t, J=2.9 hz, 1H), 3.94 (m, 1H), 3.40 (s, 3H), 3.34 9 m, 1H), 2.04 (d, J=11.2 Hz, 1H), 1.63 (m, 1H), 1.34 (m, 2H), 0.94 (s, 9H), 0.04 (s, 3H), 0.00 (s, 3H); $^{13}$CNMR (CDCl$_3$): δ 165.99, 133.26, 129.94, 129.90, 128.28, 97.33, 72.51, 71.26, 70.12, 63.77, 55.64, 25.67, 25.58, 18.21, 17.97, 17.50, 16.30, 13.51; MS: calcd for C$_{20}$H$_{32}$O$_6$SiNa 419.2, found: m/z 419.1 (M+Na).

Route to Compounds 113, 119, 120, 121 and 125— Methyl 2,4-di-O-benzoyl-3-O-(tert-Butyldimethylsilyl)-6-deoxy-α-D-allopyranoside. Methyl 2-O-benzoyl-3-O-(tert-Butyldimethylsilyl)-6-deoxy-α-D-allopyranoside (4.68 g, 11.8 mmol) was dissolved in 25 mL pyridine, then benzoyl Chloride (1.65 mL, 14.2 mmol) was added, the mixture was stirred for 12 hrs, the solvent was removed under reduced pressure, the residue was dissolved in EtOAc (300 mL), washed with 5% HCl, NaHCO$_3$ solution, water, brine, dried over Na$_2$SO$_4$, concentrated, and purified with flash chromatography (hexane:EtOAc 10:1), gave pure product 5.71 g product, yield 96.6%. [α]$_D$=70.4 (c=1 CHCl$_3$); $^1$H NMR (CDCl$_3$): δ 8.19-7.43 (m, 10H), 5.17 (dd, J=2.9, 4.1 Hz, 1H), 4.87 (m, 2H), 4.65 (t, J=2.4 Hz, 1H), 4.53 (m, 1H), 3.44 (s, 3H), 1.28 9d, 3H, J=6.4 Hz), 0.90 (s, 9H), −0.115 (s, 3H), −0.25 (s, 3H); $^{13}$CNMR (CDCl$_3$): δ 165.97, 165.59, 134.52, 133.21, 130.54, 129.98, 129.93, 129.88, 129.83, 129.79, 128.85, 128.81, 128.36, 128.27, 97.78, 75.04, 68.24, 70.81, 61.13, 55.71, 25.56, 25.50, 18.10, 17.17; MS: calcd for C$_{27}$H$_{36}$O7SiNa 523.2, found: m/z 523.2 (M+Na).

Route to Compounds 113, 119, 120, 121 and 125— Methyl 2,4-di-O-benzoyl-6-deoxy-α-D-allopyranoside. Methyl 2,4-di-O-benzoyl-3-O-(tert-Butyldimethylsilyl)-6-deoxy-α-D-allopyranoside (5.7 g, 11.4 mmol) was dissolved in a mixture of pyridine (7 mL), CH$_3$CN (7 mL), this solution was cooed with ice bath, then 8 mL HF-pyridine was added, the mixture was stirred for at rom temperature, another 6 ml of HF-pyridine was added, The mixture was diluted with EtOAc (300 mL) gave 2.90 g product, yield 66%. $^1$H NMR (CDCl$_3$): δ: 8.13-8.08 (m,4H), 7.62-7.57 (m,2H), 7.48-7.44 (m,4H), 5.14 (t, J=3.5 hz, 1H), 5.10 (d, J=3.3 Hz, 1H), 4.80 (dd, J=2.7, 10.2 Hz, 1H), 4.55 (m, 1H) m 4.35 (m, 1H), 3.69 (br, 1H), 3.51 (s, 3H), 1.35 (d, J=6.2 Hz, 3H).

Route to Compounds 113, 119, 120, 121 and 125— Methyl 3-azide-2,4-di-O-benzoyl-3,6-dideoxy-α-D-glucopyranoside. Methyl 2,4-di-O-benzoyl-6-deoxy-α-D-allopyranoside (2.8 g, 7.25 mmol was dissolved in 50 mL dichloromethane, to this solution, 1.75 mL anhydrous pyridine was added, the mixture was cooled to −10° C., then 1.8 mL (10.7 mmol) triflic anhydride was added through a syringe, the reaction mixture was stirred for 30 min at to −10° C. and 2 hrs at room temperature. Diluted with 300 mL EtOAc, washed with 5% HCl, water, NaHCO$_3$ solution, brine, dried and concentrated, the resulting residue was dissolved in 25 mL anhydrous DMF, to this solution, 2.8 g NaN$_3$ was added, stirred at r.t overnight. Diluted with EtOAc and washed with water (3×40 ml), dried and concentrated, purified by chromatography, gave 2.50 g product, yield 84% for two steps. $^1$H NMR (CDCl$_3$): δ 8.12-8.08 (m, 4H), 7.63 (m, 2H), 7.53-7.46 (m, 4 H), 5.10 9d, J=3.5 Hz, 1H), 5.01 (m, 2H), 4.29 9 t, J=10.2 Hz, 1H), 4.05 (m, 1H), 3.44 9 s, 3H), 1.27 9d, J=6.3 Hz, 3H); $^{13}$CNMR (CDCl$_3$): δ 165.54, 165.18, 133.49, 130.11, 129.91, 129.81, 129.68, 129.14, 129.04, 128.49, 128.46, 96.28, 73.85, 72.83, 65.37, 61.64, 55.40, 17.26; MS: calcd for C$_{21}$H$_{21}$O$_6$N$_3$ Si 434.1, found: m/z 434.1 (M+Na).

Route to Compounds 113, 119, 120, 121 and 125—Ethyl 3-azide-2,4-di-O-benzoyl-3,6-dideoxy-1-thio-β-D-glucopyranoside. To a solution of Methyl 3-azide-2,4-di-O-benzoyl-3,6-dideoxy-α-D-glucopyranoside (2.5 g, 6.08 mmol) in 50 mL methanol, 1 mL 30% MeONa was added, the mixture was stirred overnight at room temperature, it was then neutralized with DOWEX 50WX8-100 ion-exchange resin, the filtrate was concentrated and dissolved in 27 mL 2N H$_2$SO$_4$, the mixture was stirred overnight at 120° C. After cooling to room temperature, saturated NaHCO$_3$ solution was added to neutralize sulfuric acid, the resulting solution was concentrated and purified by chromatography (hexane: EtOAc 1:3), get product 1.25 g. This compound was benzoylated with BzCl/Pyridine, the benzoyl protected sugar, TMSSEt (2 mL, 12.3 mmol) and ZnI$_2$ (5.8 g, 18.2 mmol) in 30 mL anhydrous dichloromethane was refluxed for 2 hrs under argon atmosphere. After cooling to room temperature, it was diluted with EtOAc (250 mL), washed with water (40 mL), saturated NaHCO$_3$ solution (40 mL), water (40 mL), dried over Na$_2$SO$_4$, concentrated and the resulting residue was purified with silica gel chromatography (hexane; EtOAc 8:1), got product 1.58 g, yield 59% for four steps. $^1$H NMR (CDCl$_3$): δ 8.10-8.06 (m, 4H), 7.63-7.58 (m, 2H), 7.50-7.45 (m, 4H), 5.29 (t, J=4.9 Hz, 1H), 5.11 (t, J=9.8 hz, 1H), 4.69 9d, J=9.9 Hz, 1H), 4.00 (t, J =9.8 Hz, 1H), 3.82 9 m, 1H), 2.76 (m, 2H), 1.34 (d, J=6.3 hz, 3H), 1.26 (t, J=7.4 Hz, 3H); $^{13}$CNMR (CDCl$_3$): δ 165.08, 164.89, 133.56, 133.41, 129.82, 129.74, 129.12, 128.91, 128.49, 128.4 0, 83.42, 75.23, 73.62, 70.82, 23.78, 17.64, 14.64; MS: calcd for C$_{22}$H$_{23}$O$_5$SNa 464.1, found: m/z 464.1 (M+Na).

Route to Compounds 113, 119, 120, 121 and 125—Ethyl 3-azide-2,4-di-O-benzyl-3,6-dideoxy-1-thio-β-D-glucopyranoside. Ethyl 3-azide-2,4-di-O-benzoyl-3,6-dideoxy-1-thio-β-D-glucopyranoside (2.0 g, 4.5 mmol) in 30 mL methanol was treated with 0.7 mL 30% (wt) NaOMe, it was then neutralized with DOWEX 50WX8-100 ion-exchange resin, the filtrate and washings were combined and concentrated, the residue was dissolved in 20 mL anhydrous DMF, NaH (720 mg 60%) and BnBr (3.23 mL, 27.1 mmol) were added to this solution. This reaction mixture was stirred overnight at r. t. It was then diluted with 200 mL EtOAc, washed water (3×20 mL), brine (30 mL), dried over Na$_2$SO$_4$, concentrated and purified (silica gel chromatography, gave 1.72 g product. Yield: 92%. $^1$H NMR (CDCl$_3$): δ 7.60-7.33 (m, 10H), 4.95 (d, J=10.0 Hz, 1H), 4.94 (d, J=10.0 Hz, 1H), 4.80 (d, J=10.1 Hz, 1H), 4.67 (d, J=10.7 Hz, 1H), 4.48 (d, J=9.7 Hz, 1H), 3.60 (t, J=9.5 Hz, 1H), 3.43 (m, 1H), 3.28 (t, J=9.5 hz, 1H), 3.05 9t, J=9.5 Hz, 1H), 2.81 9 m, 2H), 1.37 (m, 6H); $^{13}$CNMR (CDCl$_3$): δ 137.36, 137.26, 129.47, 128.58, 128.44, 128.36, 128.22, 128.02, 128.01, 84.85, 81.69, 80.30, 75.76, 75.26, 75.13, 70.25, 25.08, 18.04, 14.98; MS: calcd for C$_{22}$H$_{27}$N$_3$O$_3$Sna 436.1, found: m/z 435.9 (M+Na).

Route to Compounds 113, 119, 120, 121 and 125—Dibenzyl-(3-azide-2,4-di-O-benzyl-3,6-dideoxy-α-D-glucopyranosyl) phosphate. Use general procedure for the phosphorylation (via ethyl 1-thio-β-D-hexopyranoside). 416 mg Ethyl 3-azide-2,4-di-O-benzyl-3,6-dideoxy-1-thio-β-D-glucopyranoside (1.0 mmol) gave 524 mg product, yield: 82.7. [α]$_D$=54 (c=1, CHCl$_3$): $^1$H NMR (CDCl$_3$): δ 7.45-7.28 (m, 20H) 5.92 (dd, J=3.1, 6.9 Hz, 1H), 5.3-4.62 (m, 8H), 3.91 (m, 1H), 3.82 (t, J=9.8 Hz, 1H), 3.48 (m, 1H), 3.00 (t, J=9.6 Hz, 1H), 1.21 (d, J=6.3 hz, 3H);). $^{31}$P NMR (CDCl$_3$): δ 0.83; $^{13}$X NMP (XΔXλ$_3$): 137.33, 136.84, 135.60, 135.48, 128.45, 128.41, 128.33, 128.29, 128.21, 128.14, 128.10, 128.06, 128.01, 127.99, 127.86, 127.82, 127.70, 127.57, 94.14, 81.23, 75.06, 72.72, 69.33, 69.28, 69.04, 68.06, 64.46, 17.68; MS: calcd for C$_{34}$H$_{36}$N$_3$O$_7$PNa 652.2, found: m/z 652.2 (M+Na).

Disodium 3-amino-3,6-dideoxy-α-D-glucopyranosyl phosphate—Compound 113. Use general procedure for the final deprotection and conversion to the sodium salt.

Route to Compounds 113, 119, 120, 121 and 125—Dibenzyl-(3-azide-2,4-di-O-benzyl-3,6-dideoxy-α-D-glucopyranosyl) phosphate 500 mg (0.79 mmol) gave 104 mg product, Yield 62%. $^1$H NMR (D$_2$O): δ 5.34 (dd, J=3.1, 7.1 Hz, 1H), 3.92 (m, 1H), 3.64 9 dt, J=1.4, 10.4 Hz, 1H), 3.34 (m, 2H), 1.15 (d, J=6.3 Hz, 3H); $^{13}$C NMR (D$_2$O): δ 93.48, 72.72, 70.46, 69.02, 56.33, 17.47; $^{31}$PNMR (D$_2$O): δ 2.89; MS calcd for C$_6$H$_{14}$O$_7$NPNa 266.0, found m/z 266.1.

Route to Compounds 113, 119, 120, 121 and 125—Ethyl 3-acetamino-2,4-di-O-benzyl-3,6-dideoxy-1-thio-β-D-glucopyranoside. Ethyl 3-azide-2,4-di-O-benzyl-3,6-dideoxy-1-thio-β-D-glucopyranoside was converted into Ethyl 3-acetamino-2,4-di-O-benzyl-3,6-dideoxy-1-thio-β-D-glucopyranoside by using the same method as (Angew Chem Paper), 440 mg start material gave 335 mg pure product, yield 73.3%. $^1$H NMR (CDCl$_3$): δ 7.33-7.29 (m, 10 H), 5.80 (br, 1H), 4.86 (d, J=11.1 Hz, 1H), 4.63 (d, J=11.1 Hz, 1 H), 4.56 (m, 2H), 4.80 (d, J=9.3 Hz, 1H), 3.83 (m, 1H), 3.61 (t, J=9.7 Hz, 1H), 3.44 (m, 2H), 2.78 (m, 2H), 1.80 (s, 3H), 1.32 (m, 6H); ); $^{13}$CNMR (CDCl$_3$): δ 170.64, 137.99, 137.93, 128.62, 128.50, 128.36, 128.30, 128.22, 127.91, 127.76, 127.71, 85.41, 80.79, 78.67, 75.58, 74.31, 74.10, 58.17, 25.00, 18.32, 14.97; MS: calcd for C$_{24}$H$_{31}$NO$_4$SNa 452.1, found: 451.9 (M+Na).

Route to Compounds 113, 119, 120, 121 and 125—Dibenzyl-(3-acetamino-2,4-di-O-benzyl-3,6-dideoxy-α-D-glucopyranosyl) phosphate. Use general procedure for the phosphorylation (via ethyl 1-thio-β-D-hexopyranoside). 300 mg Ethyl 3-acetamino-2,4-di-O-benzyl-3,6-dideoxy-1-thio-β-D-glucopyranoside (0.7 mmol) gave 290 mg product, yield: 64.3% [α]$_D$=44 (c=1, CHCl$_3$). $^1$H NMR (CDCl$_3$): δ 7.36-7.25 (m, 20H), 5.92 (dd, J=3.3, 6.6 Hz, 1H), 5.56) br, 1H), 5.04 (m, 4H), 4.72 (d, J=11.5 Hz, 1H), 4.64 (d, J=11.2 Hz, 1H), 4.55 (d, J-11.2 Hz, 1H), 4.48 (d, J=11.5 Hz, 1H), 4.08 (m, 1H), 3.75 (m, 1H), 3.71 (m, 2H), 1.80 (s, 3H), 1.22 (d, J=6.2 Hz, 3H); $^{31}$P NMR (CDCl$_3$): δ 0.79; $^{13}$C NMR (CDCl$_3$): 178.21, 137.80, 137.45, 135.61, 128.39, 128.31, 128.27, 128.19, 127.95, 127.78, 127.77, 127.72, 127.53, 127.42, 94.98, 79.59, 75.01, 74.94, 72.42, 69.46, 68.98, 53.93, 23.49; MS: calcd for C$_{36}$H$_{40}$NO$_8$PNa 668.2, found: m/z 668.4 (M+Na).

Disodium 3-acetamino-3,6-dideoxy-α-D-glucopyranosyl phosphate—Compound 125. Use general procedure for the final deprotection and conversion to the sodium salt. Dibenzyl-(3-aaetamino-2,4-di-O-benzyl-3,6-dideoxy-α-D-glucopyranosyl) phosphate (168 mg, 0.26 mmol) gave 39 mg product, yield: 53%. $^1$H NMR (D$_2$O): δ 5.41 (dd, J=3.3, 6.8 Hz, 1H), 4.04 9t, J=10.3 Hz, 1H), 3.96 (m, 1H), 3.58 (m, 1H), 3.15 9t, J=9.8 Hz, 1H), 2.03 (s, 3H), 1.24 (d, J=6.3 hz, 3H);

$^{31}$P NMR (D$_2$O): δ 0.66; $^{13}$C NMR (D$_2$O): δ 172.98, 91.59, 71.35, 68.25, 66.58, 51.80, 20.12, 14.74; MS calcd for C$_6$H$_{16}$O$_8$NPNa 308.0, found m/z 308.1.

Route to Compounds 113, 119, 120, 121 and 125—Ethyl 2,4-di-O-benzyl-3,6-dideoxy-3-dimethylamino-1-thio-β-D-glucopyranoside. Ethyl 3-azide-2,4-di-O-benzyl-3,6-dideoxy-1-thio-β-D-glucopyranoside (450 mg, 1.09 mmol) was reduced to Ethyl 3-amino-2,4-di-O-benzyl-3,6-dideoxy-1-thio-β-D-glucopyranoside, the crude product was converted into Ethyl 2,4-di-O-benzyl-3,6-dideoxy-3-dimethylamino-1-thio-β-D-glucopyranoside (ref: J. Org. Chem 1996, 6153-6161), gave pure product 390 mg. Yield: 86%. [α]$_D$=−6.3 (c=1, CHCl$_3$). $^1$H NMR (CDCl$_3$): δ 7.53-7.29 (m, 10H), 4.94 (m, 2H), 4.73 (d, J=10.2 Hz, 1H), 4.60 (d, J=10.6 Hz, 1H), 4.45 (d, J=9.5 Hz, 1H), 3.42 (m, 2H), 3.13 (m, 1H), 2.85 (t, J=9.7 hz, 1H), 2.79 (m, 2H), 2.59 (s, 6H), 1.57 (s, 3H), 1.37-1.25 (m, 6 H); MS: calcd for C$_{22}$H$_{30}$NO$_3$S 452.1, found: m/z 416.2 (M+Na).

Route to Compounds 113, 119, 120, 121 and 125—Dibenzyl-(2,4-di-O-benzyl-3,6-dideoxy-3-dimethylamino-α-D-glucopyranosyl) phosphate. Use general procedure for the phosphorylation (via ethyl 1-thio-β-D-hexopyranoside). 390 mg Ethyl 2,4-di-O-benzyl-3,6-dideoxy-3-dimethylamino-1-thio-β-D-glucopyranoside gave 195 mg product, yield 33%. $^1$H NMR (CDCl$_3$): δ 7.44-7.25 (m,20H), 6.06 (dd, J=3.1, 6.6 hz, 1H), 5.10 -4.83 (m, 5H), 4.84 (d, J=10.8 Hz, 1H), 4.59 (m, 3H), 3.94 (m, 1H), 3.67 (m, 1H), 3.14 9 m, 2H), 3.28 (s, 6H), 1.24 (d, J=6.2 Hz, 3H); $^{13}$CNMR (CDCl$_3$): δ 138.55, 137.51, 135.83, 128.48, 128.37, 128.32, 128.23, 128.09, 127.78, 127.72, 127.64, 127.61, 94.76, 78.72, 75.90, 74.62, 72.35, 69.86, 69.25, 69.01, 65.12, 41.7, 18.23; $^{31}$P NMR (CDCl$_3$): δ 0.91; MS: calcd for C$_{36}$H$_{43}$NO$_7$PNa 654.3, found: m/z 654.3 (M+Na).

Disodium 3,6-dideoxy-3-dimethylamino-α-D-glucopyranosyl phosphate—Compound 120. Use general procedure for the final deprotection and conversion to the sodium salt. Dibenzyl-(2,4-di-O-benzyl-3,6-dideoxy-3-dimethylamino-α-D-glucopyranosyl) phosphate 180 mg (with impurity) gave 22 mg product, yield 29%. $^1$H NMR (D$_2$O): δ 5.39 (dd, J=3.1, 6.8 hz, 1H), 3.98 (m, 1H), 3.88 (m, 1H), 3.50 (m, 2H), 2.96 9 s, 6H), 1.22 (d, J=6.2 Hz, 3H); $^{31}$P NMR (D$_2$O): δ 2.83; $^{13}$C NMR (D$_2$O): δ 92.42, 68.56, 67.97, 67.53, 66.66, 40.75, 16.05; MS: calcd for C$_8$H$_{18}$NO$_7$PNa 294.0, found: m/z 294.0 (M+Na). Compounds 19 and 21 generated via similar strategies from appropriate starting materials.

Generation of Nucleotide Sugars. Conversion to UDP-/TDP-activated sugars as previously described using wild-type Ep, a Ep Trp224-His mutant, a Ep Leu89-Thr mutant and/or a Ep Tyr177-Phe mutant. All products confirmed by HPLC isolation and HRMS using previously described methodology.

Example 8

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a compound of the present invention which is effective for producing some desired therapeutic effect by inhibiting a bacterial infection in in an animal and thereby blocking the biological consequences of bacterial infection in the treated animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject deacetylase inhibitor agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as com starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds inhibitors may contain a basic functional group, such as amino or alkyl amino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J Pharm. Sci. 66:1-19)

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the deacetylase inhibitor which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered deacetylase inhibitor moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active deacetylase inhibitor, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active deacetylase inhibitor.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compoundr of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to a compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the deacetylase inhibitor in the proper medium. Absorption enhancers can also be used to increase the flux of the deacetylase inhibitor across the skin. The rate of such flux can be controlled by either providing a rate controlling membrane or dispersing the deacetylase inhibitor in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium cWoride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject deacetylase inhibitors in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The compound may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular deacetylase inhibitor employed, or the ester, salt or amide thereof, the route of administration, the time of administration, the rate of excretion of the particular compound being employed, the duration of the treatment, other drugs, compounds and/or materials used in combination with the particular deacetylase inhibitor employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

The invention has been herein shown and described in what is perceived to be preferred embodiments, it is to be understood that the invention is not intended to be limited to the specific embodiments set forth above. Rather, it is recognized that certain modifications, substitutions, alterations, omissions may be made by one of skill in the art of the invention without departing from the spirit or intent of the invention. Accordingly, the invention is to be taken as including all reasonable equivalents to the subject matter of the appended claims and the foregoing description is meant to be exemplary only and should not limit the scope of the invention set forth in the following claims.

What is claimed is:

1. A method of producing a chemoselectively ligated vancomycin analog comprising incubating at least one glycosylated vancomycin comprising a glycosyl moiety selected from the group consisting of:

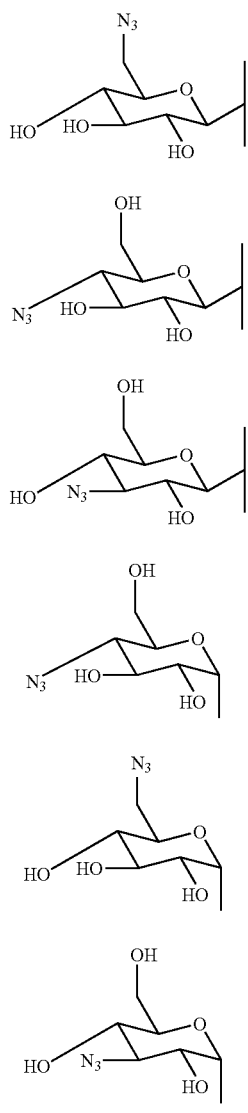
with a chemoselectively ligatable agent comprising an alkyne moiety, wherein the glycosyl moiety and chemoselectively ligatable agent react to provide a chemoselectively ligated vancomycin analog having a structure selected from the group consisting of:
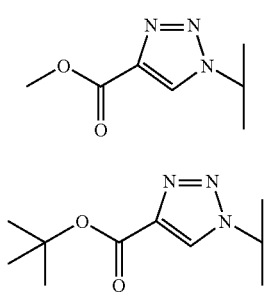
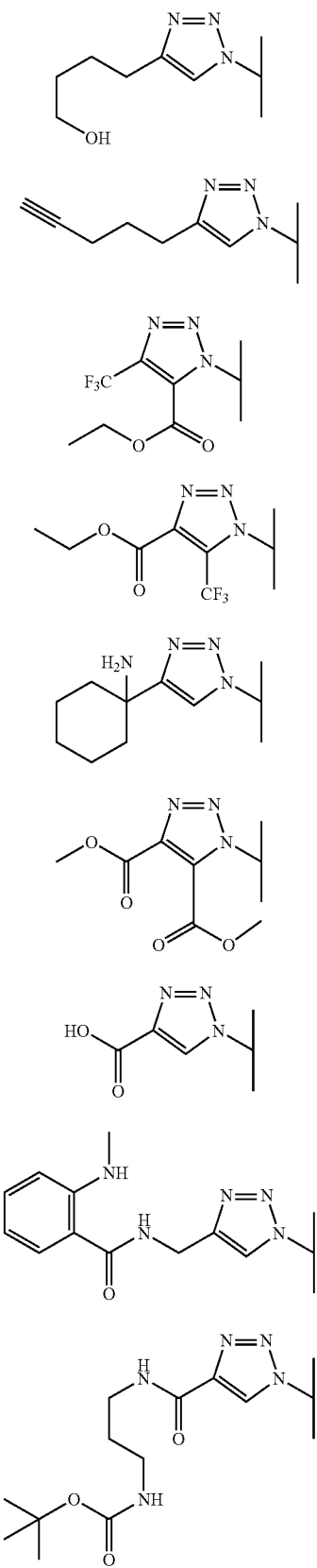

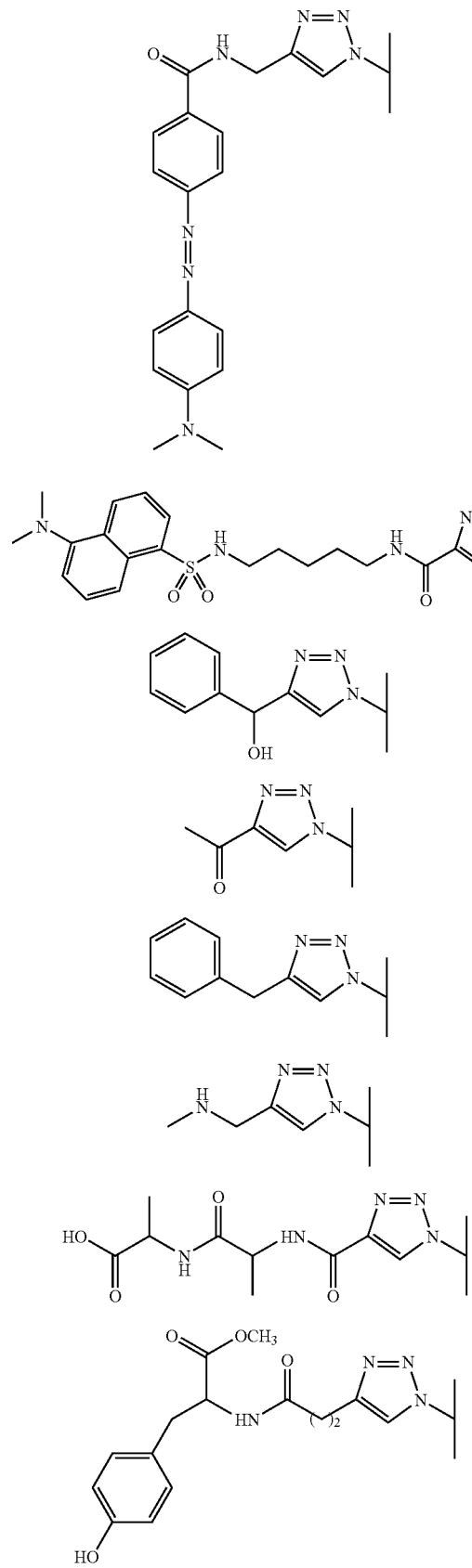

-continued

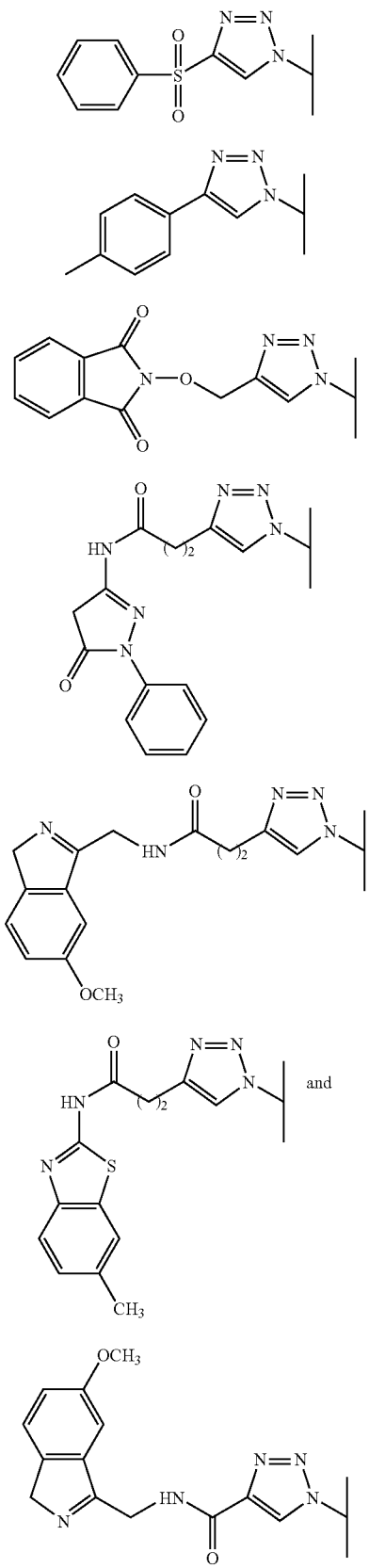

140
141
142
143
144
145
146 wherein at least one chemoselectively ligated vancomycin analog is produced.

2. A method according to claim 1, further, wherein the glycosylated vancomycin is initially produced by incubating vancomycin and at least one thymidine or uridine nucleotide diphosphosugar comprising a sugar structure selected from the group consisting of:

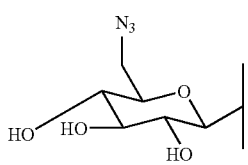

50

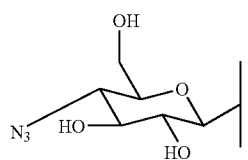

51

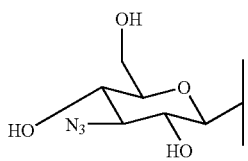

52

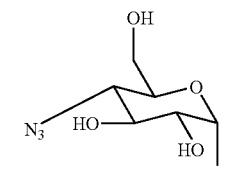

109

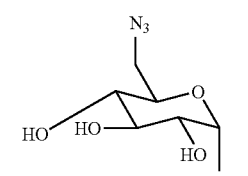

115

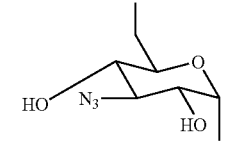

117 in the presence of at least one first glycosyltransferase wherein the at least glycosylated vancomycin is produced.

* * * * *